US010421789B2

(12) United States Patent
Huang et al.

(10) Patent No.: US 10,421,789 B2
(45) Date of Patent: Sep. 24, 2019

(54) ENGINEERED OUTER DOMAIN (EOD) OF HIV GP120 AND MUTANTS THEREOF

(71) Applicants: University of Washington, Center for Commercialization, Seattle, WA (US); The Scripps Research Institute, La Jolla, CA (US); International AIDS Vaccine Initiative, New York, NY (US)

(72) Inventors: Po-Ssu Huang, Seattle, WA (US); Joseph Graham Jardine, Seattle, WA (US); Sergey V. Menis, Bothell, WA (US); William Ray Schief, Encinitas, CA (US); Neil P. King, Seattle, WA (US)

(73) Assignees: University of Washington, Center for Commercialization, Seattle, WA (US); The Scripps Research Institute, La Jolla, CA (US); International AIDS Vaccine Initiative, New York, NY (US)

( * ) Notice: Subject to any disclaimer, the term of this patent is extended or adjusted under 35 U.S.C. 154(b) by 0 days.

(21) Appl. No.: 16/291,726

(22) Filed: Mar. 4, 2019

(65) Prior Publication Data

US 2019/0194262 A1    Jun. 27, 2019

Related U.S. Application Data

(63) Continuation of application No. 14/978,132, filed on Dec. 22, 2015, now Pat. No. 10,221,217, which is a continuation of application No. 14/251,132, filed on Apr. 11, 2014, now abandoned, which is a continuation of application No. PCT/US2012/060062, filed on Oct. 12, 2012.

(60) Provisional application No. 61/699,217, filed on Sep. 10, 2012, provisional application No. 61/546,465, filed on Oct. 12, 2011.

(51) Int. Cl.
| *A61K 39/00* | (2006.01) |
| *A61K 39/21* | (2006.01) |
| *C07K 16/10* | (2006.01) |
| *A61K 39/12* | (2006.01) |
| *C07K 14/005* | (2006.01) |
| *G01N 33/564* | (2006.01) |
| *A61K 38/00* | (2006.01) |

(52) U.S. Cl.
CPC ............ *C07K 14/005* (2013.01); *A61K 38/00* (2013.01); *A61K 39/12* (2013.01); *A61K 39/21* (2013.01); *G01N 33/564* (2013.01); *C12N 2740/16122* (2013.01); *C12N 2740/16134* (2013.01)

(58) Field of Classification Search
CPC ............ C07K 2317/76; C07K 16/1063; C07K 14/005; A61K 39/12; A61K 39/21
See application file for complete search history.

(56) References Cited

U.S. PATENT DOCUMENTS

| 2009/0191235 A1 | 7/2009 | Kwong et al. |
| 2010/0068217 A1 | 3/2010 | Kwong et al. |
| 2011/0217338 A1 | 9/2011 | Phogat et al. |
| 2012/0288502 A1 | 11/2012 | Diskin et al. |

FOREIGN PATENT DOCUMENTS

| EP | 2302059 | 3/2011 |
| WO | 2008/025015 | 2/2008 |
| WO | 2011038290 | 3/2011 |

OTHER PUBLICATIONS

Supplementary European Search Report dated Apr. 10. 2015. issued in European Application No. 12839873.6.
Berkower, et al., Targeted deletion in the B20-B21 loop of HIV envelope glycoprotein gp120 exposes the ?04 binding site for antibody binding, Virology (Aug. 2008) 377(2).330-338.
Xinzhen Yang, et al., Characterization of the Outer Domain of the gp120 Glycoprotein from Human Immunodeficiency Virus Type 1 , Journal of Virology (Dec. 2004) 78(23);12975-12986.
Dunfee, et al., Enhanced macrophage tropism of HIV in brain and lymphoid tissues is associated with sensitivity to he broadly neutralizing CD 4 binding site antibody b12. Retrovirology (Jul. 2009) 6:69.
International Search Report dated Mar. 25, 2013, issued in International Application No. PCT/US2012/060062.

*Primary Examiner* — Barry A Chestnut
(74) *Attorney, Agent, or Firm* — Duane Morris LLP; Thomas J. Kowalski; Deborah L. Lu

(57) ABSTRACT

The invention relates to an engineered outer domain (eOD) of HIV gp120 and mutants thereof and methods of making and using the same. The mutant eODs may be advantageous for the elicitation of CD4-binding site (CD4bs)-directed broadly-neutralizing antibodies (bnAbs) and/or improve binding to mature VRC01 and/or improve binding to germline VRC01 and the germlines of other VH1-2 derived broadly-neutralizing antibodies. The mutant eODs may also include glycan-masking mutations on eOD. The present invention also includes fusions of eOD to various protein multimers to enhance immunogenicity as well as the design of cocktails of different eODs that represent the full diversity of HIV sequences within the VRC01 epitope and surroundings.

20 Claims, 9 Drawing Sheets

Specification includes a Sequence Listing.

eOD_VD(-)_60mer_1hqk_3 eOD_VH1-2_v6.0_1hqk_1

SEQUENCE LISTING

```
<160> NUMBER OF SEQ ID NOS: 153

<210> SEQ ID NO 1
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Arg Pro Val Val Ser Thr Gln Leu Leu Leu Asn Gly Ser Leu Ala Glu
1               5                   10                  15

Glu Glu Val Val Ile Arg Ser Val Asn Phe Thr Asp Asn Ala Lys Thr
            20                  25                  30

Ile Ile Val Gln Leu Asn Thr Ser Val Glu Ile Asn Cys Thr Gly Ala
        35                  40                  45

Gly His Cys Asn Ile Ser Arg Ala Lys Trp Asn Asn Thr Leu Lys Gln
    50                  55                  60

Ile Ala Ser Lys Leu Arg Glu Gln Phe Gly Asn Asn Lys Thr Ile Ile
65                  70                  75                  80

Phe Lys Gln Ser Ser Gly Gly Asp Pro Glu Ile Val Thr His Ser Phe
                85                  90                  95

Asn Cys Gly Gly Glu Phe Phe Tyr Cys Asp Ser Thr Gln Leu Phe Asn
            100                 105                 110

Ser Thr Trp Phe Asn Ser Thr Trp Ser Thr Glu Gly Ser Asn Asn Thr
        115                 120                 125

Glu Gly Ser Asp Thr Ile Thr Leu Pro Cys Arg Pro Ala Pro Pro Pro
    130                 135                 140

His Cys Ser Ser Asn Ile Thr Gly Leu Leu Leu Thr Arg Asp Gly Gly
145                 150                 155                 160

Asn Ser Asn Asn Glu Ser Glu Ile Phe Arg Pro Gly Gly Gly Asp Met
                165                 170                 175

Arg Asp Asn Trp Arg Ser Glu
            180

<210> SEQ ID NO 2
```

```
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Arg Pro Val Val Ser Thr Gln Leu Leu Leu Asn Gly Ser Leu Ala Glu
1               5                   10                  15

Glu Glu Val Val Ile Arg Ser Val Asn Phe Thr Asp Asn Ala Lys Thr
            20                  25                  30

Ile Ile Val Gln Leu Asn Thr Ser Val Glu Ile Asn Cys Thr Gly Ala
        35                  40                  45

Gly His Cys Asn Ile Ser Arg Ala Lys Trp Asn Asn Thr Leu Lys Gln
    50                  55                  60

Ile Ala Ser Lys Leu Arg Glu Gln Phe Gly Asn Asn Lys Thr Ile Ile
65                  70                  75                  80

Phe Lys Gln Ser Ser Gly Gly Asp Pro Glu Ile Val Thr His Ser Phe
                85                  90                  95

Asn Cys Gly Gly Glu Phe Phe Tyr Cys Asn Ser Thr Gln Leu Phe Asn
            100                 105                 110

Ser Thr Trp Phe Asn Ser Thr Trp Ser Thr Glu Gly Ser Asn Asn Thr
        115                 120                 125

Glu Gly Ser Asp Thr Ile Thr Leu Pro Cys Arg Pro Ala Pro Pro
    130                 135                 140

His Cys Ser Ser Asn Ile Thr Gly Leu Leu Leu Thr Arg Asp Gly Gly
145                 150                 155                 160

Asn Ser Asn Asn Glu Ser Glu Ile Phe Arg Pro Gly Gly Gly Asp Met
                165                 170                 175

Arg Asp Asn Trp Arg Ser Glu
            180

<210> SEQ ID NO 3
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Thr Ile Thr Leu Pro Cys Arg Pro Ala Pro Pro His Cys Ser
1               5                   10                  15

Ser Asn Ile Thr Gly Leu Leu Leu Thr Arg Asp Gly Gly Asn Ser Asn
            20                  25                  30

Asn Glu Ser Glu Ile Phe Arg Pro Gly Gly Gly Asp Met Arg Asp Asn
        35                  40                  45

Trp Arg Ser Gly Leu Ser Gly Pro Val Val Ser Thr Gln Leu Leu Leu
    50                  55                  60

Asn Gly Ser Leu Ala Glu Glu Val Val Ile Arg Ser Val Asn Phe
65                  70                  75                  80

Thr Asp Asn Ala Lys Thr Ile Ile Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125
```

```
Asn Asn Lys Thr Ile Ile Phe Lys Gln Ser Ser Gly Gly Asp Pro Glu
            130                 135                 140

Ile Val Thr His Ser Phe Asn Cys Gly Gly Glu Phe Phe Tyr Cys Asp
145                 150                 155                 160

Ser Thr Gln Leu Phe Asn Ser Thr Trp Phe Asn Ser Thr Trp Ser
            165                 170                 175

<210> SEQ ID NO 4
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Glu Phe Phe Tyr Cys Asp Ser Thr Gln Leu Phe Asn Ser Thr Trp
1               5                   10                  15

Phe Asn Ser Thr Trp Ser Thr Glu Gly Ser Asn Asn Thr Glu Gly Ser
            20                  25                  30

Asp Thr Ile Thr Leu Pro Cys Arg Pro Ala Pro Pro His Cys Ser
            35                  40                  45

Ser Asn Ile Thr Gly Leu Leu Leu Thr Arg Asp Gly Gly Asn Ser Asn
50                  55                  60

Asn Glu Ser Glu Ile Phe Arg Pro Gly Gly Gly Asp Met Arg Asp Asn
65                  70                  75                  80

Trp Arg Ser Gly Leu Ser Gly Pro Val Val Ser Thr Gln Leu Leu Leu
                85                  90                  95

Asn Gly Ser Leu Ala Glu Glu Val Val Ile Arg Ser Val Asn Phe
            100                 105                 110

Thr Asp Asn Ala Lys Thr Ile Ile Val Gln Leu Asn Thr Ser Val Glu
            115                 120                 125

Ile Asn Cys Thr Gly Ala Gly His Cys Asn Ile Ser Arg Ala Lys Trp
            130                 135                 140

Asn Asn Thr Leu Lys Gln Ile Ala Ser Lys Leu Arg Glu Gln Phe Gly
145                 150                 155                 160

Asn Asn Lys Thr Ile Ile Phe Lys Gln Ser Ser Gly Gly Asp Pro Glu
            165                 170                 175

Ile Val Thr His Ser Phe Asn Cys Gly
            180                 185

<210> SEQ ID NO 5
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
50                  55                  60
```

```
Asn Gly Ser Leu Ala Glu Glu Val Val Ile Arg Ser Val Asn Phe
 65                  70                  75                  80

Thr Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
            115                 120                 125

Asn Asn Lys Thr Ile Ile Phe Lys Gln Ser Ser Gly Gly Asp Pro Glu
        130                 135                 140

Ile Val Thr His Ser Phe Asn Cys Gly Gly Glu Phe Phe Tyr Cys Asp
145                 150                 155                 160

Ser Thr Gln Leu Phe Asn Ser Thr Trp Phe Asn Ser Thr Trp Ser
                165                 170                 175

<210> SEQ ID NO 6
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Thr Ile Thr Leu Pro Cys Arg Pro Ala Pro Pro His Cys Ser
 1               5                  10                  15

Ser Asn Ile Thr Gly Leu Ile Leu Thr Arg Asp Gly Gly Asn Ser Asn
             20                  25                  30

Asn Glu Ser Glu Ile Phe Arg Pro Gly Gly Gly Asp Met Arg Asp Ile
         35                  40                  45

Ala Arg Cys Gln Ile Ala Gly Thr Val Val Ser Thr Gln Leu Leu Leu
     50                  55                  60

Asn Gly Ser Leu Ala Glu Glu Val Val Cys Arg Ser Val Asn Phe
 65                  70                  75                  80

Thr Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Cys Leu Arg Glu Gln Phe Gly
            115                 120                 125

Asn Asn Lys Thr Ile Ile Phe Lys Gln Ser Ser Gly Gly Asp Pro Glu
        130                 135                 140

Ile Val Thr His Ser Phe Asn Cys Gly Gly Glu Phe Phe Tyr Cys Asp
145                 150                 155                 160

Ser Thr Gln Leu Phe Asn Ser Thr Trp Phe Asn Ser Thr Trp Ser
                165                 170                 175

<210> SEQ ID NO 7
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Thr Ile Thr Leu Pro Cys Arg Pro Ala Pro Pro His Cys Ser
 1               5                  10                  15
```

Ser Asn Ile Thr Gly Leu Ile Leu Thr Arg Asp Gly Asn Ser Asn
            20                  25                  30

Asn Glu Ser Glu Ile Phe Arg Pro Gly Gly Gly Asp Met Ala Gly Met
        35                  40                  45

Pro Arg Cys Gly Gly Gly Ala Val Ser Thr Gln Leu Leu Leu Asn Gly
50                  55                  60

Ser Leu Ala Glu Glu Glu Val Val Cys Arg Ser Val Asn Phe Thr Asp
65                  70                  75                  80

Asn Ala Lys Ser Ile Cys Val Gln Leu Asn Thr Ser Val Glu Ile Asn
                85                  90                  95

Cys Thr Gly Ala Gly His Cys Asn Ile Ser Arg Ala Lys Trp Asn Asn
            100                 105                 110

Thr Leu Lys Gln Ile Ala Ser Cys Leu Arg Glu Gln Phe Gly Asn Asn
            115                 120                 125

Lys Thr Ile Ile Phe Lys Gln Ser Ser Gly Gly Asp Pro Glu Ile Val
130                 135                 140

Thr His Ser Phe Asn Cys Gly Gly Glu Phe Phe Tyr Cys Asp Ser Thr
145                 150                 155                 160

Gln Leu Phe Asn Ser Thr Trp Phe
                165

<210> SEQ ID NO 8
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asp Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asp Thr Ser Val Glu
                85                  90                  95

Ile Asp Cys Thr Gly Ala Gly His Cys Asp Ile Ser Arg Ala Lys Trp
            100                 105                 110

Asp Asn Thr Leu Lys Gln Ile Ala Ser Lys Leu Arg Glu Gln Phe Gly
            115                 120                 125

Asn Asp Lys Thr Ile Ile Phe Lys Gln Ser Ser Gly Gly Asp Pro Glu
        130                 135                 140

Ile Val Thr His Ser Phe Asn Cys Gly Gly Glu Phe Phe Tyr Cys Asp
145                 150                 155                 160

Ser Thr Gln Leu Phe Asp Ser Thr Trp Phe Asp Ser Thr Trp Ser
                165                 170                 175

<210> SEQ ID NO 9
<211> LENGTH: 185
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 9

Gly Glu Phe Phe Tyr Cys Asp Ser Thr Gln Leu Phe Asn Ser Thr Trp
1               5                   10                  15

Phe Asn Ser Thr Trp Ser Thr Glu Gly Ser Asn Asn Thr Glu Gly Ser
            20                  25                  30

Asp Thr Ile Thr Leu Pro Cys Arg Pro Ala Pro Pro His Cys Ser
        35                  40                  45

Ser Asn Ile Thr Gly Leu Ile Leu Thr Arg Asp Gly Asn Ser Asn
    50                  55                  60

Asn Glu Ser Glu Ile Phe Arg Pro Gly Gly Asp Met Arg Asp Ile
65                  70                  75                  80

Ala Arg Cys Gln Ile Ala Gly Thr Val Val Ser Thr Gln Leu Leu Leu
                85                  90                  95

Asn Gly Ser Leu Ala Glu Glu Val Val Ile Arg Ser Val Asn Phe
            100                 105                 110

Thr Asp Asn Ala Lys Ser Ile Cys Val Gln Leu Asn Thr Ser Val Glu
            115                 120                 125

Ile Asn Cys Thr Gly Ala Gly His Cys Asn Ile Ser Arg Ala Lys Trp
        130                 135                 140

Asn Asn Thr Leu Lys Gln Ile Ala Ser Lys Leu Arg Glu Gln Phe Gly
145                 150                 155                 160

Asn Asn Lys Thr Ile Ile Phe Lys Gln Ser Ser Gly Gly Asp Pro Glu
                165                 170                 175

Ile Val Thr His Ser Phe Asn Cys Gly
            180                 185

<210> SEQ ID NO 10
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Glu Phe Phe Tyr Cys Asp Ser Thr Gln Leu Phe Asn Ser Thr Trp
1               5                   10                  15

Phe Asn Ser Thr Trp Ser Thr Glu Gly Ser Asn Asn Thr Glu Gly Ser
            20                  25                  30

Asp Thr Ile Thr Leu Pro Cys Arg Pro Ala Pro Pro His Cys Ser
        35                  40                  45

Ser Asn Ile Thr Gly Leu Ile Leu Thr Arg Asp Gly Asn Ser Asn
    50                  55                  60

Asn Glu Ser Glu Ile Phe Arg Pro Gly Gly Asp Met Arg Cys Gly
65                  70                  75                  80

Ala Arg Ser Gly Ile Ala Gly Thr Val Val Ser Thr Gln Leu Leu Leu
                85                  90                  95

Asn Gly Ser Leu Ala Glu Glu Val Val Ile Arg Ser Val Asn Phe
            100                 105                 110

Thr Asp Asn Ala Lys Cys Ile Ile Val Gln Leu Asn Thr Ser Val Glu
            115                 120                 125

Ile Asn Cys Thr Gly Ala Gly His Cys Asn Ile Ser Arg Ala Lys Trp

```
            130                 135                 140
Asn Asn Thr Leu Lys Gln Ile Ala Ser Lys Leu Arg Glu Gln Phe Gly
145                 150                 155                 160

Asn Asn Lys Thr Ile Ile Phe Lys Gln Ser Ser Gly Gly Asp Pro Glu
                165                 170                 175

Ile Val Thr His Ser Phe Asn Cys Gly
            180                 185

<210> SEQ ID NO 11
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Glu Phe Phe Tyr Cys Asp Ser Thr Gln Leu Phe Asn Ser Thr Trp
1               5                   10                  15

Phe Asn Ser Thr Trp Ser Thr Glu Gly Ser Asn Asn Thr Glu Gly Ser
                20                  25                  30

Asp Thr Ile Thr Leu Pro Cys Arg Pro Ala Pro Pro His Cys Ser
            35                  40                  45

Ser Asn Ile Thr Gly Leu Ile Leu Thr Arg Asp Gly Gly Asn Ser Asn
50                  55                  60

Asn Glu Ser Glu Ile Phe Arg Pro Gly Gly Gly Asp Met Arg Asp Ile
65                  70                  75                  80

Ala Arg Cys Gln Ile Ala Gly Thr Val Val Ser Thr Gln Leu Leu Leu
                85                  90                  95

Asn Gly Ser Leu Ala Glu Glu Glu Val Val Cys Arg Ser Val Asn Phe
            100                 105                 110

Thr Asp Asn Ala Lys Ser Ile Cys Val Gln Leu Asn Thr Ser Val Glu
            115                 120                 125

Ile Asn Cys Thr Gly Ala Gly His Cys Asn Ile Ser Arg Ala Lys Trp
130                 135                 140

Asn Asn Thr Leu Lys Gln Ile Ala Ser Cys Leu Arg Glu Gln Phe Gly
145                 150                 155                 160

Asn Asn Lys Thr Ile Ile Phe Lys Gln Ser Ser Gly Gly Asp Pro Glu
                165                 170                 175

Ile Val Thr His Ser Phe Asn Cys Gly
            180                 185

<210> SEQ ID NO 12
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
```

```
                    50                  55                  60
Asn Gly Ser Leu Ala Glu Glu Val Val Ile Arg Ser Val Asn Phe
 65                  70                  75                  80

Thr Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Asn Lys Thr Ile Ile Phe Lys Gln Ser Ser Gly Gly Asp Pro Glu
                130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 13
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Thr Ile Thr Leu Pro Cys Arg Pro Ala Pro Pro His Cys Ser
  1               5                  10                  15

Ser Asn Ile Thr Gly Leu Ile Leu Thr Arg Asp Gly Gly Asn Ser Asn
                 20                  25                  30

Asn Glu Ser Glu Ile Phe Arg Pro Gly Gly Gly Asp Met Arg Asp Ile
                 35                  40                  45

Ala Arg Cys Gln Ile Ala Gly Thr Val Val Ser Thr Gln Leu Leu Leu
                 50                  55                  60

Asn Gly Ser Leu Ala Glu Glu Val Val Ile Arg Ser Val Asp Phe
 65                  70                  75                  80

Thr Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Asn Lys Thr Ile Ile Phe Lys Gln Ser Ser Gly Gly Asp Pro Glu
                130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 14
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Thr Ile Thr Leu Pro Cys Arg Pro Ala Pro Pro His Cys Ser
```

```
1               5                   10                  15
Ser Asn Ile Thr Gly Leu Ile Leu Thr Arg Asp Gly Asn Ser Asn
                20                  25                  30
Asp Glu Ser Glu Ile Phe Arg Pro Gly Gly Asp Met Arg Asp Ile
                35                  40                  45
Ala Arg Cys Gln Ile Ala Gly Thr Val Val Ser Thr Gln Leu Leu
                50                  55                  60
Asn Gly Ser Leu Ala Glu Glu Val Val Ile Arg Ser Val Asp Phe
 65                 70                  75                  80
Thr Asp Asn Ala Lys Ser Ile Cys Val Gln Leu Asn Thr Ser Val Glu
                85                  90                  95
Ile Asn Cys Thr Gly Ala Gly His Cys Asn Ile Ser Arg Ala Lys Trp
                100                 105                 110
Asn Asn Thr Leu Lys Gln Ile Ala Ser Lys Leu Arg Glu Gln Phe Gly
                115                 120                 125
Asn Asn Lys Thr Ile Ile Phe Lys Gln Ser Ser Gly Gly Asp Pro Glu
                130                 135                 140
Ile Val Thr His Ser Phe Asn Cys Gly Gly Glu Phe Phe Tyr Cys Asn
145                 150                 155                 160
Ser Thr Gln Leu Phe Asn Ser Thr Trp Phe Asn Ser Thr Trp Ser
                165                 170                 175
```

<210> SEQ ID NO 15
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Asp Thr Ile Thr Leu Pro Cys Arg Pro Ala Pro Pro His Cys Ser
1               5                   10                  15
Ser Asn Ile Thr Gly Leu Ile Leu Thr Arg Asp Gly Asn Ser Asn
                20                  25                  30
Asn Glu Ser Glu Ile Phe Arg Pro Gly Gly Gly Asp Met Arg Asp Ile
                35                  40                  45
Ala Arg Cys Gln Ile Ala Gly Thr Val Val Ser Thr Gln Leu Phe Leu
                50                  55                  60
Asn Gly Ser Leu Ala Glu Glu Val Val Ile Arg Ser Val Asn Phe
 65                 70                  75                  80
Thr Asp Asn Ala Lys Ser Ile Cys Val Gln Leu Asn Thr Ser Val Glu
                85                  90                  95
Ile Asn Cys Thr Gly Ala Gly His Cys Asn Ile Ser Arg Ala Lys Trp
                100                 105                 110
Asn Asn Thr Leu Lys Gln Ile Ala Ser Lys Leu Arg Glu Gln Phe Gly
                115                 120                 125
Asn Asn Lys Thr Ile Ile Phe Lys Gln Ser Ser Gly Gly Asp Pro Glu
                130                 135                 140
Ile Val Thr His Ser Phe Asn Cys Gly Gly Glu Phe Phe Tyr Cys Asn
145                 150                 155                 160
Ser Thr Gln Leu Phe Asn Ser Thr Trp Phe Asn Ser Thr Trp Ser
                165                 170                 175
```

<210> SEQ ID NO 16
<211> LENGTH: 175

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 17
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asp Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140
```

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 18
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Gly Asp Met Arg Asp Asn
                35                  40                  45

Ala Arg Cys Gln Ile Ala Gly Thr Val Val Ser Thr Gln Leu Leu Leu
            50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Asn Lys Thr Ile Ile Phe Lys Gln Ser Ser Gly Gly Asp Pro Glu
                130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 19
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Gly Asp Met Arg Asp Ile
                35                  40                  45

Ala Arg Cys Gln Ile Ala Gly Thr Val Val Ser Thr Gln Leu Leu Leu
            50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Lys Thr Ile Ile Phe Lys Gln Ser Ser Gly Gly Asp Pro Glu Ile
        130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr Trp Ser
            165                 170

<210> SEQ ID NO 20
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
        50                  55                  60

Asn Gly Ser Leu Ala Glu Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
        130                 135                 140

Ile Val Thr His Ser Phe Asn Cys Gly Gly Glu Phe Phe Tyr Cys Asn
145                 150                 155                 160

Thr Thr Gln Leu Phe Asn Ser Thr Trp Phe Asn Ser Thr Trp Ser
            165                 170                 175

<210> SEQ ID NO 21
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

```
Ala Arg Cys Gln Ile Ala Gly Thr Val Val Ser Thr Gln Leu Leu Leu
     50                  55                  60

Asn Gly Ser Leu Ala Glu Glu Ile Val Ile Arg Ser Val Asn Phe
 65                  70                  75                  80

Thr Asp Asn Ala Lys Ser Ile Cys Val Gln Leu Asn Thr Ser Val Glu
                     85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Asn Lys Thr Ile Ile Phe Lys Gln Ser Ser Gly Gly Asp Pro Glu
                130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175
```

<210> SEQ ID NO 22
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Asp Thr Ile Thr Leu Pro Cys Arg Pro Ala Pro Pro His Cys Ser
 1               5                  10                  15

Ser Asn Ile Thr Gly Leu Ile Leu Thr Arg Asp Gly Gly Asn Ser Asn
                 20                  25                  30

Asn Glu Ser Glu Ile Phe Arg Pro Gly Gly Gly Asp Met Arg Asp Ile
                 35                  40                  45

Ala Arg Cys Gln Ile Ala Gly Thr Val Val Ser Ser Gln Leu Phe Leu
     50                  55                  60

Asn Gly Ser Leu Ala Glu Glu Val Val Ile Arg Ser Val Asn Phe
 65                  70                  75                  80

Thr Asp Asn Ala Lys Ser Ile Cys Val Gln Leu Asn Thr Ser Val Glu
                     85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Asn Lys Thr Ile Ile Phe Lys Gln Ser Ser Gly Gly Asp Pro Glu
                130                 135                 140

Ile Val Thr His Trp Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175
```

<210> SEQ ID NO 23
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Ser Gln Leu Phe Leu
    50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
            85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
            115                 120                 125

Asn Asn Lys Thr Ile Ile Phe Lys Gln Ser Ser Gly Gly Asp Pro Glu
            130                 135                 140

Ile Val Thr His Trp Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 24
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asp Glu Ser Glu Ile Phe Arg Pro Gly Gly Gly Asp Met Arg Asp Ile
        35                  40                  45

Ala Arg Cys Gln Ile Ala Gly Thr Val Val Ser Ser Gln Leu Phe Leu
    50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
            85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
            115                 120                 125

Asn Asn Lys Thr Ile Ile Phe Lys Gln Ser Ser Gly Gly Asp Pro Glu
            130                 135                 140

Ile Val Thr His Trp Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 25
```

```
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Thr Ser Asp
                20                  25                  30

Asp Lys Thr Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Glu Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Lys Thr Ile Ile Phe Lys Gln Ser Ser Gly Gly Asp Pro Glu Phe
        130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp Ser
                165                 170

<210> SEQ ID NO 26
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Gly Ile Ser Asp
                20                  25                  30

Asp Lys Thr Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Glu Asp Phe
65                  70                  75                  80

Arg Asp Asn Ser Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Lys Thr Ile Ile Phe Ser Gln Ser Leu Gly Gly Asp Pro Glu Phe
        130                 135                 140
```

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp Ser
            165                 170

<210> SEQ ID NO 27
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Gly Ile Ser Asp
                20                  25                  30

Asp Lys Thr Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Glu Val Val Ile Arg Ser Glu Asn Phe
65                  70                  75                  80

Thr Asp Asn Ser Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Lys Thr Ile Ile Phe Ser Gln Ser Leu Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp Ser
            165                 170

<210> SEQ ID NO 28
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Gly Ile Ser Asp
                20                  25                  30

Asp Lys Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Glu Val Val Ile Arg Ser Glu Asp Phe
65                  70                  75                  80

Arg Asp Asn Ser Lys Ser Ile Cys Val Gln Leu Asn Thr Ser Val Glu
                85                  90                  95

```
Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Lys Thr Ile Ile Phe Ser Gln Ser Leu Gly Gly Asp Pro Glu Phe
130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170

<210> SEQ ID NO 29
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Ile Ser Asp
            20                  25                  30

Asp Lys Thr Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
50                  55                  60

Asn Gly Ser Leu Ala Glu Glu Val Val Ile Arg Ser Glu Asp Phe
65                  70                  75                  80

Arg Asp Asn Ser Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Ser Gln Ser Leu Gly Gly Asp Pro Glu Phe
130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170

<210> SEQ ID NO 30
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Ile Ser Asp
            20                  25                  30

Asp Asp Thr Glu Ile Phe Arg Pro Ser Gly Gly Asp Met Arg Asp Ile
        35                  40                  45
```

Ala Arg Cys Gln Ile Ala Gly Thr Val Val Ser Thr Gln Leu Phe Leu
            50                  55                  60

Asn Gly Ser Leu Ala Glu Glu Val Val Ile Arg Ser Glu Asp Phe
 65                  70                  75                  80

Arg Asp Asn Ser Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Arg Thr Ile Ile Phe Ser Gln Ser Leu Gly Gly Asp Pro Glu Phe
            130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170

<210> SEQ ID NO 31
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Thr Ile Thr Leu Pro Cys Arg Pro Ala Pro Pro His Cys Ser
 1               5                  10                  15

Ser Asn Ile Thr Gly Leu Ile Leu Thr Arg Ala Gly Gly Ile Ser Asp
                20                  25                  30

Asp Asn Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
            50                  55                  60

Asn Gly Ser Leu Ala Glu Glu Val Val Ile Arg Ser Glu Asp Phe
 65                  70                  75                  80

Arg Asp Asn Ser Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Arg Thr Ile Ile Phe Ser Gln Ser Leu Gly Gly Asp Pro Glu Phe
            130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170

<210> SEQ ID NO 32
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Gly Ile Ser Asp
                20                  25                  30

Asp Asn Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Val Val Ile Arg Ser Glu Asp Phe
65                  70                  75                  80

Arg Asp Asn Ser Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Ser Gln Ser Leu Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170

<210> SEQ ID NO 33
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Gly Val Ser Asp
                20                  25                  30

Asp Asp Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
        50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Ser Gln Ser Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170
```

```
<210> SEQ ID NO 34
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Val Ser Asp
                20                  25                  30

Asp Asp Thr Glu Ile Phe Arg Pro Ala Gly Gly Asp Met Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Arg Thr Ile Ile Phe Ser Gln Ser Ser Gly Gly Asp Pro Glu Phe
        130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170

<210> SEQ ID NO 35
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Val Ser Asp
                20                  25                  30

Asp Asp Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Arg Thr Ile Ile Phe Ser Gln Ser Ser Gly Gly Asp Pro Glu Phe
```

```
                  130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp
                165                 170

<210> SEQ ID NO 36
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
                20                  25                  30

Asp Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
        50                  55                  60

Asn Gly Ser Leu Ala Glu Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 37
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asp Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
        50                  55                  60

Asn Gly Ser Leu Ala Glu Glu Glu Val Val Ile Arg Ser Val Asp Phe
65                  70                  75                  80

Arg Asp Asn Ala Lys Ser Ile Cys Val Gln Leu Asn Thr Ser Val Glu
```

85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Arg Thr Ile Ile Phe Lys Gln Ser Ser Gly Gly Asp Pro Glu Phe
        130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 38
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
            20                  25                  30

Asp Glu Ser Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Arg Thr Ile Ile Phe Lys Gln Ser Ser Gly Gly Asp Pro Glu Phe
        130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 39
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
            20                  25                  30

Asp Glu Thr Glu Ile Phe Arg Pro Gly Gly Gly Asp Met Arg Asp Ile

```
                35                  40                  45
Ala Arg Cys Gln Ile Ala Gly Thr Val Val Ser Thr Gln Leu Phe Leu
        50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Arg Thr Ile Ile Phe Lys Gln Ser Ser Gly Gly Asp Pro Glu Phe
        130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170
```

<210> SEQ ID NO 40
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
                20                  25                  30

Asp Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Arg Thr Ile Ile Phe Lys Gln Ser Ser Gly Gly Asp Pro Glu Phe
        130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170
```

<210> SEQ ID NO 41
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Asp Thr Ile Thr Leu Pro Cys Arg Pro Ala Pro Pro His Cys Ser
1               5                   10                  15
Ser Asn Ile Thr Gly Leu Ile Leu Thr Arg Asp Gly Val Ser Asn
            20                  25                  30
Asp Glu Thr Glu Ile Phe Arg Pro Ser Gly Gly Asp Met Arg Asp Ile
        35                  40                  45
Ala Arg Cys Gln Ile Ala Gly Thr Val Val Ser Thr Gln Leu Phe Leu
    50                  55                  60
Asn Gly Ser Leu Ala Glu Glu Val Val Ile Arg Ser Val Asp Phe
65                  70                  75                  80
Thr Asp Asn Ala Lys Ser Ile Cys Val Gln Leu Asn Thr Ser Val Glu
                85                  90                  95
Ile Asn Cys Thr Gly Ala Gly His Cys Asn Ile Ser Arg Ala Lys Trp
            100                 105                 110
Asn Asn Thr Leu Lys Gln Ile Ala Ser Lys Leu Arg Glu Gln Phe Gly
        115                 120                 125
Asn Arg Thr Ile Ile Phe Lys Gln Ser Ser Gly Gly Asp Pro Glu Phe
    130                 135                 140
Val Thr His Ser Phe Asn Cys Gly Gly Glu Phe Phe Tyr Cys Asp Ser
145                 150                 155                 160
Thr Gln Leu Phe Asn Ser Thr Trp Phe Asn Ser Thr
                165                 170
```

<210> SEQ ID NO 42
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Asp Thr Ile Thr Leu Pro Cys Arg Pro Ala Pro Pro His Cys Ser
1               5                   10                  15
Ser Asn Ile Thr Gly Leu Ile Leu Thr Arg Asp Gly Val Ser Asn
            20                  25                  30
Asp Glu Thr Glu Ile Phe Arg Pro Ser Gly Gly Asp Met Arg Asp Ile
        35                  40                  45
Ala Arg Cys Gln Ile Ala Gly Thr Val Val Ser Thr Gln Leu Phe Leu
    50                  55                  60
Asn Gly Ser Leu Ala Glu Glu Val Val Ile Arg Ser Val Asp Phe
65                  70                  75                  80
Arg Asp Asn Ala Lys Ser Ile Cys Val Gln Leu Asn Thr Ser Val Glu
                85                  90                  95
Ile Asn Cys Thr Gly Ala Gly His Cys Asn Ile Ser Arg Ala Lys Trp
            100                 105                 110
Asn Asn Thr Leu Lys Gln Ile Ala Ser Lys Leu Arg Glu Gln Phe Gly
        115                 120                 125
Asn Lys Thr Ile Ile Phe Lys Gln Ser Ser Gly Gly Asp Pro Glu Phe
    130                 135                 140
Val Thr His Ser Phe Asn Cys Gly Gly Glu Phe Phe Tyr Cys Asp Ser
145                 150                 155                 160
Thr Gln Leu Phe Asn Ser Thr Trp Phe Asn Ser Thr
                165                 170
```

```
<210> SEQ ID NO 43
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Thr Ile Thr Leu Pro Cys Arg Pro Ala Pro Pro His Cys Ser
1               5                  10                  15

Ser Asn Ile Thr Gly Leu Ile Leu Thr Arg Asp Gly Val Ser Asn
            20                  25                  30

Asp Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Ile
    130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 44
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Thr Ile Thr Leu Pro Cys Arg Pro Ala Pro Pro His Cys Ser
1               5                  10                  15

Ser Asn Ile Thr Gly Leu Ile Leu Thr Arg Asp Gly Val Ser Asn
            20                  25                  30

Asp Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asp Thr Ser Val Glu
                85                  90                  95

Ile Asp Cys Thr Gly Ala Gly His Cys Asp Ile Ser Arg Ala Lys Trp
            100                 105                 110

Asp Asn Thr Leu Lys Gln Ile Ala Ser Lys Leu Arg Glu Gln Phe Gly
        115                 120                 125
```

Asp Arg Thr Ile Ile Phe Lys Gln Ser Ser Gly Gly Asp Pro Glu Phe
130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr
                165                 170

<210> SEQ ID NO 45
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
                20                  25                  30

Asn Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
        50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 46
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asn Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
        50                  55                  60

Asn Gly Ser Leu Ala Glu Glu Val Val Ile Arg Ser Val Asp Phe
65                  70                  75                  80

```
Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
            165                 170
```

<210> SEQ ID NO 47
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
            20                  25                  30

Asn Glu Ser Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
            165                 170
```

<210> SEQ ID NO 48
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
            20                  25                  30
```

Asn Glu Thr Glu Ile Phe Arg Pro Gly Gly Asp Met Arg Asp Ile
                35                  40                  45

Ala Arg Cys Gln Ile Ala Gly Thr Val Val Ser Thr Gln Leu Phe Leu
 50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Arg Thr Ile Ile Phe Lys Gln Ser Ser Gly Gly Asp Pro Glu Phe
130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 49
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
                20                  25                  30

Asn Glu Thr Glu Ile Phe Arg Pro Ser Gly Gly Asp Met Arg Asp Ile
                35                  40                  45

Ala Arg Cys Gln Ile Ala Gly Thr Val Val Ser Thr Gln Leu Leu Leu
 50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Arg Thr Ile Ile Phe Lys Gln Ser Ser Gly Gly Asp Pro Glu Phe
130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 50
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Thr Ile Thr Leu Pro Cys Arg Pro Ala Pro Pro His Cys Ser
1               5                  10                  15

Ser Asn Ile Thr Gly Leu Ile Leu Thr Arg Asp Gly Val Ser Asn
            20                  25                  30

Asn Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 51
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Thr Ile Thr Leu Pro Cys Arg Pro Ala Pro Pro His Cys Ser
1               5                  10                  15

Ser Asn Ile Thr Gly Leu Ile Leu Thr Arg Asp Gly Val Ser Asn
            20                  25                  30

Asn Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Lys Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 52
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Val Ser Asn
            20                  25                  30

Asn Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Ile
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170
```

<210> SEQ ID NO 53
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Val Ser Asn
            20                  25                  30

Asn Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125
```

```
Asn Arg Thr Ile Ile Phe Lys Gln Ser Ser Gly Gly Asp Pro Glu Phe
        130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 54
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Thr Ile Thr Leu Pro Cys Arg Pro Ala Pro Pro His Cys Ser
1               5                   10                  15

Ser Asn Ile Thr Gly Leu Ile Leu Thr Arg Ala Gly Gly Val Ser Asp
            20                  25                  30

Asn Asn Thr Glu Ile Phe Phe Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Ser Gln Ser Thr Gly Gly Asp Pro Glu Phe
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 55
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Thr Ile Thr Leu Pro Cys Arg Pro Ala Pro Pro His Cys Ser
1               5                   10                  15

Ser Asn Ile Thr Gly Leu Ile Leu Gly Arg Ala Gly Gly Ala Ser Asp
            20                  25                  30

Asp Asn Thr Glu Ile Phe Tyr Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80
```

-continued

```
Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Ser Gln Ser Thr Gly Gly Asp Pro Glu Ile
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr Trp
                165                 170
```

<210> SEQ ID NO 56
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Asp Thr Ile Thr Leu Pro Cys Arg Pro Ala Pro Pro His Cys Ser
1               5                   10                  15

Ser Asn Ile Thr Gly Leu Ile Leu Thr Arg Ala Gly Val Ser Asn
                20                  25                  30

Asn Glu Thr Glu Ile Phe Phe Pro Ser Gly Gly Asp Met Arg Asp Ile
            35                  40                  45

Ala Arg Cys Gln Ile Ala Gly Thr Val Val Ser Thr Gln Leu Phe Leu
        50                  55                  60

Asn Gly Ser Leu Ala Glu Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170
```

<210> SEQ ID NO 57
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Val Trp Lys Glu Ala Thr Thr Thr Leu Phe Cys Ala Ser Asp Ala Lys
1               5                   10                  15

Ala Tyr Asp Thr Glu Val His Asn Val Trp Ala Thr His Ala Cys Val
                20                  25                  30
```

Pro Thr Asp Pro Asn Pro Gln Glu Val Glu Leu Glu Asn Val Thr Glu
         35                  40                  45

Asn Phe Asn Met Trp Lys Asn Met Val Glu Gln Met His Glu Asp
 50                  55                  60

Ile Ile Ser Leu Trp Asp Gln Ser Leu Lys Pro Cys Val Lys Leu Thr
 65                  70                  75                  80

Gly Gly Ser Val Ile Thr Gln Ala Cys Pro Lys Ile Ser Phe Glu Pro
                 85                  90                  95

Ile Pro Ile His Tyr Cys Ala Pro Ala Gly Phe Ala Ile Leu Lys Cys
            100                 105                 110

Lys Asp Lys Lys Phe Asn Gly Lys Gly Pro Cys Ser Asn Val Ser Thr
        115                 120                 125

Val Gln Cys Thr His Gly Ile Arg Pro Val Val Ser Thr Gln Leu Leu
    130                 135                 140

Leu Asn Gly Ser Leu Ala Glu Glu Val Val Ile Arg Ser Glu Asn
145                 150                 155                 160

Phe Ala Asp Asn Ala Lys Thr Ile Ile Val Gln Leu Asn Glu Ser Val
                165                 170                 175

Glu Ile Asn Cys Thr Arg Pro Asn Asn Gly Ser Gly Ser Gly Gly
            180                 185                 190

Asp Ile Arg Gln Ala His Cys Asn Leu Ser Arg Ala Lys Trp Asn Asp
        195                 200                 205

Thr Leu Asn Lys Ile Val Ile Lys Leu Arg Glu Gln Phe Gly Asn Lys
    210                 215                 220

Thr Ile Val Phe Lys His Ser Ser Gly Gly Asp Pro Glu Ile Val Thr
225                 230                 235                 240

His Ser Phe Asn Cys Gly Gly Glu Phe Phe Tyr Cys Asn Ser Thr Gln
                245                 250                 255

Leu Phe Asn Ser Thr Trp Asn Val Thr Glu Glu Ser Asn Asn Thr Val
            260                 265                 270

Glu Asn Asn Thr Ile Thr Leu Pro Cys Arg Ile Lys Gln Ile Ile Asn
        275                 280                 285

Met Trp Gln Lys Val Gly Arg Ala Met Tyr Ala Pro Pro Ile Arg Gly
    290                 295                 300

Gln Ile Arg Cys Ser Ser Asn Ile Thr Gly Leu Leu Leu Thr Arg Asp
305                 310                 315                 320

Gly Gly Pro Glu Asp Asn Lys Thr Glu Val Phe Arg Pro Gly Gly Gly
                325                 330                 335

Asp Met Arg Asp Asn Trp Arg Ser Glu Leu Tyr Lys Tyr Lys Val Val
            340                 345                 350

Lys Ile Glu
        355

<210> SEQ ID NO 58
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Val Trp Lys Asp Ala Thr Thr Thr Leu Phe Cys Ala Ser Asp Ala Lys
1               5                   10                  15

Ala His Glu Thr Glu Val His Asn Val Trp Ala Thr His Ala Cys Val

```
                    20                  25                  30

Pro Thr Asp Pro Asn Pro Gln Glu Val Glu Leu Lys Asn Val Thr Glu
            35                  40                  45

Asn Phe Asn Met Trp Lys Asn Met Val Glu Gln Met His Glu Asp
 50                  55                  60

Ile Ile Ser Leu Trp Asp Gln Ser Leu Lys Pro Cys Val Lys Leu Thr
 65                  70                  75                  80

Gly Gly Ser Val Ile Thr Gln Ala Cys Pro Lys Val Ser Phe Glu Pro
                85                  90                  95

Ile Pro Ile His Tyr Cys Ala Pro Ala Gly Phe Ala Ile Leu Lys Cys
            100                 105                 110

Lys Asp Lys Lys Phe Asn Gly Lys Gly Pro Cys Ser Asn Val Ser Thr
        115                 120                 125

Val Gln Cys Thr His Gly Ile Arg Pro Val Val Ser Thr Gln Leu Leu
    130                 135                 140

Leu Asn Gly Ser Leu Ala Glu Glu Val Val Ile Arg Ser Glu Asp
145                 150                 155                 160

Phe Arg Asn Asn Ala Lys Ile Ile Ile Val Gln Leu Asn Glu Ser Val
                165                 170                 175

Glu Ile Asn Cys Thr Gly Ala Gly His Cys Asn Leu Ser Arg Ala Lys
            180                 185                 190

Trp Asn Asp Thr Leu Asn Lys Ile Val Ile Lys Leu Arg Glu Gln Phe
        195                 200                 205

Gly Asn Lys Thr Ile Val Phe Lys His Ser Ser Gly Gly Asp Pro Glu
    210                 215                 220

Ile Val Thr His Ser Phe Asn Cys Gly Gly Glu Phe Phe Tyr Cys Asn
225                 230                 235                 240

Ser Thr Gln Leu Phe Asn Ser Thr Trp Asn Val Thr Glu Glu Ser Asn
                245                 250                 255

Asn Thr Val Glu Asn Asn Thr Ile Thr Leu Pro Cys Arg Ile Lys Gln
            260                 265                 270

Ile Ile Asn Met Trp Gln Glu Val Gly Arg Ala Met Tyr Ala Pro Pro
        275                 280                 285

Ile Arg Gly Gln Ile Arg Cys Ser Ser Asn Ile Thr Gly Leu Leu Leu
    290                 295                 300

Ile Arg Asp Gly Gly Pro Glu Asp Asn Lys Thr Glu Ile Phe Arg Pro
305                 310                 315                 320

Gly Gly Gly Asp Met Arg Asp Asn Trp Arg Ser Glu Leu Tyr Lys Tyr
                325                 330                 335

Lys Val Val Lys Ile Glu
            340

<210> SEQ ID NO 59
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Val Trp Lys Asp Ala Thr Thr Thr Leu Phe Cys Ala Ser Asp Ala Lys
 1               5                  10                  15

Ala His Glu Thr Glu Val His Asn Val Trp Ala Thr His Ala Cys Val
            20                  25                  30
```

```
Pro Thr Asp Pro Asn Pro Gln Glu Val Glu Leu Lys Asn Val Thr Glu
         35                  40                  45
Asn Phe Asn Met Trp Lys Asn Met Val Glu Gln Met His Glu Asp
 50                  55                  60
Ile Ile Ser Leu Trp Asp Gln Ser Leu Lys Pro Cys Val Lys Leu Thr
 65                  70                  75                  80
Gly Gly Ser Val Ile Thr Gln Ala Cys Pro Lys Val Ser Phe Glu Pro
             85                  90                  95
Ile Pro Ile His Tyr Cys Ala Pro Ala Gly Phe Ala Ile Leu Lys Cys
            100                 105                 110
Lys Asp Lys Lys Phe Asn Gly Lys Gly Pro Cys Ser Asn Val Ser Thr
            115                 120                 125
Val Gln Cys Thr His Gly Ile Arg Pro Val Val Ser Thr Gln Leu Leu
130                 135                 140
Leu Asn Gly Ser Leu Ala Glu Glu Val Val Ile Arg Ser Glu Asp
145                 150                 155                 160
Phe Arg Asn Asn Ala Lys Ile Ile Ile Val Gln Leu Asn Glu Ser Val
                165                 170                 175
Glu Ile Asn Cys Thr Gly Ala Gly His Cys Asn Leu Ser Arg Ala Lys
            180                 185                 190
Trp Asn Asp Thr Leu Asn Lys Ile Val Ile Lys Leu Arg Glu Gln Phe
            195                 200                 205
Gly Asn Lys Thr Ile Val Phe Ser His Ser Ser Gly Gly Asp Pro Glu
            210                 215                 220
Phe Val Thr His Ser Phe Asn Cys Gly Gly Glu Phe Phe Tyr Cys Asn
225                 230                 235                 240
Ser Thr Gln Leu Phe Asn Ser Thr Trp Asn Val Thr Glu Glu Ser Asn
                245                 250                 255
Asn Thr Val Glu Asn Asn Thr Ile Thr Leu Pro Cys Arg Ile Lys Gln
                260                 265                 270
Ile Ile Asn Met Trp Gln Glu Val Gly Pro Ile Arg Gly Gln Ile Arg
            275                 280                 285
Cys Ser Ser Asn Ile Thr Gly Leu Leu Leu Ile Arg Asp Gly Gly Ala
290                 295                 300
Glu Asp Asn Lys Thr Glu Ile Phe Arg Pro Gly Gly Gly Asp Met Arg
305                 310                 315                 320
Asp Asn Trp Arg Ser Glu Leu Tyr Lys Tyr Lys Val Val Lys Ile Glu
                325                 330                 335

<210> SEQ ID NO 60
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Arg Val Lys Glu Lys Tyr Gln His Leu Trp Arg Trp Gly Trp Arg
1               5                  10                  15
Trp Gly Thr Met Leu Leu Gly Met Leu Met Ile Cys Ser Ala Thr Glu
                20                  25                  30
Lys Leu Trp Val Thr Val Tyr Tyr Gly Val Pro Val Trp Lys Glu Ala
            35                  40                  45
Thr Thr Thr Leu Phe Cys Ala Ser Asp Ala Lys Ala Tyr Asp Thr Glu
 50                  55                  60
```

```
Val His Asn Val Trp Ala Thr His Ala Cys Val Pro Thr Asp Pro Asn
 65                  70                  75                  80

Pro Gln Glu Val Glu Leu Glu Asn Val Thr Glu Asn Phe Asn Met Trp
             85                  90                  95

Lys Asn Asn Met Val Glu Gln Met His Glu Asp Ile Ile Ser Leu Trp
            100                 105                 110

Asp Gln Ser Leu Lys Pro Cys Val Lys Leu Thr Pro Leu Cys Val Thr
        115                 120                 125

Leu Asn Cys Thr Asp Leu Arg Asn Ala Thr Asn Gly Asn Asp Thr Asn
130                 135                 140

Thr Thr Ser Ser Ser Arg Glu Met Met Gly Gly Glu Met Lys Asn
145                 150                 155                 160

Cys Ser Phe Lys Ile Thr Thr Asn Ile Arg Gly Lys Val Gln Lys Glu
                165                 170                 175

Tyr Ala Leu Phe Tyr Glu Leu Asp Ile Val Pro Ile Asp Asn Asn Ser
            180                 185                 190

Asn Asn Arg Tyr Arg Leu Ile Ser Cys Asn Thr Ser Val Ile Thr Gln
        195                 200                 205

Ala Cys Pro Lys Ile Ser Phe Glu Pro Ile Pro Ile His Tyr Cys Ala
210                 215                 220

Pro Ala Gly Phe Ala Ile Leu Lys Cys Lys Asp Lys Lys Phe Asn Gly
225                 230                 235                 240

Lys Gly Pro Cys Ser Asn Val Ser Thr Val Gln Cys Thr His Gly Ile
                245                 250                 255

Arg Pro Val Val Ser Thr Gln Leu Leu Asn Gly Ser Leu Ala Glu
            260                 265                 270

Glu Glu Val Val Ile Arg Ser Glu Asn Phe Ala Asp Asn Ala Lys Thr
        275                 280                 285

Ile Ile Val Gln Leu Asn Glu Ser Val Glu Ile Asn Cys Thr Arg Pro
290                 295                 300

Asn Asn Asn Thr Arg Lys Ser Ile His Ile Gly Pro Gly Arg Ala Leu
305                 310                 315                 320

Tyr Thr Thr Gly Glu Ile Ile Gly Asp Ile Arg Gln Ala His Cys Asn
                325                 330                 335

Leu Ser Arg Ala Lys Trp Asn Asp Thr Leu Asn Lys Ile Val Ile Lys
            340                 345                 350

Leu Arg Glu Gln Phe Gly Asn Lys Thr Ile Val Phe Lys His Ser Ser
        355                 360                 365

Gly Gly Asp Pro Glu Ile Val Thr His Ser Phe Asn Cys Gly Gly Glu
370                 375                 380

Phe Phe Tyr Cys Asn Ser Thr Gln Leu Phe Asn Ser Thr Trp Asn Val
385                 390                 395                 400

Thr Glu Glu Ser Asn Asn Thr Val Glu Asn Asn Thr Ile Thr Leu Pro
                405                 410                 415

Cys Arg Ile Lys Gln Ile Ile Asn Met Trp Gln Lys Val Gly Arg Ala
            420                 425                 430

Met Tyr Ala Pro Pro Ile Arg Gly Gln Ile Arg Cys Ser Ser Asn Ile
        435                 440                 445

Thr Gly Leu Leu Leu Thr Arg Asp Gly Gly Pro Glu Asp Asn Lys Thr
450                 455                 460

Glu Val Phe Arg Pro Gly Gly Gly Asp Met Arg Asp Asn Trp Arg Ser
465                 470                 475                 480
```

Glu Leu Tyr Lys Tyr Lys Val Val Lys Ile Glu Pro Leu Gly Val Ala
            485                 490                 495

Pro Thr Lys Ala Lys Arg Arg Val Val Gln
            500                 505

<210> SEQ ID NO 61
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Thr Ile Thr Leu Pro Cys Arg Pro Ala Pro Pro His Cys Ser
1               5                   10                  15

Ser Asn Ile Thr Gly Leu Ile Leu Thr Arg Leu Gly Gly Val Ser Asn
            20                  25                  30

Asp Glu Thr Glu Ile Phe Lys Pro Ser Gly Gly Asp Trp Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 62
<211> LENGTH: 16
<212> TYPE: PRT
<213> ORGANISM: Human immunodeficiency virus

<400> SEQUENCE: 62

Arg Pro Asn Asn Gly Gly Ser Gly Ser Gly Gly Asp Ile Arg Gln Ala
1               5                   10                  15

<210> SEQ ID NO 63
<211> LENGTH: 6
<212> TYPE: PRT
<213> ORGANISM: Human immunodeficiency virus

<400> SEQUENCE: 63

Arg Ala Met Tyr Ala Pro
1               5

<210> SEQ ID NO 64
<211> LENGTH: 175
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Asn Ser Asn
            20                  25                  30

Asn Glu Ser Glu Ile Phe Arg Pro Gly Gly Gly Asp Met Arg Asp Ile
        35                  40                  45

Ala Asn Cys Ser Ile Ala Gly Thr Val Val Ser Thr Gln Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
            165                 170                 175

<210> SEQ ID NO 65
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Asn Ala Ser Thr Val Val Ser Thr Gln Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser

-continued 165                 170                 175

<210> SEQ ID NO 66
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Asn Val Thr Ser Thr Gln Leu Leu Leu
    50                  55                  60

Asn Gly Ser Leu Ala Glu Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 67
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
    50                  55                  60

Asn Gly Ser Leu Ala Glu Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Asn Phe Ser

```
                    115                 120                 125
Asn Asn Lys Thr Ile Ile Phe Lys Gln Ser Ser Gly Gly Asp Pro Glu
            130                 135                 140
Ile Val Thr His Ser Phe Asn Cys Gly Gly Glu Phe Phe Tyr Cys Asn
145                 150                 155                 160
Ser Thr Gln Leu Phe Asn Ser Thr Trp Phe Asn Ser Thr Trp Ser
                165                 170                 175

<210> SEQ ID NO 68
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Thr Ile Thr Leu Pro Cys Asn Pro Ser Pro Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 69
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Thr Ile Thr Leu Pro Cys Arg Asn Ala Thr Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Glu Val Val Ile Arg Ser Val Asn Phe
```

```
65                  70                  75                  80
Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 70
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Asn Glu Thr Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 71
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Thr Ile Thr Leu Pro Cys Asn Pro Ser Pro Pro His Cys Ser
1               5                   10                  15

Ser Asn Ile Thr Gly Leu Ile Leu Thr Arg Asp Gly Gly Asn Ser Asn
```

```
            20                  25                  30
Asn Glu Ser Glu Ile Phe Arg Pro Gly Gly Gly Asp Met Arg Asp Ile
        35                  40                  45

Ala Arg Cys Gln Asn Ala Ser Thr Val Val Ser Thr Gln Leu Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Asn Glu Thr Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 72
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Thr Ile Thr Leu Pro Cys Asn Pro Ser Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Asn Cys Ser Ile Ala Gly Thr Val Val Ser Thr Gln Leu Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Asn Glu Thr Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 73
<211> LENGTH: 175
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 73

Asp Thr Ile Thr Leu Pro Cys Asn Pro Ser Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Asn Cys Ser Ile Ala Gly Asn Val Thr Thr Gln Leu Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Asn Glu Thr Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 74
<211> LENGTH: 175
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 74

Asp Thr Ile Thr Leu Pro Cys Asn Pro Ser Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Asn Cys Ser Ile Ala Gly Thr Val Val Ser Thr Gln Leu Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Asn Phe Ser
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Asn Glu Thr Phe Tyr Cys Asn
145                 150                 155                 160

```
Ser Thr Gln Leu Phe Asn Ser Thr Trp Phe Asn Ser Thr Trp Ser
                165                 170                 175

<210> SEQ ID NO 75
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Thr Ile Thr Leu Pro Cys Asn Pro Ser Pro Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Gly Asp Met Arg Asp Ile
                35                  40                  45

Ala Asn Cys Ser Ile Ala Gly Asn Val Thr Ser Thr Gln Leu Leu Leu
                50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Asn Phe Ser
                115                 120                 125

Asn Asn Lys Thr Ile Ile Phe Lys Gln Ser Ser Gly Gly Asp Pro Glu
                130                 135                 140

Ile Val Thr His Ser Phe Asn Cys Gly Asn Glu Thr Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 76
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
                20                  25                  30

Arg Gly Gly Ser Gly Gly Ser Gly Gly Asp Thr Ile Thr Leu Pro Cys
                35                  40                  45

Arg Pro Ala Pro Pro His Cys Ser Ser Asn Ile Thr Gly Leu Ile
                50                  55                  60

Leu Thr Arg Asp Gly Gly Asn Ser Asn Asp Glu Ser Glu Ile Phe Arg
65                  70                  75                  80

Pro Gly Gly Gly Asp Met Arg Asp Ile Ala Arg Cys Gln Ile Ala Gly
                85                  90                  95

Thr Val Val Ser Thr Gln Leu Leu Leu Asn Gly Ser Leu Ala Glu Glu
                100                 105                 110
```

```
Glu Val Val Ile Arg Ser Val Asp Phe Thr Asp Asn Ala Lys Ser Ile
            115                 120                 125

Cys Val Gln Leu Asn Thr Ser Val Glu Ile Asn Cys Thr Gly Ala Gly
130                 135                 140

His Cys Asn Ile Ser Arg Ala Lys Trp Asn Asn Thr Leu Lys Gln Ile
145                 150                 155                 160

Ala Ser Lys Leu Arg Glu Gln Phe Gly Asn Asn Lys Thr Ile Ile Phe
                165                 170                 175

Lys Gln Ser Ser Gly Gly Asp Pro Glu Ile Val Thr His Ser Phe Asn
            180                 185                 190

Cys Gly Gly Glu Phe Phe Tyr Cys Asn Ser Thr Gln Leu Phe Asn Ser
        195                 200                 205

Thr Trp Phe Asn Ser Thr Trp Ser
    210                 215

<210> SEQ ID NO 77
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asp Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser Gly
                165                 170                 175

Gly Ser Gly Gly Ser Gly Gly Arg Met Lys Gln Ile Glu Asp Lys Ile
            180                 185                 190

Glu Glu Ile Leu Ser Lys Ile Tyr His Ile Glu Asn Glu Ile Ala Arg
        195                 200                 205

Ile Lys Lys Leu Ile Gly Glu Arg
    210                 215

<210> SEQ ID NO 78
<211> LENGTH: 216
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 78

Arg Met Lys Gln Ile Glu Asp Lys Leu Glu Glu Ile Leu Ser Lys Leu
1               5                   10                  15

Tyr His Ile Glu Asn Glu Leu Ala Arg Ile Lys Lys Leu Leu Gly Glu
            20                  25                  30

Arg Gly Gly Ser Gly Gly Ser Gly Gly Asp Thr Ile Thr Leu Pro Cys
        35                  40                  45

Arg Pro Ala Pro Pro Pro His Cys Ser Ser Asn Ile Thr Gly Leu Ile
50                  55                  60

Leu Thr Arg Asp Gly Gly Asn Ser Asn Asp Glu Ser Glu Ile Phe Arg
65                  70                  75                  80

Pro Gly Gly Gly Asp Met Arg Asp Ile Ala Arg Cys Gln Ile Ala Gly
                85                  90                  95

Thr Val Val Ser Thr Gln Leu Leu Leu Asn Gly Ser Leu Ala Glu Glu
            100                 105                 110

Glu Val Val Ile Arg Ser Val Asp Phe Thr Asp Asn Ala Lys Ser Ile
        115                 120                 125

Cys Val Gln Leu Asn Thr Ser Val Glu Ile Asn Cys Thr Gly Ala Gly
130                 135                 140

His Cys Asn Ile Ser Arg Ala Lys Trp Asn Asn Thr Leu Lys Gln Ile
145                 150                 155                 160

Ala Ser Lys Leu Arg Glu Gln Phe Gly Asn Asn Lys Thr Ile Ile Phe
                165                 170                 175

Lys Gln Ser Ser Gly Gly Asp Pro Glu Ile Val Thr His Ser Phe Asn
            180                 185                 190

Cys Gly Gly Glu Phe Phe Tyr Cys Asn Ser Thr Gln Leu Phe Asn Ser
        195                 200                 205

Thr Trp Phe Asn Ser Thr Trp Ser
    210                 215

<210> SEQ ID NO 79
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asp Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110
```

Asn Asn Thr Leu Lys Gln Ile Ala Ser Lys Leu Arg Glu Gln Phe Gly
            115                 120                 125

Asn Asn Lys Thr Ile Ile Phe Lys Gln Ser Ser Gly Gly Asp Pro Glu
        130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser Gly
                165                 170                 175

Gly Ser Gly Gly Ser Gly Gly Arg Met Lys Gln Ile Glu Asp Lys Leu
            180                 185                 190

Glu Glu Ile Leu Ser Lys Leu Tyr His Ile Glu Asn Glu Leu Ala Arg
            195                 200                 205

Ile Lys Lys Leu Leu Gly Glu Arg
            210                 215

<210> SEQ ID NO 80
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Lys Val Lys Gln Leu Glu Asp Val Val Glu Glu Leu Leu Ser Val
1               5                   10                  15

Asn Tyr His Leu Glu Asn Val Val Ala Arg Leu Lys Lys Leu Val Gly
            20                  25                  30

Glu Arg Ser Gly Gly Ser Gly Gly Ser Gly Gly Gly Asp Thr Ile Thr
        35                  40                  45

Leu Pro Cys Arg Pro Ala Pro Pro His Cys Ser Ser Asn Ile Thr
50                  55                  60

Gly Leu Ile Leu Thr Arg Asp Gly Gly Asn Ser Asn Asp Glu Ser Glu
65                  70                  75                  80

Ile Phe Arg Pro Gly Gly Gly Asp Met Arg Asp Ile Ala Arg Cys Gln
                85                  90                  95

Ile Ala Gly Thr Val Val Ser Thr Gln Leu Leu Leu Asn Gly Ser Leu
            100                 105                 110

Ala Glu Glu Glu Val Val Ile Arg Ser Val Asp Phe Thr Asp Asn Ala
            115                 120                 125

Lys Ser Ile Cys Val Gln Leu Asn Thr Ser Val Glu Ile Asn Cys Thr
130                 135                 140

Gly Ala Gly His Cys Asn Ile Ser Arg Ala Lys Trp Asn Asn Thr Leu
145                 150                 155                 160

Lys Gln Ile Ala Ser Lys Leu Arg Glu Gln Phe Gly Asn Asn Lys Thr
                165                 170                 175

Ile Ile Phe Lys Gln Ser Ser Gly Gly Asp Pro Glu Ile Val Thr His
            180                 185                 190

Ser Phe Asn Cys Gly Gly Glu Phe Phe Tyr Cys Asn Ser Thr Gln Leu
            195                 200                 205

Phe Asn Ser Thr Trp Phe Asn Ser Thr Trp Ser
            210                 215

<210> SEQ ID NO 81
<211> LENGTH: 221
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 81

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asp Glu Ser Glu Ile Phe Arg Pro Gly Gly Gly Asp Met Arg Asp Ile
                35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Asn Lys Thr Ile Ile Phe Lys Gln Ser Ser Gly Gly Asp Pro Glu
130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser Gly
                165                 170                 175

Gly Ser Gly Gly Ser Gly Gly Ser Gly Gly Gly Met Lys Val Lys Gln
            180                 185                 190

Leu Glu Asp Val Val Glu Glu Leu Leu Ser Val Asn Tyr His Leu Glu
                195                 200                 205

Asn Val Val Ala Arg Leu Lys Lys Leu Val Gly Glu Arg
210                 215                 220

<210> SEQ ID NO 82
<211> LENGTH: 407
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asp Glu Ser Glu Ile Phe Arg Pro Gly Gly Gly Asp Met Arg Asp Ile
                35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
```

```
                 100                 105                 110
Asn Asn Thr Leu Lys Gln Ile Ala Ser Lys Leu Arg Glu Gln Phe Gly
            115                 120                 125
Asn Asn Lys Thr Ile Ile Phe Lys Gln Ser Ser Gly Gly Asp Pro Glu
        130                 135                 140
Ile Val Thr His Ser Phe Asn Cys Gly Gly Glu Phe Phe Tyr Cys Asn
145                 150                 155                 160
Ser Thr Gln Leu Phe Asn Ser Thr Trp Phe Asn Ser Thr Trp Ser Gly
                165                 170                 175
Gly Ser Gly Gly Ser Gly Gly Ser Gly Gly Arg Met Lys Gln Ile
            180                 185                 190
Glu Asp Lys Leu Glu Glu Ile Leu Ser Lys Leu Tyr His Ile Glu Asn
        195                 200                 205
Glu Leu Ala Arg Ile Lys Lys Leu Leu Gly Glu Arg Gly Gly Ser Gly
    210                 215                 220
Gly Ser Gly Gly Ser Gly Gly Gly Asp Thr Ile Thr Leu Pro Cys Arg
225                 230                 235                 240
Pro Ala Pro Pro His Cys Ser Ser Asn Ile Thr Gly Leu Ile Leu
                245                 250                 255
Thr Arg Asp Gly Gly Asn Ser Asn Asp Glu Ser Glu Ile Phe Arg Pro
            260                 265                 270
Gly Gly Gly Asp Met Arg Asp Ile Ala Arg Cys Gln Ile Ala Gly Thr
        275                 280                 285
Val Val Ser Thr Gln Leu Leu Leu Asn Gly Ser Leu Ala Glu Glu Glu
    290                 295                 300
Val Val Ile Arg Ser Val Asp Phe Thr Asp Asn Ala Lys Ser Ile Cys
305                 310                 315                 320
Val Gln Leu Asn Thr Ser Val Glu Ile Asn Cys Thr Gly Ala Gly His
                325                 330                 335
Cys Asn Ile Ser Arg Ala Lys Trp Asn Asn Thr Leu Lys Gln Ile Ala
            340                 345                 350
Ser Lys Leu Arg Glu Gln Phe Gly Asn Asn Lys Thr Ile Ile Phe Lys
        355                 360                 365
Gln Ser Ser Gly Gly Asp Pro Glu Ile Val Thr His Ser Phe Asn Cys
    370                 375                 380
Gly Gly Glu Phe Phe Tyr Cys Asn Ser Thr Gln Leu Phe Asn Ser Thr
385                 390                 395                 400
Trp Phe Asn Ser Thr Trp Ser
            405
```

<210> SEQ ID NO 83
<211> LENGTH: 408
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

```
Asp Thr Ile Thr Leu Pro Cys Arg Pro Ala Pro Pro His Cys Ser
1               5                   10                  15
Ser Asn Ile Thr Gly Leu Ile Leu Thr Arg Asp Gly Gly Asn Ser Asn
            20                  25                  30
Asp Glu Ser Glu Ile Phe Arg Pro Gly Gly Gly Asp Met Arg Asp Ile
        35                  40                  45
```

```
Ala Arg Cys Gln Ile Ala Gly Thr Val Val Ser Thr Gln Leu Leu Leu
 50                  55                  60
Asn Gly Ser Leu Ala Glu Glu Val Val Ile Arg Ser Val Asp Phe
 65                  70                  75                  80
Thr Asp Asn Ala Lys Ser Ile Cys Val Gln Leu Asn Thr Ser Val Glu
                 85                  90                  95
Ile Asn Cys Thr Gly Ala Gly His Cys Asn Ile Ser Arg Ala Lys Trp
            100                 105                 110
Asn Asn Thr Leu Lys Gln Ile Ala Ser Lys Leu Arg Glu Gln Phe Gly
        115                 120                 125
Asn Asn Lys Thr Ile Ile Phe Lys Gln Ser Ser Gly Gly Asp Pro Glu
    130                 135                 140
Ile Val Thr His Ser Phe Asn Cys Gly Gly Glu Phe Phe Tyr Cys Asn
145                 150                 155                 160
Ser Thr Gln Leu Phe Asn Ser Thr Trp Phe Asn Ser Thr Trp Ser Gly
                165                 170                 175
Gly Ser Gly Gly Ser Gly Gly Ser Gly Gly Gly Met Lys Val Lys Gln
            180                 185                 190
Leu Glu Asp Val Val Glu Glu Leu Leu Ser Val Asn Tyr His Leu Glu
        195                 200                 205
Asn Val Val Ala Arg Leu Lys Lys Leu Val Gly Glu Arg Gly Gly Ser
    210                 215                 220
Gly Gly Ser Gly Gly Ser Gly Gly Asp Thr Ile Thr Leu Pro Cys
225                 230                 235                 240
Arg Pro Ala Pro Pro His Cys Ser Ser Asn Ile Thr Gly Leu Ile
                245                 250                 255
Leu Thr Arg Asp Gly Gly Asn Ser Asn Asp Glu Ser Glu Ile Phe Arg
            260                 265                 270
Pro Gly Gly Gly Asp Met Arg Asp Ile Ala Arg Cys Gln Ile Ala Gly
        275                 280                 285
Thr Val Val Ser Thr Gln Leu Leu Leu Asn Gly Ser Leu Ala Glu Glu
    290                 295                 300
Glu Val Val Ile Arg Ser Val Asp Phe Thr Asp Asn Ala Lys Ser Ile
305                 310                 315                 320
Cys Val Gln Leu Asn Thr Ser Val Glu Ile Asn Cys Thr Gly Ala Gly
                325                 330                 335
His Cys Asn Ile Ser Arg Ala Lys Trp Asn Asn Thr Leu Lys Gln Ile
            340                 345                 350
Ala Ser Lys Leu Arg Glu Gln Phe Gly Asn Asn Lys Thr Ile Ile Phe
        355                 360                 365
Lys Gln Ser Ser Gly Gly Asp Pro Glu Ile Val Thr His Ser Phe Asn
    370                 375                 380
Cys Gly Gly Glu Phe Phe Tyr Cys Asn Ser Thr Gln Leu Phe Asn Ser
385                 390                 395                 400
Thr Trp Phe Asn Ser Thr Trp Ser
                405
```

<210> SEQ ID NO 84
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Asn Ser Asn
            20                  25                  30

Asp Glu Ser Glu Ile Phe Arg Pro Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
        130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser Gly
                165                 170                 175

Gly Ser Gly Gly Ser Gly Gly Ser Gly Gly Ser Gly Gly Met Ser
            180                 185                 190

Gln Ala Ile Gly Ile Leu Glu Leu Thr Ser Ile Ala Ala Gly Met Glu
        195                 200                 205

Leu Gly Asp Ala Met Leu Lys Ser Ala Asn Val Asp Leu Leu Val Ser
210                 215                 220

Lys Thr Ile Ser Pro Gly Lys Phe Leu Leu Met Leu Gly Gly Asp Ile
225                 230                 235                 240

Gly Ala Ile Gln Gln Ala Ile Glu Thr Gly Thr Ser Gln Ala Gly Glu
                245                 250                 255

Leu Leu Val Asp Ser Leu Val Leu Ala Asn Ile His Pro Ser Val Leu
            260                 265                 270

Pro Ala Ile Ser Gly Leu Asn Ser Val Asp Lys Arg Gln Ala Val Gly
        275                 280                 285

Ile Val Glu Thr Trp Ser Val Ala Ala Ile Ser Ala Ala Asp Arg
        290                 295                 300

Ala Val Lys Gly Ser Asp Val Thr Leu Val Arg Val His Met Ala Phe
305                 310                 315                 320

Gly Ile Gly Gly Lys Ala Tyr Met Val Val Ala Gly Asp Val Ser Asp
                325                 330                 335

Val Ala Leu Ala Val Thr Val Ala Ser Ser Ala Gly Ala Tyr Gly
            340                 345                 350

Leu Leu Val Tyr Ala Ser Leu Ile Pro Arg Pro His Glu Ala Met Trp
        355                 360                 365

Arg Gln Met Val Glu Gly
    370

<210> SEQ ID NO 85
<211> LENGTH: 374
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 85

Met Ser Gln Ala Ile Gly Ile Leu Glu Leu Thr Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Pro Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Ile Ser Ala Ala
            100                 105                 110

Asp Arg Ala Val Lys Gly Ser Asp Val Thr Leu Val Arg Val His Met
        115                 120                 125

Ala Phe Gly Ile Gly Gly Lys Ala Tyr Met Val Val Ala Gly Asp Val
    130                 135                 140

Ser Asp Val Ala Leu Ala Val Thr Val Ala Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly Gly Ser Gly Gly Ser Gly Gly
            180                 185                 190

Ser Gly Gly Ser Gly Gly Asp Thr Ile Thr Leu Pro Cys Arg Pro
        195                 200                 205

Ala Pro Pro His Cys Ser Ser Asn Ile Thr Gly Leu Ile Leu Thr
    210                 215                 220

Arg Asp Gly Gly Asn Ser Asn Asp Glu Ser Glu Ile Phe Arg Pro Gly
225                 230                 235                 240

Gly Gly Asp Met Arg Asp Ile Ala Arg Cys Gln Ile Ala Gly Thr Val
                245                 250                 255

Val Ser Thr Gln Leu Leu Leu Asn Gly Ser Leu Ala Glu Glu Glu Val
            260                 265                 270

Val Ile Arg Ser Val Asp Phe Thr Asp Asn Ala Lys Ser Ile Cys Val
        275                 280                 285

Gln Leu Asn Thr Ser Val Glu Ile Asn Cys Thr Gly Ala Gly His Cys
    290                 295                 300

Asn Ile Ser Arg Ala Lys Trp Asn Asn Thr Leu Lys Gln Ile Ala Ser
305                 310                 315                 320

Lys Leu Arg Glu Gln Phe Gly Asn Asn Lys Thr Ile Ile Phe Lys Gln
                325                 330                 335

Ser Ser Gly Gly Asp Pro Glu Ile Val Thr His Ser Phe Asn Cys Gly
            340                 345                 350

Gly Glu Phe Phe Tyr Cys Asn Ser Thr Gln Leu Phe Asn Ser Thr Trp
        355                 360                 365

Phe Asn Ser Thr Trp Ser
    370

<210> SEQ ID NO 86

```
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Arg Glu Glu Asp Ile
        35                  40                  45

Thr Leu Val Arg Val Pro Gly Ser Trp Glu Ile Pro Val Ala Ala Gly
50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
130                 135                 140

Glu Met Ala Asn Leu Phe Lys Ser Leu Arg Gly Gly Ser Gly Ser
145                 150                 155                 160

Gly Gly Ser Gly Gly Ser Gly Gly Asp Thr Ile Thr Leu Pro Cys
                165                 170                 175

Arg Pro Ala Pro Pro His Cys Ser Ser Asn Ile Thr Gly Leu Ile
            180                 185                 190

Leu Thr Arg Asp Gly Gly Asn Ser Asn Asp Glu Ser Glu Ile Phe Arg
            195                 200                 205

Pro Gly Gly Gly Asp Met Arg Asp Ile Ala Arg Cys Gln Ile Ala Gly
210                 215                 220

Thr Val Val Ser Thr Gln Leu Leu Leu Asn Gly Ser Leu Ala Glu Glu
225                 230                 235                 240

Glu Val Val Ile Arg Ser Val Asp Phe Thr Asp Asn Ala Lys Ser Ile
                245                 250                 255

Cys Val Gln Leu Asn Thr Ser Val Glu Ile Asn Cys Thr Gly Ala Gly
            260                 265                 270

His Cys Asn Ile Ser Arg Ala Lys Trp Asn Asn Thr Leu Lys Gln Ile
        275                 280                 285

Ala Ser Lys Leu Arg Glu Gln Phe Gly Asn Asn Lys Thr Ile Ile Phe
290                 295                 300

Lys Gln Ser Ser Gly Gly Asp Pro Glu Ile Val Thr His Ser Phe Asn
305                 310                 315                 320

Cys Gly Gly Glu Phe Phe Tyr Cys Asn Ser Thr Gln Leu Phe Asn Ser
                325                 330                 335

Thr Trp Phe Asn Ser Thr Trp Ser
            340

<210> SEQ ID NO 87
<211> LENGTH: 344
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 87

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asp Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser Gly
                165                 170                 175

Gly Ser Gly Gly Ser Gly Gly Ser Gly Gly Ser Gly Gly Met Gln
            180                 185                 190

Ile Tyr Glu Gly Lys Leu Thr Ala Glu Gly Leu Arg Phe Gly Ile Val
        195                 200                 205

Ala Ser Arg Phe Asn His Ala Leu Val Asp Arg Leu Val Glu Gly Ala
210                 215                 220

Ile Asp Ala Ile Val Arg His Gly Gly Arg Glu Glu Asp Ile Thr Leu
225                 230                 235                 240

Val Arg Val Pro Gly Ser Trp Glu Ile Pro Val Ala Ala Gly Glu Leu
                245                 250                 255

Ala Arg Lys Glu Asp Ile Asp Ala Val Ile Ala Ile Gly Val Leu Ile
            260                 265                 270

Arg Gly Ala Thr Pro His Phe Asp Tyr Ile Ala Ser Glu Val Ser Lys
        275                 280                 285

Gly Leu Ala Asp Leu Ser Leu Glu Leu Arg Lys Pro Ile Thr Phe Gly
290                 295                 300

Val Ile Thr Ala Asp Thr Leu Glu Gln Ala Ile Glu Arg Ala Gly Thr
305                 310                 315                 320

Lys His Gly Asn Lys Gly Trp Glu Ala Ala Leu Ser Ala Ile Glu Met
                325                 330                 335

Ala Asn Leu Phe Lys Ser Leu Arg
            340
```

<210> SEQ ID NO 88
<211> LENGTH: 348
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 88

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg Gly Ser Gln Tyr Ile Lys
145                 150                 155                 160

Ala Asn Ser Lys Phe Ile Gly Ile Thr Glu Leu Ser Gly Asp Thr Ile
                165                 170                 175

Thr Leu Pro Cys Arg Pro Ala Pro Pro His Cys Ser Ser Asn Ile
            180                 185                 190

Thr Gly Leu Ile Leu Thr Arg Asp Gly Gly Asn Ser Asn Asp Glu Ser
            195                 200                 205

Glu Ile Phe Arg Pro Gly Gly Gly Asp Met Arg Asp Ile Ala Arg Cys
    210                 215                 220

Gln Ile Ala Gly Thr Val Val Ser Thr Gln Leu Leu Leu Asn Gly Ser
225                 230                 235                 240

Leu Ala Glu Glu Glu Val Val Ile Arg Ser Val Asp Phe Thr Asp Asn
                245                 250                 255

Ala Lys Ser Ile Cys Val Gln Leu Asn Thr Ser Val Glu Ile Asn Cys
            260                 265                 270

Thr Gly Ala Gly His Cys Asn Ile Ser Arg Ala Lys Trp Asn Asn Thr
        275                 280                 285

Leu Lys Gln Ile Ala Ser Lys Leu Arg Glu Gln Phe Gly Asn Asn Lys
    290                 295                 300

Thr Ile Ile Phe Lys Gln Ser Ser Gly Gly Asp Pro Glu Ile Val Thr
305                 310                 315                 320

His Ser Phe Asn Cys Gly Gly Glu Phe Phe Tyr Cys Asn Ser Thr Gln
                325                 330                 335

Leu Phe Asn Ser Thr Trp Phe Asn Ser Thr Trp Ser
            340                 345

<210> SEQ ID NO 89
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

| | | | | | | | | | | | | | | |
|---|---|---|---|---|---|---|---|---|---|---|---|---|---|---|
|Asp|Thr|Ile|Thr|Leu|Pro|Cys|Arg|Pro|Ala|Pro|Pro|His|Cys|Ser|
|1| | |  |5| | | | |10| | | | |15|
|Ser|Asn|Ile|Thr|Gly|Leu|Ile|Leu|Thr|Arg|Asp|Gly|Gly|Asn|Ser|Asn|
| | | |20| | | | |25| | | | |30| | |
|Asp|Glu|Ser|Glu|Ile|Phe|Arg|Pro|Gly|Gly|Gly|Asp|Met|Arg|Asp|Ile|
| | | |35| | | | |40| | | | |45| | |
|Ala|Arg|Cys|Gln|Ile|Ala|Gly|Thr|Val|Val|Ser|Thr|Gln|Leu|Leu|Leu|
| |50| | | | |55| | | | |60| | | | |
|Asn|Gly|Ser|Leu|Ala|Glu|Glu|Val|Val|Ile|Arg|Ser|Val|Asp|Phe|
|65| | | | |70| | | | |75| | | | |80|
|Thr|Asp|Asn|Ala|Lys|Ser|Ile|Cys|Val|Gln|Leu|Asn|Thr|Ser|Val|Glu|
| | | | |85| | | | |90| | | | |95| |
|Ile|Asn|Cys|Thr|Gly|Ala|Gly|His|Cys|Asn|Ile|Ser|Arg|Ala|Lys|Trp|
| | | |100| | | | |105| | | | |110| | |
|Asn|Asn|Thr|Leu|Lys|Gln|Ile|Ala|Ser|Lys|Leu|Arg|Glu|Gln|Phe|Gly|
| | | |115| | | | |120| | | | |125| | |
|Asn|Asn|Lys|Thr|Ile|Ile|Phe|Lys|Gln|Ser|Ser|Gly|Gly|Asp|Pro|Glu|
| | | |130| | | | |135| | | | |140| | |
|Ile|Val|Thr|His|Ser|Phe|Asn|Cys|Gly|Gly|Glu|Phe|Phe|Tyr|Cys|Asn|
|145| | | | |150| | | | |155| | | | |160|
|Ser|Thr|Gln|Leu|Phe|Asn|Ser|Thr|Trp|Phe|Asn|Ser|Thr|Trp|Ser|Gly|
| | | | |165| | | | |170| | | | |175| |
|Ser|Gln|Tyr|Ile|Lys|Ala|Asn|Ser|Lys|Phe|Ile|Gly|Ile|Thr|Glu|Leu|
| | | |180| | | | |185| | | | |190| | |
|Ser|Gly|Met|Gln|Ile|Tyr|Glu|Gly|Lys|Leu|Thr|Ala|Glu|Gly|Leu|Arg|
| | | |195| | | | |200| | | | |205| | |
|Phe|Gly|Ile|Val|Ala|Ser|Arg|Phe|Asn|His|Ala|Leu|Val|Asp|Arg|Leu|
| | | |210| | | | |215| | | | |220| | |
|Val|Glu|Gly|Ala|Ile|Asp|Ala|Ile|Val|Arg|His|Gly|Arg|Glu|Glu|
|225| | | | |230| | | | |235| | | | |240|
|Asp|Ile|Thr|Leu|Val|Arg|Val|Pro|Gly|Ser|Trp|Glu|Ile|Pro|Val|Ala|
| | | | |245| | | | |250| | | | |255| |
|Ala|Gly|Glu|Leu|Ala|Arg|Lys|Glu|Asp|Ile|Asp|Ala|Val|Ile|Ala|Ile|
| | | |260| | | | |265| | | | |270| | |
|Gly|Val|Leu|Ile|Arg|Gly|Ala|Thr|Pro|His|Phe|Asp|Tyr|Ile|Ala|Ser|
| | | |275| | | | |280| | | | |285| | |
|Glu|Val|Ser|Lys|Gly|Leu|Ala|Asp|Leu|Ser|Leu|Glu|Leu|Arg|Lys|Pro|
| | | |290| | | | |295| | | | |300| | |
|Ile|Thr|Phe|Gly|Val|Ile|Thr|Ala|Asp|Thr|Leu|Glu|Gln|Ala|Ile|Glu|
|305| | | | |310| | | | |315| | | | |320|
|Arg|Ala|Gly|Thr|Lys|His|Gly|Asn|Lys|Gly|Trp|Glu|Ala|Ala|Leu|Ser|
| | | |325| | | | |330| | | | |335| | |
|Ala|Ile|Glu|Met|Ala|Asn|Leu|Phe|Lys|Ser|Leu|Arg|
| | | |340| | | | |345| | | | |

<210> SEQ ID NO 90
<211> LENGTH: 426
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Val Glu Tyr Phe Glu Lys Leu Arg Ser Ala Leu Leu Asp Gly Val Asn
1               5                   10                  15

Lys Gly Arg Ser Leu Leu Lys His Leu Pro Val Thr Arg Ile Glu Gly
            20                  25                  30

Gln Ser Phe Arg Val Asp Ile Ile Lys Phe Glu Asp Gly Val Arg Val
        35                  40                  45

Val Lys Gln Glu Tyr Lys Pro Ile Pro Leu Lys Lys Lys Phe Tyr
50                  55                  60

Val Gly Ile Arg Glu Leu Asn Asp Gly Thr Tyr Asp Val Ser Ile Ala
65                  70                  75                  80

Thr Lys Ala Gly Glu Leu Leu Val Lys Asp Glu Glu Ser Leu Val Ile
                85                  90                  95

Arg Glu Ile Leu Ser Thr Glu Gly Ile Lys Lys Met Lys Leu Ser Ser
                100                 105                 110

Trp Asp Asn Pro Glu Glu Ala Leu Asn Asp Leu Met Asn Ala Leu Gln
            115                 120                 125

Glu Ala Ser Asp Ala Ser Ala Gly Pro Phe Gly Leu Ile Ile Asn Pro
        130                 135                 140

Lys Arg Tyr Ala Lys Leu Leu Lys Ile Tyr Glu Lys Ser Gly Lys Met
145                 150                 155                 160

Leu Val Glu Val Leu Lys Glu Ile Phe Arg Gly Gly Ile Ile Val Thr
                165                 170                 175

Leu Asn Ile Asp Glu Asn Lys Val Ile Ile Phe Ala Asn Thr Pro Ala
                180                 185                 190

Val Leu Asp Val Val Gly Gln Asp Val Thr Leu Gln Glu Leu Gly
            195                 200                 205

Pro Glu Gly Asp Val Ala Phe Leu Val Ser Glu Ala Ile Gly Ile
210                 215                 220

Arg Ile Lys Asn Pro Glu Ala Ile Val Val Leu Glu Gly Gly Ser Gly
225                 230                 235                 240

Gly Ser Gly Gly Ser Gly Gly Ser Gly Gly Gly Asp Thr Ile Thr Leu
            245                 250                 255

Pro Cys Arg Pro Ala Pro Pro Pro His Cys Ser Ser Asn Ile Thr Gly
        260                 265                 270

Leu Ile Leu Thr Arg Asp Gly Gly Asn Ser Asn Asp Glu Ser Glu Ile
        275                 280                 285

Phe Arg Pro Gly Gly Gly Asp Met Arg Asp Ile Ala Arg Cys Gln Ile
    290                 295                 300

Ala Gly Thr Val Val Ser Thr Gln Leu Leu Leu Asn Gly Ser Leu Ala
305                 310                 315                 320

Glu Glu Glu Val Val Ile Arg Ser Val Asp Phe Thr Asp Asn Ala Lys
                325                 330                 335

Ser Ile Cys Val Gln Leu Asn Thr Ser Val Glu Ile Asn Cys Thr Gly
        340                 345                 350

Ala Gly His Cys Asn Ile Ser Arg Ala Lys Trp Asn Asn Thr Leu Lys
            355                 360                 365

Gln Ile Ala Ser Lys Leu Arg Glu Gln Phe Gly Asn Asn Lys Thr Ile
        370                 375                 380

Ile Phe Lys Gln Ser Ser Gly Gly Asp Pro Glu Ile Val Thr His Ser
385                 390                 395                 400

Phe Asn Cys Gly Gly Glu Phe Phe Tyr Cys Asn Ser Thr Gln Leu Phe
                405                 410                 415
```

Asn Ser Thr Trp Phe Asn Ser Thr Trp Ser
            420                 425

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Pro Val Val Ser
1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Asn Trp Arg Ser
1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asp Asn Trp Arg Ser Glu
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Cys Thr Gly Ala Gly His Cys
1               5

<210> SEQ ID NO 95
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Cys Thr Arg Pro Asn Asn Asn Thr Arg Lys Arg Ile Arg Ile Gln Arg
1               5                   10                  15

Gly Pro Gly Arg Ala Phe Val Thr Ile Gly Lys Ile Gly Asn Met Arg
                20                  25                  30

Gln Ala His Cys
        35

-continued

```
<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Gly Gly Arg Pro Gly
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ile Pro Lys Arg Asp Phe Asn
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Pro Ala Pro Pro Pro His
1               5

<210> SEQ ID NO 99
<211> LENGTH: 26
<212> TYPE: PRT
<213> ORGANISM: Human immunodeficiency virus

<400> SEQUENCE: 99

Arg Ile Lys Gln Ile Ile Asn Met Trp Gln Lys Val Gly Lys Ala Met
1               5                   10                  15

Tyr Ala Pro Pro Ile Ser Gly Gln Ile Arg
            20                  25

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Leu Ser Gly
1

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 101

Gly Leu Ser Gly Pro
1               5

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ggchtwkcyg gtvyy                                                     15

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ile Ala Gly Ile
1               5

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Ile Ala Gly Val
1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Ile Ala Gly Ala
1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Ile Ser Gly Ala
1               5

<210> SEQ ID NO 107
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 107

Gly Leu Ser Gly Ala
1               5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Leu Ser Gly Val
1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Leu Ser Gly Ile
1               5

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Leu Ala Gly Thr
1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Ile Ala Gly Thr
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Asp Met Arg Asp Ile Ala Arg Cys
1               5
```

<210> SEQ ID NO 113
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
sstsrtrkrs ytsst                                                        15

<210> SEQ ID NO 114
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
agtccgaaat ttttagaccc ggcggcggcg atatgsstsr trkrsytsst tgcvbtvbtv       60
btvbtgtgtc tacacagctt cttcttaatg gctc                                  94

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Asp Met Ala Gly Met Pro Arg Cys Gly Gly Gly Ala Val Ser
1               5                   10                  15

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Asp Met Arg Asp Ile Ala Arg Cys Gln Ile Ala Gly Thr Val Val
1               5                   10                  15

Ser

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Thr Lys His His His His His His
1               5

<210> SEQ ID NO 118
<211> LENGTH: 321
<212> TYPE: PRT
<213> ORGANISM: Human immunodeficiency virus

<400> SEQUENCE: 118

```
Gly Ala Arg Ser Glu Val Val Leu Val Asn Val Thr Glu Asn Phe Asn
1               5                   10                  15

Met Trp Lys Asn Asp Met Val Glu Gln Met His Glu Asp Ile Ile Ser
            20                  25                  30

Leu Trp Asp Gln Ser Leu Lys Pro Cys Val Lys Leu Thr Pro Leu Cys
        35                  40                  45

Val Gly Ala Gly Ser Cys Asn Thr Ser Val Ile Thr Gln Ala Cys Pro
    50                  55                  60

Lys Val Ser Phe Glu Pro Ile Pro Ile His Tyr Cys Ala Pro Ala Gly
65              70                  75                  80

Phe Ala Ile Leu Lys Cys Asn Asn Lys Thr Phe Asn Gly Thr Gly Pro
                85                  90                  95

Cys Thr Asn Val Ser Thr Val Gln Cys Thr His Gly Ile Arg Pro Val
            100                 105                 110

Val Ser Thr Gln Leu Leu Leu Asn Gly Ser Leu Ala Glu Glu Glu Val
            115                 120                 125

Val Ile Arg Ser Val Asn Phe Thr Asp Asn Ala Lys Thr Ile Ile Val
130                 135                 140

Gln Leu Asn Thr Ser Val Glu Ile Asn Cys Thr Gly Ala Gly His Cys
145                 150                 155                 160

Asn Ile Ser Arg Ala Lys Trp Asn Asn Thr Leu Lys Gln Ile Ala Ser
                165                 170                 175

Lys Leu Arg Glu Gln Phe Gly Asn Asn Lys Thr Ile Ile Phe Lys Gln
            180                 185                 190

Ser Ser Gly Gly Asp Pro Glu Ile Val Thr His Ser Phe Asn Cys Gly
            195                 200                 205

Gly Glu Phe Phe Tyr Cys Asn Ser Thr Gln Leu Phe Asn Ser Thr Trp
        210                 215                 220

Phe Asn Ser Thr Trp Ser Thr Glu Gly Ser Asn Asn Thr Glu Gly Ser
225                 230                 235                 240

Asp Thr Ile Thr Leu Pro Cys Arg Ile Lys Gln Ile Ile Asn Met Trp
                245                 250                 255

Gln Lys Val Gly Lys Ala Met Tyr Ala Pro Pro Ile Ser Gly Gln Ile
            260                 265                 270

Arg Cys Ser Ser Asn Ile Thr Gly Leu Leu Leu Thr Arg Asp Gly Gly
            275                 280                 285

Asn Ser Asn Asn Glu Ser Glu Ile Phe Arg Pro Gly Gly Gly Asp Met
        290                 295                 300

Arg Asp Asn Trp Arg Ser Glu Leu Tyr Lys Tyr Lys Val Val Lys Ile
305                 310                 315                 320

Glu

<210> SEQ ID NO 119
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gly Ala Arg Ser Glu Val Val Leu Val Asp Val Thr Glu Asn Phe Asn
1               5                   10                  15

Met Trp Lys Asn Asp Met Val Glu Gln Met His Glu Asp Ile Ile Ser
            20                  25                  30
```

Leu Trp Asp Gln Ser Leu Lys Pro Cys Val Lys Leu Thr Pro Leu Cys
        35                  40                  45

Val Gly Ala Gly Ser Cys Asp Thr Ser Val Ile Thr Gln Ala Cys Pro
 50                  55                  60

Lys Val Ser Phe Glu Pro Ile Pro Ile His Tyr Cys Ala Pro Ala Gly
 65                  70                  75                  80

Phe Ala Ile Leu Lys Cys Asn Asp Lys Thr Phe Asp Gly Thr Gly Pro
                 85                  90                  95

Cys Thr Asp Val Ser Thr Val Gln Cys Thr His Gly Ile Arg Pro Val
            100                 105                 110

Val Ser Thr Gln Leu Leu Leu Asp Gly Ser Leu Ala Glu Glu Val
            115                 120                 125

Val Ile Arg Ser Val Asp Phe Thr Asp Asn Ala Lys Thr Ile Ile Val
        130                 135                 140

Gln Leu Asp Thr Ser Val Glu Ile Asp Cys Thr Gly Ala Gly His Cys
145                 150                 155                 160

Asn Ile Ser Arg Ala Lys Trp Asp Asn Thr Leu Lys Gln Ile Ala Ser
                165                 170                 175

Lys Leu Arg Glu Gln Phe Gly Asn Asp Lys Thr Ile Ile Phe Lys Gln
            180                 185                 190

Ser Ser Gly Gly Asp Pro Glu Ile Val Thr His Ser Phe Asn Cys Gly
            195                 200                 205

Gly Glu Phe Phe Tyr Cys Asp Ser Thr Gln Leu Phe Asp Ser Thr Trp
        210                 215                 220

Phe Asp Ser Thr Trp Thr Glu Gly Ser Asp Asn Thr Glu Gly Ser
225                 230                 235                 240

Asp Thr Ile Thr Leu Pro Cys Arg Ile Lys Gln Ile Ile Asn Met Trp
                245                 250                 255

Gln Lys Val Gly Lys Ala Met Tyr Ala Pro Pro Ile Ser Gly Gln Ile
            260                 265                 270

Arg Cys Ser Ser Asp Ile Thr Gly Leu Leu Leu Thr Arg Asp Gly Gly
            275                 280                 285

Asn Ser Asn Asp Glu Ser Glu Ile Phe Arg Pro Gly Gly Gly Asp Met
        290                 295                 300

Arg Asp Asn Trp Arg Ser Glu Leu Tyr Lys Tyr Lys Val Val Lys Ile
305                 310                 315                 320

Glu

<210> SEQ ID NO 120
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gly Ala Arg Ser Glu Val Val Leu Val Asn Val Thr Glu Asn Phe Asn
1               5                   10                  15

Met Trp Lys Asn Asp Met Val Glu Gln Met His Glu Asp Ile Ile Ser
            20                  25                  30

Leu Trp Asp Gln Ser Leu Lys Pro Cys Val Lys Leu Thr Pro Leu Cys
        35                  40                  45

Val Gly Ala Gly Ser Cys Asp Thr Ser Val Ile Thr Gln Ala Cys Pro
 50                  55                  60

Lys Val Ser Phe Glu Pro Ile Pro Ile His Tyr Cys Ala Pro Ala Gly
65                  70                  75                  80

Phe Ala Ile Leu Lys Cys Asn Asn Lys Thr Phe Asn Gly Thr Gly Pro
                85                  90                  95

Cys Thr Asn Val Ser Thr Val Gln Cys Thr His Gly Ile Arg Pro Val
                100                 105                 110

Val Ser Thr Gln Leu Leu Leu Asn Gly Ser Leu Ala Glu Glu Glu Val
                115                 120                 125

Val Ile Arg Ser Val Asp Phe Thr Asp Asn Ala Lys Thr Ile Ile Val
130                 135                 140

Gln Leu Asn Thr Ser Val Glu Ile Asn Cys Thr Gly Ala Gly His Cys
145                 150                 155                 160

Asn Ile Ser Arg Ala Lys Trp Asp Asn Thr Leu Lys Gln Ile Ala Ser
                165                 170                 175

Lys Leu Arg Glu Gln Phe Gly Asn Asn Lys Thr Ile Ile Phe Lys Gln
                180                 185                 190

Ser Ser Gly Gly Asp Pro Glu Ile Val Thr His Ser Phe Asn Cys Gly
                195                 200                 205

Gly Glu Phe Phe Tyr Cys Asp Ser Thr Gln Leu Phe Asp Ser Thr Trp
210                 215                 220

Phe Asp Ser Thr Trp Ser Thr Glu Gly Ser Asn Asn Thr Glu Gly Ser
225                 230                 235                 240

Asp Thr Ile Thr Leu Pro Cys Arg Ile Lys Gln Ile Ile Asn Met Trp
                245                 250                 255

Gln Lys Val Gly Lys Ala Met Tyr Ala Pro Pro Ile Ser Gly Gln Ile
                260                 265                 270

Arg Cys Ser Ser Asn Ile Thr Gly Leu Leu Leu Thr Arg Asp Gly Gly
                275                 280                 285

Asn Ser Asn Asp Glu Ser Glu Ile Phe Arg Pro Gly Gly Gly Asp Met
                290                 295                 300

Arg Asp Asn Trp Arg Ser Glu Leu Tyr Lys Tyr Lys Val Val Lys Ile
305                 310                 315                 320

Glu

<210> SEQ ID NO 121
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gly Ala Arg Ser Glu Val Val Leu Val Asn Val Thr Glu Asn Phe Asn
1               5                   10                  15

Met Trp Lys Asn Asp Met Val Glu Gln Met His Glu Asp Ile Ile Ser
                20                  25                  30

Leu Trp Asp Gln Ser Leu Lys Pro Cys Val Lys Leu Thr Pro Leu Cys
            35                  40                  45

Val Gly Ala Gly Ser Cys Asn Thr Ser Val Ile Thr Gln Ala Cys Pro
        50                  55                  60

Lys Val Ser Phe Glu Pro Ile Pro Ile His Tyr Cys Ala Pro Ala Gly
65                  70                  75                  80

Phe Ala Ile Leu Lys Cys Asn Asn Lys Thr Phe Asn Gly Thr Gly Pro
                85                  90                  95

```
Cys Thr Asn Val Ser Thr Val Gln Cys Thr His Gly Ile Arg Pro Val
            100                 105                 110

Val Ser Thr Gln Leu Leu Leu Asn Gly Ser Leu Ala Glu Glu Val
        115                 120                 125

Val Ile Arg Ser Val Asn Phe Thr Asp Asn Ala Lys Thr Ile Ile Val
130                 135                 140

Gln Leu Asn Thr Ser Val Glu Ile Asn Cys Thr Gly Ala Gly His Cys
145                 150                 155                 160

Asn Ile Ser Arg Ala Lys Trp Asn Asn Thr Leu Lys Gln Ile Ala Ser
                165                 170                 175

Lys Leu Arg Glu Gln Phe Gly Asn Asn Lys Thr Ile Ile Phe Lys Gln
            180                 185                 190

Ser Ser Gly Gly Asp Pro Glu Ile Val Thr His Ser Phe Asn Cys Gly
        195                 200                 205

Gly Glu Phe Phe Tyr Cys Asp Ser Thr Gln Leu Phe Asn Ser Thr Trp
    210                 215                 220

Phe Asn Ser Thr Trp Ser Thr Glu Gly Ser Asn Asn Thr Glu Gly Ser
225                 230                 235                 240

Asp Thr Ile Thr Leu Pro Cys Arg Ile Lys Gln Ile Ile Asn Met Trp
                245                 250                 255

Gln Lys Val Gly Lys Ala Met Tyr Ala Pro Pro Ile Ser Gly Gln Ile
            260                 265                 270

Arg Cys Ser Ser Asn Ile Thr Gly Leu Leu Leu Thr Arg Asp Gly Gly
        275                 280                 285

Asn Ser Asn Asn Glu Ser Glu Ile Phe Arg Pro Gly Gly Gly Asp Met
    290                 295                 300

Arg Asp Asn Trp Arg Ser Glu Leu Tyr Lys Tyr Lys Val Val Lys Ile
305                 310                 315                 320

Glu

<210> SEQ ID NO 122
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Arg Pro Val Val Ser Thr Gln Leu Leu Leu Asp Gly Ser Leu Ala Glu
1               5                   10                  15

Glu Glu Val Val Ile Arg Ser Val Asp Phe Thr Asp Asn Ala Lys Thr
            20                  25                  30

Ile Ile Val Gln Leu Asp Thr Ser Val Glu Ile Asp Cys Thr Gly Ala
        35                  40                  45

Gly His Cys Asn Ile Ser Arg Ala Lys Trp Asp Asn Thr Leu Lys Gln
    50                  55                  60

Ile Ala Ser Lys Leu Arg Glu Gln Phe Gly Asn Asp Lys Thr Ile Ile
65                  70                  75                  80

Phe Lys Gln Ser Ser Gly Gly Asp Pro Glu Ile Val Thr His Ser Phe
                85                  90                  95

Asn Cys Gly Gly Glu Phe Phe Tyr Cys Asp Ser Thr Gln Leu Phe Asp
            100                 105                 110

Ser Thr Trp Phe Asp Ser Thr Trp Ser Thr Glu Gly Ser Asp Asn Thr
        115                 120                 125
```

```
Glu Gly Ser Asp Thr Ile Thr Leu Pro Cys Arg Ile Lys Gln Ile Ile
        130                 135                 140

Asn Met Trp Gln Lys Val Gly Lys Ala Met Tyr Ala Pro Pro Ile Ser
145                 150                 155                 160

Gly Gln Ile Arg Cys Ser Ser Asp Ile Thr Gly Leu Leu Thr Arg
                165                 170                 175

Asp Gly Gly Asn Ser Asn Asp Glu Ser Glu Ile Phe Arg Pro Gly Gly
                180                 185                 190

Gly Asp Met Arg Asp Asn Trp Arg Ser Glu
                195                 200

<210> SEQ ID NO 123
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Arg Pro Val Val Ser Thr Gln Leu Leu Leu Asn Gly Ser Leu Ala Glu
1               5                   10                  15

Glu Glu Val Val Ile Arg Ser Val Asp Phe Thr Asp Asn Ala Lys Thr
                20                  25                  30

Ile Ile Val Gln Leu Asn Thr Ser Val Glu Ile Asn Cys Thr Gly Ala
            35                  40                  45

Gly His Cys Asn Ile Ser Arg Ala Lys Trp Asn Thr Leu Lys Gln
        50                  55                  60

Ile Ala Ser Lys Leu Arg Glu Gln Phe Gly Asn Asn Lys Thr Ile Ile
65                  70                  75                  80

Phe Lys Gln Ser Ser Gly Gly Asp Pro Glu Ile Val Thr His Ser Phe
                85                  90                  95

Asn Cys Gly Gly Glu Phe Phe Tyr Cys Asp Ser Thr Gln Leu Phe Asp
                100                 105                 110

Ser Thr Trp Phe Asp Ser Thr Trp Ser Thr Glu Gly Ser Asn Asn Thr
            115                 120                 125

Glu Gly Ser Asp Thr Ile Thr Leu Pro Cys Arg Ile Lys Gln Ile Ile
        130                 135                 140

Asn Met Trp Gln Lys Val Gly Lys Ala Met Tyr Ala Pro Pro Ile Ser
145                 150                 155                 160

Gly Gln Ile Arg Cys Ser Ser Asn Ile Thr Gly Leu Leu Thr Arg
                165                 170                 175

Asp Gly Gly Asn Ser Asn Asp Glu Ser Glu Ile Phe Arg Pro Gly Gly
                180                 185                 190

Gly Asp Met Arg Asp Asn Trp Arg Ser Glu
                195                 200

<210> SEQ ID NO 124
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Arg Pro Val Val Ser Thr Gln Leu Leu Leu Asn Gly Ser Leu Ala Glu
1               5                   10                  15
```

Glu Val Val Ile Arg Ser Val Asn Phe Thr Asp Asn Ala Lys Thr
            20                  25                  30

Ile Ile Val Gln Leu Asn Thr Ser Val Glu Ile Asn Cys Thr Gly Ala
            35                  40                  45

Gly His Cys Asn Ile Ser Arg Ala Lys Trp Asn Asn Thr Leu Lys Gln
50                  55                  60

Ile Ala Ser Lys Leu Arg Glu Gln Phe Gly Asn Asn Lys Thr Ile Ile
65                  70                  75                  80

Phe Lys Gln Ser Ser Gly Gly Asp Pro Glu Ile Val Thr His Ser Phe
                85                  90                  95

Asn Cys Gly Gly Glu Phe Phe Tyr Cys Asp Ser Thr Gln Leu Phe Asn
            100                 105                 110

Ser Thr Trp Phe Asn Ser Thr Trp Ser Thr Glu Gly Ser Asn Asn Thr
            115                 120                 125

Glu Gly Ser Asp Thr Ile Thr Leu Pro Cys Arg Ile Lys Gln Ile Ile
130                 135                 140

Asn Met Trp Gln Lys Val Gly Lys Ala Met Tyr Ala Pro Pro Ile Ser
145                 150                 155                 160

Gly Gln Ile Arg Cys Ser Ser Asn Ile Thr Gly Leu Leu Leu Thr Arg
                165                 170                 175

Asp Gly Gly Asn Ser Asn Asn Glu Ser Glu Ile Phe Arg Pro Gly Gly
            180                 185                 190

Gly Asp Met Arg Asp Asn Trp Arg Ser Glu
            195                 200

<210> SEQ ID NO 125
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Asp Thr Ile Thr Leu Pro Cys Arg Pro Ala Pro Pro His Cys Ser
1               5                   10                  15

Ser Asp Ile Thr Gly Leu Ile Leu Thr Arg Asp Gly Gly Asn Ser Asn
            20                  25                  30

Asp Glu Ser Glu Ile Phe Arg Pro Gly Gly Asp Met Arg Asp Ile
            35                  40                  45

Ala Arg Cys Gln Ile Ala Gly Thr Val Val Ser Thr Gln Leu Leu Leu
50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asp Thr Ser Val Glu
                85                  90                  95

Ile Asp Cys Thr Gly Ala Gly His Cys Asp Ile Ser Arg Ala Lys Trp
            100                 105                 110

Asp Asn Thr Leu Lys Gln Ile Ala Ser Lys Leu Arg Glu Gln Phe Gly
            115                 120                 125

Asn Asp Lys Thr Ile Ile Phe Lys Gln Ser Ser Gly Gly Asp Pro Glu
            130                 135                 140

Ile Val Thr His Ser Phe Asn Cys Gly Gly Glu Phe Phe Tyr Cys Asp
145                 150                 155                 160

Ser Thr Gln Leu Phe Asp Ser Thr Trp Phe Asp Ser Thr Trp Ser

<210> SEQ ID NO 126
<211> LENGTH: 175
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 126

Asp Thr Ile Thr Leu Pro Cys Arg Pro Ala Pro Pro His Cys Ser
1               5                   10                  15
Ser Asn Ile Thr Gly Leu Ile Leu Thr Arg Asp Gly Gly Asn Ser Asn
            20                  25                  30
Asp Glu Ser Glu Ile Phe Arg Pro Gly Gly Gly Asp Met Arg Asp Ile
        35                  40                  45
Ala Arg Cys Gln Ile Ala Gly Thr Val Val Ser Thr Gln Leu Leu Leu
    50                  55                  60
Asp Gly Ser Leu Ala Glu Glu Val Val Ile Arg Ser Val Asp Phe
65                  70                  75                  80
Thr Asp Asn Ala Lys Ser Ile Cys Val Gln Leu Asp Thr Ser Val Glu
                85                  90                  95
Ile Asp Cys Thr Gly Ala Gly His Cys Asp Ile Ser Arg Ala Lys Trp
            100                 105                 110
Asp Asn Thr Leu Lys Gln Ile Ala Ser Lys Leu Arg Glu Gln Phe Gly
        115                 120                 125
Asn Asp Lys Thr Ile Ile Phe Lys Gln Ser Ser Gly Gly Asp Pro Glu
    130                 135                 140
Ile Val Thr His Ser Phe Asn Cys Gly Gly Glu Phe Phe Tyr Cys Asp
145                 150                 155                 160
Ser Thr Gln Leu Phe Asp Ser Thr Trp Phe Asp Ser Thr Trp Ser
                165                 170                 175

<210> SEQ ID NO 127
<211> LENGTH: 175
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

Asp Thr Ile Thr Leu Pro Cys Arg Pro Ala Pro Pro His Cys Ser
1               5                   10                  15
Ser Asp Ile Thr Gly Leu Ile Leu Thr Arg Asp Gly Gly Asn Ser Asn
            20                  25                  30
Asp Glu Ser Glu Ile Phe Arg Pro Gly Gly Gly Asp Met Arg Asp Ile
        35                  40                  45
Ala Arg Cys Gln Ile Ala Gly Thr Val Val Ser Thr Gln Leu Leu Leu
    50                  55                  60
Asp Gly Ser Leu Ala Glu Glu Val Val Ile Arg Ser Val Asp Phe
65                  70                  75                  80
Thr Asp Asn Ala Lys Ser Ile Cys Val Gln Leu Asp Thr Ser Val Glu
                85                  90                  95
Ile Asp Cys Thr Gly Ala Gly His Cys Asp Ile Ser Arg Ala Lys Trp
            100                 105                 110
Asp Asn Thr Leu Lys Gln Ile Ala Ser Lys Leu Arg Glu Gln Phe Gly

```
            115                 120                 125

Asn Asp Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asp
145                 150                 155                 160

Ser Thr Gln Leu Phe Asp Ser Thr Trp Phe Asp Ser Thr Trp Ser
                165                 170                 175

<210> SEQ ID NO 128
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Asp Thr Ile Thr Leu Pro Cys Arg Ile Lys Gln Ile Ile Asn Met Trp
1               5                   10                  15

Gln Lys Val Gly Lys Ala Met Tyr Ala Pro Pro Ile Ser Gly Gln Ile
                20                  25                  30

Arg Cys Ser Ser Asn Ile Thr Gly Leu Ile Leu Thr Arg Asp Gly Gly
            35                  40                  45

Asn Ser Asn Asn Glu Ser Glu Ile Phe Arg Pro Gly Gly Gly Asp Met
50                  55                  60

Arg Asp Ile Ala Arg Cys Gln Ile Ala Gly Thr Val Val Ser Thr Gln
65                  70                  75                  80

Leu Leu Leu Asn Gly Ser Leu Ala Glu Glu Glu Val Val Ile Arg Ser
                85                  90                  95

Val Asn Phe Thr Asp Asn Ala Lys Ser Ile Cys Val Gln Leu Asn Thr
            100                 105                 110

Ser Val Glu Ile Asn Cys Thr Gly Ala Gly His Cys Asn Ile Ser Arg
        115                 120                 125

Ala Lys Trp Asn Asn Thr Leu Lys Gln Ile Ala Ser Lys Leu Arg Glu
    130                 135                 140

Gln Phe Gly Asn Asn Lys Thr Ile Ile Phe Lys Gln Ser Ser Gly Gly
145                 150                 155                 160

Asp Pro Glu Ile Val Thr His Ser Phe Asn Cys Gly Gly Glu Phe Phe
                165                 170                 175

Tyr Cys Asp Ser Thr Gln Leu Phe Asn Ser Thr Trp Phe Asn Ser Thr
            180                 185                 190

Trp Ser

<210> SEQ ID NO 129
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(106)
<223> OTHER INFORMATION: This region may be absent or encompass SEQ ID
      NO: 130 or SEQ ID NO: 131 wherein some residues may not be present
<220> FEATURE:
<221> NAME/KEY: MOD_RES
<222> LOCATION: (107)..(107)
<223> OTHER INFORMATION: May or may not be present
<220> FEATURE:
<221> NAME/KEY: MOD_RES
```

```
<222> LOCATION: (108)..(108)
<223> OTHER INFORMATION: Pro, Thr or Gly
<220> FEATURE:
<221> NAME/KEY: MOD_RES
<222> LOCATION: (109)..(109)
<223> OTHER INFORMATION: Val or Ala
<220> FEATURE:
<221> NAME/KEY: MOD_RES
<222> LOCATION: (117)..(117)
<223> OTHER INFORMATION: Asn or Asp
<220> FEATURE:
<221> NAME/KEY: MOD_RES
<222> LOCATION: (127)..(127)
<223> OTHER INFORMATION: Ile or Cys
<220> FEATURE:
<221> NAME/KEY: MOD_RES
<222> LOCATION: (131)..(131)
<223> OTHER INFORMATION: Asn or Asp
<220> FEATURE:
<221> NAME/KEY: MOD_RES
<222> LOCATION: (138)..(138)
<223> OTHER INFORMATION: Thr, Ser or Cys
<220> FEATURE:
<221> NAME/KEY: MOD_RES
<222> LOCATION: (140)..(140)
<223> OTHER INFORMATION: Ile or Cys
<220> FEATURE:
<221> NAME/KEY: MOD_RES
<222> LOCATION: (144)..(144)
<223> OTHER INFORMATION: Asn or Asp
<220> FEATURE:
<221> NAME/KEY: MOD_RES
<222> LOCATION: (150)..(150)
<223> OTHER INFORMATION: Asn or Asp
<220> FEATURE:
<221> NAME/KEY: MOD_RES
<222> LOCATION: (158)..(158)
<223> OTHER INFORMATION: Asn or Asp
<220> FEATURE:
<221> NAME/KEY: MOD_RES
<222> LOCATION: (165)..(165)
<223> OTHER INFORMATION: Asn or Asp
<220> FEATURE:
<221> NAME/KEY: MOD_RES
<222> LOCATION: (174)..(174)
<223> OTHER INFORMATION: Lys or Cys
<220> FEATURE:
<221> NAME/KEY: MOD_RES
<222> LOCATION: (181)..(182)
<223> OTHER INFORMATION: Asn or Asp
<220> FEATURE:
<221> NAME/KEY: MOD_RES
<222> LOCATION: (206)..(308)
<223> OTHER INFORMATION: This region may be absent or encompass SEQ ID
      NO: 139 or SEQ ID NO: 140 wherein some residues may not be present
<220> FEATURE:
<223> OTHER INFORMATION: see specification as filed for detailed
      description of substitutions and preferred embodiments

<400> SEQUENCE: 129

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95
```

```
Xaa Xaa Xaa Xaa Xaa Xaa Xaa Xaa Arg Xaa Xaa Val Ser Thr
            100                 105                 110

Gln Leu Leu Leu Xaa Gly Ser Leu Ala Glu Glu Val Val Xaa Arg
        115                 120                 125

Ser Val Xaa Phe Thr Asp Asn Ala Lys Xaa Ile Xaa Val Gln Leu Xaa
        130                 135                 140

Thr Ser Val Glu Ile Xaa Cys Thr Gly Ala Gly His Cys Xaa Ile Ser
145                 150                 155                 160

Arg Ala Lys Trp Xaa Asn Thr Leu Lys Gln Ile Ala Ser Xaa Leu Arg
                165                 170                 175

Glu Gln Phe Gly Xaa Xaa Lys Thr Ile Ile Phe Lys Gln Ser Ser Gly
        180                 185                 190

Gly Asp Pro Glu Ile Val Thr His Ser Phe Asn Cys Gly Xaa Xaa Xaa
        195                 200                 205

Xaa Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
        245                 250                 255

Xaa Xaa Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
        290                 295                 300

Xaa Xaa Xaa Xaa
305

<210> SEQ ID NO 130
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(65)
<223> OTHER INFORMATION: This region may encompass SEQ ID NO: 142 or
      any amino acid sequence encompassing 6-8 residues
<220> FEATURE:
<221> NAME/KEY: MOD_RES
<222> LOCATION: (74)..(74)
<223> OTHER INFORMATION: Leu or Ile
<220> FEATURE:
<221> NAME/KEY: MOD_RES
<222> LOCATION: (98)..(98)
<223> OTHER INFORMATION: Asp or Cys
<220> FEATURE:
<221> NAME/KEY: MOD_RES
<222> LOCATION: (99)..(106)
<223> OTHER INFORMATION: Any amino acid
<220> FEATURE:
<223> OTHER INFORMATION: see specification as filed for detailed
      description of substitutions and preferred embodiments

<400> SEQUENCE: 130

Gly Glu Phe Phe Tyr Cys Asp Ser Thr Gln Leu Phe Asn Ser Thr Trp
1               5                   10                  15

Phe Asn Ser Thr Trp Ser Thr Glu Gly Ser Asn Asn Thr Glu Gly Ser
            20                  25                  30
```

Asp Thr Ile Thr Leu Pro Cys Arg Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
50                  55                  60

Xaa Cys Ser Ser Asn Ile Thr Gly Leu Xaa Leu Thr Arg Asp Gly Gly
65                  70                  75                  80

Asn Ser Asn Asn Glu Ser Glu Ile Phe Arg Pro Gly Gly Gly Asp Met
                85                  90                  95

Arg Xaa Xaa Xaa Xaa Xaa Xaa Xaa Xaa
            100                 105

<210> SEQ ID NO 131
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(33)
<223> OTHER INFORMATION: This region may encompass SEQ ID NO: 142 or
      any amino acid sequence encompassing 6-8 residues
<220> FEATURE:
<221> NAME/KEY: MOD_RES
<222> LOCATION: (37)..(37)
<223> OTHER INFORMATION: Asn or Asp
<220> FEATURE:
<221> NAME/KEY: MOD_RES
<222> LOCATION: (42)..(42)
<223> OTHER INFORMATION: Leu or Ile
<220> FEATURE:
<221> NAME/KEY: MOD_RES
<222> LOCATION: (49)..(49)
<223> OTHER INFORMATION: Asn or Asp
<220> FEATURE:
<221> NAME/KEY: MOD_RES
<222> LOCATION: (51)..(52)
<223> OTHER INFORMATION: Asn or Asp
<220> FEATURE:
<221> NAME/KEY: MOD_RES
<222> LOCATION: (65)..(66)
<223> OTHER INFORMATION: May or may not be present
<220> FEATURE:
<221> NAME/KEY: MOD_RES
<222> LOCATION: (67)..(74)
<223> OTHER INFORMATION: Any amino acid
<220> FEATURE:
<223> OTHER INFORMATION: see specification as filed for detailed
      description of substitutions and preferred embodiments

<400> SEQUENCE: 131

Asp Thr Ile Thr Leu Pro Cys Arg Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Cys Ser Ser Xaa Ile Thr Gly Leu Xaa Leu Thr Arg Asp Gly Gly
        35                  40                  45

Xaa Ser Xaa Xaa Glu Ser Glu Ile Phe Arg Pro Gly Gly Gly Asp Met
    50                  55                  60

Arg Asp Xaa Xaa Xaa Xaa Xaa Xaa Xaa Xaa
65                  70

<210> SEQ ID NO 132
<211> LENGTH: 4
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 132

Asn Trp Arg Ser
1

<210> SEQ ID NO 133
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ile Ala Arg Cys
1

<210> SEQ ID NO 134
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Gly Met Pro
1

<210> SEQ ID NO 135
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Ala Arg Ser
1

<210> SEQ ID NO 136
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Ile Ala Gly
1

<210> SEQ ID NO 137
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Cys Gly Gly
1
```

```
<210> SEQ ID NO 138
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Ile Ala Gly
1

<210> SEQ ID NO 139
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(32)
<223> OTHER INFORMATION: This region may or may not be present in its
      entirety
<220> FEATURE:
<221> NAME/KEY: MOD_RES
<222> LOCATION: (41)..(65)
<223> OTHER INFORMATION: This region may encompass SEQ ID NO: 142 or
      any amino acid sequence encompassing 6-8 residues
<220> FEATURE:
<221> NAME/KEY: MOD_RES
<222> LOCATION: (97)..(98)
<223> OTHER INFORMATION: May or may not be present
<220> FEATURE:
<221> NAME/KEY: MOD_RES
<222> LOCATION: (99)..(102)
<223> OTHER INFORMATION: Any amino acid
<220> FEATURE:
<221> NAME/KEY: MOD_RES
<222> LOCATION: (103)..(103)
<223> OTHER INFORMATION: May or may not be present
<220> FEATURE:
<223> OTHER INFORMATION: see specification as filed for detailed
      description of substitutions and preferred embodiments

<400> SEQUENCE: 139

Gly Glu Phe Phe Tyr Cys Asp Ser Thr Gln Leu Phe Asn Ser Thr Trp
1               5                   10                  15

Phe Asn Ser Thr Trp Ser Thr Glu Gly Ser Asn Asn Thr Glu Gly Ser
            20                  25                  30

Asp Thr Ile Thr Leu Pro Cys Arg Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Cys Ser Ser Asn Ile Thr Gly Leu Leu Leu Thr Arg Asp Gly Gly
65                  70                  75                  80

Asn Ser Asn Asn Glu Ser Glu Ile Phe Arg Pro Gly Gly Gly Asp Met
                85                  90                  95

Arg Asp Xaa Xaa Xaa Xaa Glu
            100

<210> SEQ ID NO 140
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (13)..(13)
<223> OTHER INFORMATION: Asn or Asp
<220> FEATURE:
<221> NAME/KEY: MOD_RES
<222> LOCATION: (18)..(18)
<223> OTHER INFORMATION: Asn, Asp or not present
<220> FEATURE:
<221> NAME/KEY: MOD_RES
<222> LOCATION: (19)..(22)
<223> OTHER INFORMATION: May or may not be present

<400> SEQUENCE: 140

Gly Glu Phe Phe Tyr Cys Asp Ser Thr Gln Leu Phe Xaa Ser Thr Trp
1               5                   10                  15

Phe Xaa Ser Thr Trp Ser
            20

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Thr Glu Gly Ser Asn Asn Thr Glu Gly Ser
1               5                   10

<210> SEQ ID NO 142
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ile Lys Gln Ile Ile Asn Met Trp Gln Lys Val Gly Lys Ala Met Tyr
1               5                   10                  15

Ala Pro Pro Ile Ser Gly Gln Ile Arg
            20                  25

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Pro Ala Pro Pro Pro His
1               5

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ser Ala Ser Glu Gly Ser
1               5
```

<210> SEQ ID NO 145
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gly Ser Gly Gly Ser Gly Gly Leu Asn Asp Ile Phe Glu Ala Gln
1               5                   10                  15

Lys Ile Glu Trp His Glu
            20

<210> SEQ ID NO 146
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (246)..(263)
<223> OTHER INFORMATION: Any amino acid

<400> SEQUENCE: 146

Val Trp Lys Asp Ala Thr Thr Thr Leu Phe Cys Ala Ser Asp Ala Lys
1               5                   10                  15

Ala His Glu Thr Glu Val His Asn Val Trp Ala Thr His Ala Cys Val
            20                  25                  30

Pro Thr Asp Pro Asn Pro Gln Glu Val Glu Leu Lys Asn Val Thr Glu
        35                  40                  45

Asn Phe Asn Met Trp Lys Asn Asn Met Val Glu Gln Met His Glu Asp
    50                  55                  60

Ile Ile Ser Leu Trp Asp Gln Ser Leu Lys Pro Cys Val Lys Leu Thr
65                  70                  75                  80

Gly Gly Ser Val Ile Thr Gln Ala Cys Pro Lys Val Ser Phe Glu Pro
                85                  90                  95

Ile Pro Ile His Tyr Cys Ala Pro Ala Gly Phe Ala Ile Leu Lys Cys
            100                 105                 110

Lys Asp Lys Lys Phe Asn Gly Lys Gly Pro Cys Ser Asn Val Ser Thr
        115                 120                 125

Val Gln Cys Thr His Gly Ile Arg Pro Val Val Ser Thr Gln Leu Leu
    130                 135                 140

Leu Asn Gly Ser Leu Ala Glu Glu Val Val Ile Arg Ser Glu Asp
145                 150                 155                 160

Phe Arg Asn Asn Ala Lys Ile Ile Ile Val Gln Leu Asn Glu Ser Val
                165                 170                 175

Glu Ile Asn Cys Thr Gly Ala Gly His Cys Asn Leu Ser Arg Ala Lys
            180                 185                 190

Trp Asn Asp Thr Leu Asn Lys Ile Val Ile Lys Leu Arg Glu Gln Phe
        195                 200                 205

Gly Asn Lys Thr Ile Val Phe Lys His Ser Ser Gly Gly Asp Pro Glu
    210                 215                 220

Ile Val Thr His Ser Phe Asn Cys Gly Gly Glu Phe Phe Tyr Cys Asn
225                 230                 235                 240

Ser Thr Gln Leu Phe Xaa Xaa Xaa Xaa Xaa Xaa Xaa Xaa Xaa Xaa
                245                 250                 255

```
Xaa Xaa Xaa Xaa Xaa Xaa Ile Thr Leu Pro Cys Arg Ile Lys Gln
            260                 265                 270

Ile Ile Asn Met Trp Gln Glu Val Gly Arg Ala Met Tyr Ala Pro Pro
275                 280                 285

Ile Arg Gly Gln Ile Arg Cys Ser Ser Asn Ile Thr Gly Leu Leu Leu
290                 295                 300

Ile Arg Asp Gly Gly Pro Glu Asp Asn Lys Thr Glu Ile Phe Arg Pro
305                 310                 315                 320

Gly Gly Gly Asp Met Arg Asp Asn Trp Arg Ser Glu Leu Tyr Lys Tyr
                325                 330                 335

Lys Val Val Lys Ile Glu
            340

<210> SEQ ID NO 147
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (246)..(263)
<223> OTHER INFORMATION: Any amino acid

<400> SEQUENCE: 147

Val Trp Lys Asp Ala Thr Thr Thr Leu Phe Cys Ala Ser Asp Ala Lys
1               5                   10                  15

Ala His Glu Thr Glu Val His Asn Val Trp Ala Thr His Ala Cys Val
            20                  25                  30

Pro Thr Asp Pro Asn Pro Gln Glu Val Glu Leu Lys Asn Val Thr Glu
        35                  40                  45

Asn Phe Asn Met Trp Lys Asn Asn Met Val Glu Gln Met His Glu Asp
50                  55                  60

Ile Ile Ser Leu Trp Asp Gln Ser Leu Lys Pro Cys Val Lys Leu Thr
65                  70                  75                  80

Gly Gly Ser Val Ile Thr Gln Ala Cys Pro Lys Val Ser Phe Glu Pro
                85                  90                  95

Ile Pro Ile His Tyr Cys Ala Pro Ala Gly Phe Ala Ile Leu Lys Cys
            100                 105                 110

Lys Asp Lys Lys Phe Asn Gly Lys Gly Pro Cys Ser Asn Val Ser Thr
        115                 120                 125

Val Gln Cys Thr His Gly Ile Arg Pro Val Val Ser Thr Gln Leu Leu
130                 135                 140

Leu Asn Gly Ser Leu Ala Glu Glu Val Val Ile Arg Ser Glu Asp
145                 150                 155                 160

Phe Arg Asn Asn Ala Lys Ile Ile Ile Val Gln Leu Asn Glu Ser Val
                165                 170                 175

Glu Ile Asn Cys Thr Gly Ala Gly His Cys Asn Leu Ser Arg Ala Lys
            180                 185                 190

Trp Asn Asp Thr Leu Asn Lys Ile Val Ile Lys Leu Arg Glu Gln Phe
        195                 200                 205

Gly Asn Lys Thr Ile Val Phe Ser His Ser Ser Gly Asp Pro Glu
210                 215                 220

Phe Val Thr His Ser Phe Asn Cys Gly Gly Glu Phe Phe Tyr Cys Asn
225                 230                 235                 240
```

```
Ser Thr Gln Leu Phe Xaa Xaa Xaa Xaa Xaa Xaa Xaa Xaa Xaa
                245                 250                 255

Xaa Xaa Xaa Xaa Xaa Xaa Xaa Ile Thr Leu Pro Cys Arg Ile Lys Gln
            260                 265                 270

Ile Ile Asn Met Trp Gln Glu Val Gly Pro Ile Arg Gly Gln Ile Arg
        275                 280                 285

Cys Ser Ser Asn Ile Thr Gly Leu Leu Ile Arg Asp Gly Gly Ala
        290                 295                 300

Glu Asp Asn Lys Thr Glu Ile Phe Arg Pro Gly Gly Gly Asp Met Arg
305                 310                 315                 320

Asp Asn Trp Arg Ser Glu Leu Tyr Lys Tyr Lys Val Val Lys Ile Glu
                325                 330                 335

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Gly Ser Gly Gly Ser Gly Gly
1               5

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Gly Ser Gly Gly Ser Gly Gly Ser Gly Gly Ser Gly Gly Gly
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Tyr Ile Lys Ala Asn Ser Lys Phe Ile Gly Ile Thr Glu Leu
1               5                   10                  15

<210> SEQ ID NO 151
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Ser Gln Tyr Ile Lys Ala Asn Ser Lys Phe Ile Gly Ile Thr Glu
1               5                   10                  15

Leu Ser Gly

<210> SEQ ID NO 152
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 152

His His His His His His
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

His His His His His His Gly Ser Gly
1               5
```

US 10,421,789 B2

ENGINEERED OUTER DOMAIN (EOD) OF HIV GP120 AND MUTANTS THEREOF

RELATED APPLICATIONS AND INCORPORATION BY REFERENCE

This application is a continuation of U.S. application Ser. No. 14/978,132 filed Dec. 22, 2015, now U.S. Pat. No. 10,221,217, which application is a continuation of U.S. application Ser. No. 14/251,132 filed Apr. 11, 2014, which is continuation of International Patent Application Number PCT/US2012/60062 filed Oct. 12, 2012, which published as PCT Publication No. WO 2013/056122 on Apr. 18, 2013, which claims priority to U.S. Provisional Patent Application Nos. 61/546,465 filed Oct. 12, 2011 and 61/699,217 filed Sep. 10, 2012.

Reference is also made to international patent application Serial No. PCT/US2012/044996 filed Jun. 29, 2012.

The foregoing applications, and all documents cited therein ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant No. NIAID P01 AI094419-01. The government has certain rights in the invention.

FIELD OF THE INVENTION

The invention relates to an engineered outer domain (eOD) of HIV gp120 and mutants thereof and methods of making and using the same.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections rind malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+ T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Viruses have evolved a variety of mechanisms to escape antibody recognition, many of which involve features of the viral surface proteins, such as high variability, steric occlusion, and glycan coating. For HIV, the dense shield of glycans that decorate the viral Env protein was once believed to be refractory to antibody recognition, shielding conserved protein epitopes of important functional significance whose greater exposure would result in increased susceptibility to antibody neutralization.

The outer domain (OD) of human immunodeficiency virus (HIV)-1 gp120 represents an attractive, if difficult, target for a beneficial immune response to HIV infection. Unlike the entire gp120, the OD is structurally stable and contains the surfaces that interact with both the primary and secondary cellular receptors. The primary strain-specific neutralizing target, the V3 loop, lies within the OD, as do epitopes for two cross-reactive neutralizing monoclonal antibodies (mAbs), b12 and 2G12, and the contact sites for a number of inhibitory lectins. The OD is poorly immunogenic, at least in the context of complete gp120, but purposeful OD immunization can lead to a substantial antibody response.

Citation or identification of any document in this application is not an admission that such document is available as prior art to the present invention.

SUMMARY OF THE INVENTION

Variants of Applicants' engineered outer domain: (a) maintain high affinity for broadly neutralizing antibodies b12 and VRC01 (b) bind with little or no detectable affinity to CD4 or non-neutralizing CD4bs antibodies such as b6, b13, F105, 15e, m14 or m18 (c) lack the V3 loop and beta20/21 hairpin and are minimal in size (~175 residues compared to ~230 for wild-type outer domain) (d) display no evidence of aggregation (e) have N and C termini located distal from the CD4bs to allow coupling, by chemical or genetic means, to larger particles for the purpose of multimeric display (f) may be expressed with a minimum of only two (2) glycans which may be useful for manipulating immune responses.

The present invention relates to engineering of the eOD to: (a) improve binding to mature VRC01, in which Applicants use mature VRC01 binding affinity as a readout for structural mimicry of HIV Env, (b) improve binding to germline VRC01 and the germlines of other VH1-2 derived broadly-neutralizing antibodies, (c) designed glycan-masking mutations on eOD to focus antibody responses to the VRC01 epitope, (d) designed fusions of eOD to various protein multimers to enhance immunogenicity, including 4mers, 8mers, 24mers, 60mers, and 180mers, most important of which are the 60mers that present eOD on a virus-like particle, and/or (e) design of cocktails of different eODs that represent the full diversity of HIV sequences within the VRC01 epitope and surroundings.

In a first embodiment embodiment, the invention relates to a non-naturally occurring protein which may comprise an engineered outer domain (eOD) mutation advantageous for the elicitation of CD4-binding site (CD4bs)-directed broadly-neutralizing antibodies (bnAbs), wherein the protein may comprise any one of:

```
(a) ODm1(D386)
RPVVSTQLLLNGSLAEEEVVIRSVNFTDNAKTIIVQLNTSVEINCTGAGHCNISRAKWNN

TLKQIASKLREQFGNNKTIIFKQSSGGDPEIVTHSFNCGGEFFYCDSTQLFNSTWFNSTWS

TEGSNNTEGSDTITLPCRPAPPPHCSSNITGLLLTRDGGNSNNESEIFRPGGGDMRDNWRSE (b) ODm1(N386)
RPVVSTQLLLNGSLAEEEVVIRSVNFTDNAKTIIVQLNTSVEINCTGAGHCNISRAKWNN

TLKQIASKLREQFGNNKTIIFKQSSGGDPEIVTHSFNCGGEFFYCNSTQLFNSTWFNSTWS

TEGSNNTEGSDTITLPCRPAPPPHCSSNITGLLLTRDGGNSNNESEIFRPGGGDMRDNWRSE (c) c1
DTITLPCRPAPPPHCSSNITGLLLTRDGGNSNNESEIFRPGGGDMRDNWRSGLSGPVVST

QLLLNGSLAEEEVVIRSVNFTDNAKTIIVQLNTSVEINCTGAGHCNISRAKWNNTLKQIA

SKLREQFGNNKTHFKQSSGGDPEIVTHSFNCGGEFFYCDSTQLFNSTWFNSTWS (d) c2
GEFFYCDSTQLFNSTWFNSTWSTEGSNNTEGSDTITLPCRPAPPPHCSSNITGLLLTRDGG

NSNNESEIFRPGGGDMRDNWRSGLSGPVVSTQLLLNGSLAEEEVVIRSVNFTDNAKTIIV

QLNTSVEINCTGAGHCNISRAKWNNTLKQIASKLREQFGNNKTHIIFKQSSGGDPEIVTHSF

NCG (e) c1d1_N386D (also called "eOD_N386D")
DTITLPCRPAPPPHCSSNITGLILTRDGGNSNNESEIFRPGGGDMRDIARCQIAGTVVSTQL

LLNGSLAEEEVVIRSVNFTDNAKSICVQLNTSVEINCTGAGHCNISRAKWNNTLKQIASK

LREQFGNNKTIIFKQSSGGDPEIVTHSFNCGGEFFYCDSTQLFNSTWFNSTWS (f) c1d1_b10disulf
DTITLPCRPAPPPHCSSNITGLILTRDGGNSNNESEIFRPGGGDMRDIARCQIAGTVVSTQL

LLNGSLAEEEVVCRSVNFTDNAKSICVQLNTSVEINCTGAGHCNISRAKWNNTLKQIASC

LREQFGNNKTIIFKQSSGGDPEIVTHSFNCGGEFFYCDSTQLFNSTWFNSTWS
```

(g) c1d1_v2
DTITLPCRPAPPPHCSSNITGLILTRDGGNSNNESEIFRPGGGDMAGMPRCGGGAVSTQLL

LNGSLAEEEVVCRSVNFTDNAKSICVQLNTSVEINCTGAGHCNISRAKWNNTLKQIASCL

REQFGNNKTIIFKQSSGGDPEIVTHSFNCGGEFFYCDSTQLFNSTWF (h) c1d1_minglyc (also called "eOD_minglyc" and "c1d1_448_262_glycan")
DTITLPCRPAPPPHCSSNITGLILTRDGGNSNDESEIFRPGGGDMRDIARCQIAGTVVSTQL

LLNGSLAEEEVVIRSVDFTDNAKSICVQLDTSVEIDCTGAGHCDISRAKWDNTLKQIASK

LREQFGNDKTIIFKQSSGGDPEIVTHSFNCGGEFFYCDSTQLFDSTWFDSTWS (i) c2d1
GEFFYCDSTQLFNSTWFNSTWSTEGSNNTEGSDTITLPCRPAPPPHCSSNITGLILTRDGG

NSNNESEIFRPGGGDMRDIARCQIAGTVVSTQLLLNGSLAEEEVVIRSVNFTDNAKSICV

QLNTSVEINCTGAGHCNISRAKWNNTLKQIASKLREQFGNNKTIIFKQSSGGDPEIVTHSF

NCG (j) c2d2
GEFFYCDSTQLFNSTWFNSTWSTEGSNNTEGSDTITLPCRPAPPPHCSSNITGLILTRDGG

NSNNESEIFRPGGGDMRCGARSGIAGTVVSTQLLLNGSLAEEEVVIRSVNFTDNAKCIIV

QLNTSVEINCTGAGHCNISRAKWNNTLKQIASKLREQFGNNKTHFKQSSGGDPEIVTHSF

NCG (k) c2d1_b10disulf
GEFFYCDSTQLFNSTWFNSTWSTEGSNNTEGSDTITLPCRPAPPPHCSSNITGLILTRDGG

NSNNESEIFRPGGGDMRDIARCQIAGTVVSTQLLLNGSLAEEEVVCRSVNFTDNAKSICV

QLNTSVEINCTGAGHCNISRAKWNNTLKQIASCLREQFGNNKTIIFKQSSGGDPEIVTHSP

NCG or any combination thereof.

In a second embodiment, the invention relates to a non-naturally occurring protein which may comprise an eOD mutation to improve binding of mature VRC01, wherein the protein may comprise any one of:

(a) eOD
DTITLPCRPAPPPHCSSNITGLILTRDGGNSNNESEIFRPGGGDMRDIARCQIAGTVVSTQL

LLNGSLAEEEVVIRSVNFTDNAKSICVQLNTSVEINCTGAGHCNISRAKWNNTLKQIASK

LREQFGNNKTIIFKQSSGGDPEIVTHSFNCGGEFFYCNSTQLFNSTWFNSTWS (b) eOD_N276D (="eOD_D(-)")
DTITLPCRPAPPPHCSSNITGLILTRDGGNSNNESEIFRPGGGDMRDIARCQIAGTVVSTQL

LLNGSLAEEEVVIRSVDFTDNAKSICVQLNTSVEINCTGAGHCNISRAKWNNTLKQIASK

LREQFGNNKTIIFKQSSGGDPEIVTHSFNCGGEFFYCNSTQLFNSTWFNSTWS (c) eOD_N276D_N463D (="eOD_VD(-)")
DTITLPCRPAPPPHCSSNITGLILTRDGGNSDESEIFRPGGGDMRDIARCQIAGYVVSTQL

LLNGSLAEEEVVIRSVDFTDNAKSICVQLNTSVEINCTGAGHCNISRAKWNNTLKQIASK

LREQFGNNKTIIFKQSSGGDPEIVTHSFNCGGEFFYCNSTQLFNSTWFNSTWS (d) eOD_L260F
DTITLPCRPAPPHCSSNITGLILTRDGGNSNNESEIFRPGGGDMRDIARCQIAGTVVSTQL

FLNGSLAEEEVVIRSVNFTDNAKSICVQLNTSVEINCTGAGHCNISRAKWNNTLKQIASK

LREQFGNNKTIIFKQSSGGDPEIVTHSFNCGGEFFYCNSTQLFNSTWFNSTWS (e) eOD_L260F_N276D
DTITLPCRPAPPPHCSSNITGLILTRDGGNSNNESEIFRPGGGDMRDIARCQIAGTVVSTQL

FLNGSLAEEEVVIRSVDFTDNAKSICVQLNTSVEINCTGAGHCNISRAKWNNTLKQIASK

LREQFGNNKTIIFKQSSGGDPEIVTHSFNCGGEFFYCNSTQLFNSTWFNSTWS (f) eOD_L260F_N276D_N463D
DTITLPCRPAPPPHCSSNITGLILTRDGGNSNDESEIFRPGGGDMRDIARCQIAGTVVSTQL

FLNGSLAEEEVVIRSVDFTDNAKSICVQLNTSVEINCTGAGHCNISRAKWNNTLKQIASK

LREQFGNNKTIIFKQSSGGDPEIVTHSFNCGGEFFYCNSTQLFNSTWFNSTWS (g) eOD_I478N
DTITLPCRPAPPPHCSSNITGLILTRDGGNSNNESEIFRPGGGDMRDNARCQIAGTVVSTQ

LLLNGSLAEEEVVIRSVNFTDNAKSICVQLNTSVEINCTGAGHCNISRAKWNNTLKQIAS

KLREQFGNNKTIIFKQSSGGDPEIVTHSFNCGGEFFYCNSTQLFNSTWFNSTWS (h) eOD_Δ356
DTITLPCRPAPPPHCSSNITGLILTRDGGNSNNESEIFRPGGGDMRDIARCQIAGTVVSTQL

LLNGSLAEEEVVIRSVNIFTDNAKSICVQLNTSVEINCTGAGHCNISRAKWNNTLKQIASK

LREQFGN#KTIIFKQSSGGDPEIVTHSFNCGGEFFYCNSTQLFNSTWFNSTWS (i) eOD_S387T
DTITLPCRPAPPPHCSSNITGLILTRDGGNSNNESEIFRPGGGDMRDIARCQIAGTVVSTQL

LLNGSLAEEEVVIRSVNFTDNAKSICVQLNTSVEINCTGAGHCNISRAKWNNTLKQIASK

LREQFGNNKTIIFKQSSGGDPEIVTHSFNCGGEFFYCNTTQLFNSTWFNSTWS (j) eOD_V270I
DTITLPCRPAPPPHCSSNITGLILTRDGGNSNNESEIFRPGGGDMRDIARCQIAGTVVSTQL

LLNGSLAEEEIVIRSVNFTDNAKSICVQLNTSVEINCTGAGHCNISRAKWNNTLKQIASKL

REQFGNNKTIIFKQSSGGDPEIVTHSFNCGGEFFYCNSTQLFNSTWFNSTWS (k) eOD_T257S_L260F_S375W
DTITLPCRPAPPPHCSSNITGLILTRDGGNSNNESEIFRPGGGDMRDIARCQIAGTVVSQL

FLNGSLAEEEVVIRSVNFTDNAKSICVQLNTSVEINCTGAGHCNISRAKWNNTLKQIASK

LREQFGNNKTIIFKQSSGGDPEIVTHWFNCGGEFFYCNSTQLFNSTWFNSTWS (l) eOD_T257S_L260F_S375W_N276D
DTITLPCRPAPPPHCSSNITGLILTRDGGNSNNESEIFRPGGGDMRDIARCQIAGTVVSQL

FLNGSLAEEEVVIRSVDFTDNAKSICVQLNTSVEINCTGAGHCNISRAKWNNTLKQIASK

LREQFGNNKTIIFKQSSGGDPEIVTHWFNCGGEFFYCNSTQLFNSTWFNSTWS (m) eOD_T257S_L260F_S375W_N276D_N463D
DTITLPCRPAPPPHCSSNITGLILTRDGGNSNDESEIFRPGGGDMRDIARCQIAGTVVSQL

FLNGSLAEEEVVIRSVDFTDNAKSICVQLNTSVEINCTGAGHCNISRAKWNNTLKQIASK

LREQFGNNKTIIFKQSSGGDPEIVTHWFNCGGEFFYCNSTQLFNSTWFNSTWS or any combination thereof.

The eOD mutation may also improve germline VRC01 binding.

In a third embodiment, the invention relates to a non-naturally occurring protein which may comprise an eOD variant engineered to improve binding to germline VRC01 and/or other VH1-2 antibodies which may comprise any one of:

(a) eOD_VH1-2_v1.0
DTITLPCRPAPPPHCSSNITGLILTRDGGTSDDKTEIFRPGGGDMRDIARCQIAGTVVSTQL

LLNGSLAEEEVVIRSEDFRDNAKSICVQLNTSVEINCTGAGHCNISRAKWNNTLKQIASK

LREQFGN#KTIIFKQSSGGDPEFVTHSFNCGGEFFYCDSTQLFDSTWFDSTWS

-continued (b) eOD_VH1-2_v2.0
DTITLPCRPAPPPHCSSNITGLILTRGGGISDDKTEIFRPGGGDMRDIARCQIAGTVVSTQL

LLNGSLAEEEVVIRSEDFRDNSKSICVQLNTSVEINCTGAGHCNISRAKWNNTLKQIASK

LREQFGN#KTIIFSQSLGGDPEFVTHSFNCGGEFFYCDSTQLFDSTWFDSTWS (c) eOD_VH1-2_v2.1 (eOD_VH1-2_v2.0 + D276N + R278T)
DTITLPCRPAPPPHCSSNITGLILTRGGGISDDKTEIFRPGGGDMRDIARCQIAGTVVSTQL

LLNGSLAEEEVVIRSENFTDNSKSICVQLNTSVETNCTGAGHCNISRAKWNNTLKQIASK

LREQFGN#KTIIFSQSLGGDPEFVTHSFNCGGEFFYCDSTQLFDSTWFDSTWS (d) eOD_VH1-2_v3.0 (eOD_VH1-2_v2.0 + G471S + S401#)
DTITLPCRPAPPPHCSSNITGLILTRGGGISDDKTEIFRPSGGDMRDIARCQIAGTVVSTQL

LLNGSLAEEEVVIRSEDFRDNSKSICVQLNTSVEINCTGAGHCNISRAKWNNTLKQIASK

LREQFGN#KTIIFSQSLGGDPEFVTHSFNCGGEFFYCDSTQLFDSTWFDSTW#

(e) eOD_VH1-2-v3.1 (eOD_VH1-2_v2.0 + K357R + S401#)
DTITLPCRPAPPPHCSSNITGLILTRGGGISDDKTEIFRPGGGDMRDIARCQIAGTVVSTQL

LLNGSLAEEEVVIRSEDFRDNSKSICVQLNTSVEINCTGAGHCNISRAKWNNTLKQIASK

LREQFGN#RTIIFSQSLGGDPEFVTHSFNCGGEFFYCDSTQLFDSTWFDSTW#

(f) eOD_VH1-2_v4.0 (eOD_VH1-2_v3.0 + K464D + L260F + K357R)
DTITLPCRPAPPPHCSSNITGLILTRGGGISDDDTEIFRPSGGDMRDIARCQIAGTVVSTQL

FLNGSLAEEEVVIRSEDFRDNSKSICVQLNTSVEINCTGAGHCNISRAKWNNTLKQIASK

LREQFGN#RTIIFSQSLGGDPEFVTHSFNCGGEFFYCDSTQLFDSTWFDSTW#

(g) eOD_VH1-2_v4.1 (eOD_VH1-2_v3.0 + G457A + K464N + I260F + K357R)
DTITLPCRPAPPPHCSSNITGLILTRAGGISDDNTEIFRPSGGDMRDIARCQIAGTVVSTQL

FLNGSLAEEEVVIRSEDFRDNSKSICVQLNTSVEINCTGAGHCNISRAKWNNTLKQIASK

LREQFGN#RTIIFSQSLGGDPEFVTHSFNCGGEFFYCDSTQLFDSTW#

(h) eOD_VH1-2_v4.2 (eOD_VH1-2_v3.0 + K464N + K357R)
DTITLPCRPAPPPHCSSNITGLILTRGGGISDDNTEIFRPSGGDMRDIARCQIAGTVVSTQL

LLNGSLAEEEVVIRSEDFRDNSKSICVQLNTSVEINCTGAGHCNISRAKWNNTLKQIASK

LREQFGN#RTIIFSQSLGGDPEFVTHSFNCGGEFFYCDSTQLFDSTWFDSTW#

(i) eOD_VH1-2_v5.0 (eOD_VH1-2_v4.0 + I460V + E275V + S281A + L365S)
DTITLPCRPAPPPHCSSNITGLILTRGGGVSDDDTEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFSQSSGGDPEFVTHSFNCGGEFFYCDSTQLFDSTWFDSTW#

(j) eOD_VH1-2_v5.1
DTITLPCRPAPPPHCSSNITGLILTRGGGVSDDDTEIFRPAGGDMRDIARCQIAGTVVSTQ

LFLNGSLAEEEVVIRSVDFRDNAKSICVQLNTSVEINCTGAGHCNISRAKWNNTLKQIAS

KLREQFGN#RTIIFSQSSGGDPEFVTHSFNCGGEFFYCDSTQLFDSTWFDSTW#

(k) eOD_VH1-2_v5.2 (truncated form of v5.0)
DTITLPCRPAPPPHCSSNITGLILTRGGGVSDDDTEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFSQSSGGDPEFVTHSFNCGGEFFYCDSTQLFDSTWFD####

(l) eOD_VH1-2_v6.0
DTITLPCRPAPPPHCSSNITGLILTRDGGVSNDETEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCDSTQLFNSTWFNST##

-continued (m) eOD_VH1-2_v6.1 (v6.0 + V460N)
DTITLPCRPAPPPHCSSNITGLILTRDGGNSNDETEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCDSTQLFNSTWFNST##

(n) eOD_VH1-2_v6.2 (v6.0 + T465S)
DTITLPCRPAPPPHCSSNITGLILTRDGGVSNDESEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCDSTQLFNSTWFNST##

(o) eOD_VH1-2_v6.3 (v6.0 + S471G)
DTITLPCRPAPPPHCSSNITGLILTRDGGVSNDETEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCDSTQLFNSTWFNST##

(p) eOD_VH1-2_v6.4 (v6.0 + F260L)
DTITLPCRPAPPPHCSSNITGLILTRDGGVSNDETEIFRPSGGDMRDIARCQIAGTVVSTQL

LLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCDSTQLFNSTWFNST##

(q) eOD_VH1-2_v6.5 (v6.0 + R278T)
DTITLPCRPAPPPHCSSNITGLILTRDGGVSNDETEIFRPSGGDMRDIARCQIAGTVVSTQL

FLNGSLAEEEVVIRSVDFTDNAKSICVQLNTSVEINCTGAGHCNISRAKWNNTLKQIASK

LREQFGN#RTIIFKQSSGGDPEFVTHSFNCGGEFFYCDSTQLFNSTWFNST##

(r) eOD_VH1-2_v6.6 (v6.0 + R357K)
DTITLPCRPAPPPHCSSNITGLILTRDGGVSNDETEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCDSTQLFNSTWFNST##

(s) eOD_VH1-2_v6.7 (v6.0 + F371I)
DTITLPCRPAPPPHCSSNITGLILTRDGGVSNDETEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCDSTQLFNSTWFNST##

(t) eOD_VH1-2_v6.8 (v6.0 "minglyc")
DTITLPCRPAPPPHCSSNITGLILTRDGGVSNDETEIFRPSGGDMRDIARCQIAGTVVSTQL

FLNGSLAEEEVVIRSVDFRDNAKSICVQLDTSVEIDCTGAGHCDISRAKWDNTLKQIASK

LREQFGN#RTIIFKQSSGGDPEFVTHSFNCGGEFFYCDSTQLFNSTWFDST##

(u) eOD_VH1-2_v7.0 (v6.0 + D463N + D386N)
DTITLPCRPAPPPHCSSNITGLILTRDGGVSNNETEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCDSTQLFNSTWFNST##

(v) eOD_VH1-2_v7.1 (v7.0 + V460N)
DTITLPCRPAPPPHCSSNITGLILTRDGGNSNNETEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCNSTQLFNSTWFNST##

(w) eOD_VH1-2_v7.2 (v7.0 + T465S)
DTITLPCRPAPPPHCSSNITGLILTRDGGVSNNESEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCNSTQLFNSTWFNST##

-continued (x) eOD_VH1-2_v7.3 (v7.0 + S471G)
DTITLPCRPAPPPHCSSNITGLILTRDGGVSNNETEIFRPGGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCNSTQLFNSTWFNST##

(y) eOD_VH1-2_v7.4 (v7.0 + F260L)
DTITLPCRPAPPPHCSSNITGLILTRDGGVSNNETEIFRPSGGDMRDIARCQIAGTVVSTQL

LLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCNSTQLFNSTWFNST##

(z) eOD_VH1-2_v7.5 (v7.0 + R278T)
DTITLPCRPAPPPHCSSNITGLILTRDGGVSNNETEIFRPSGGDMRDIARCQIAGTVVSTQL

FLNGSLAEEEVVIRSVDFTDNAKSICVQLNTSVEINCTGAGHCNISRAKWNNTLKQIASK

LREQFGN#RTIIFKQSSGGDPEFVTHSFNCGGEFFYCDSTQLFNSTWFNST##

(aa) eOD_VH1-2_v7.6 (v7.0 + R357K)
DTITLPCRPAPPPHCSSNITGLILTRDGGVSNNETEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#KTIIFKQSSGGDPEFVTHSFNCGGEFFYCNSTQLFNSTWFNST##

(bb) eOD_VH1-2_v7.7 (v7.0 + F371I)
DTITLPCRPAPPPHCSSNITGLILTRDGGVSNNETEIFRPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEIVTHSFNCGGEFFYCNSTQLFNSTWFNST##

(cc) eOD_VH1-2_v7.8 (v7.0 + D276N + R278T)
DTITLPCRPAPPPHCSSNITGLILTRDGGVSNNETEIFRPSGGDMRDIARCQIAGTVVSTQL

FLNGSLAEEEVVIRSVNFTDNAKSICVQLNTSVEINCTGAGHCNISRAKWNNTLKQIASK

LREQFGN#RTIIFKQSSGGDPEFVTHSFNCGGEFFYCNSTQLFNSTWFNST##

(dd) eOD_RheVH1-2_v1.0
DTITLPCRPAPPPHCSSNITGLILTRAGGVSDNNTEIFFPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFSQSTGGDPEFVTHSFNCGGEFFYCDSTQLFNSTWFNST##

(ee) eOD_RheVH1-2_v2.0
DTITLPCRPAPPPHCSSNITGLILGRAGGASDDNTEIFYPSGGDMRDIARCQIAGTVVSTQ

LFLNGSLAEEEVVIRSVDFRDNAKSICVQLNTSVEINCTGAGHCNISRAKWNNTLKQIAS

KLREQFGN#RTIIFSQSTGGDPEIVTHSFNCGGEFFYCNSTQLFNSTWFNST##

(ff) eOD_RheVH1-2_v2.1
DTITLPCRPAPPPHCSSNITGLILTRAGGVSNNETEIFFPSGGDMRDIARCQIAGTVVSTQL

FLNGSLAEEEVVIRSVDFRDNAKSICVQLNTSVEINCTGAGHCNISRAKWNNTLKQIASK

LREQFGN#RTIIFKQSSGGDPEFVTHSFNCGGEFFYCNSTQLFNSTWFNST##

(gg) core_gp120_VH1-2_v1.0
VWKEATTTLFCASDAKAYDTEVHNVWATHACVPTDPNPQEVELENVTENFNMWKNN

MVEQMHEDIISLWDQSLKPCVKLTGGSVITQACPKISFEPIPIHYCAPAGFAILKCKDKKF

NGKGPCSNVSTVQCTHGIRPVVSTQLLLNGSLAEEEVVIRSENFADNAKTIIVQLNESVEI

NCTRPNNGGSGSGGDIRQAHCNLSRAKWNDTLNKIVIKLREQFGNKTIVFKHSSGGDPEI

VTHSFNCGGEFFYCNSTQLFNSTWNVTEESNNTVENNTITLPCRIKQIINMWQKVGRAM

YAPPIRGQIRCSSNITGLLLTRDGGPEDNKTEVFRPGGGDMRDNWRSELYKYKVVKIE (hh) core_gp120_VH1-2_v2.0
VWKDATTTLFCASDAKAHETEVHNVWATHACVPTDPNPQEVELKNVTENFNMWKNN

MVEQMHEDIISLWDQSLKPCVKLTGGSVITQACPKVSFEPIPIHYCAPAGFAILKCKDKK

```
FNGKGPCSNVSTVQCTHGIRPVVSTQLLLNGSLAEEEVVIRSEDFRNNAKIIIVQLNESVEI

NCTGAGHCNLSRAKWNDTLNKIVIKLREQFGNKTIVFKHSSGGDPEIVTHSFNCGGEFFY

CNSTQLFNSTWNVTEESNNTVENNTITLPCRIKQIINMWQEVGRAMYAPPIRGQIRCSSNI

TGLLLIRDGGPEDNKTEIFRPGGGDMRDNWRSELYKYKVVKIE (ii) core_gp120_VH1-2_v2.1
VWKDATTTLFCASDAKAHETEVHNVWATHACVPTDPNPQEVELKNVTENFNMWKNN

MVEQMHEDHSLWDQSLKPCVKLTGGSVITQACPKVSFEPIPIHYCAPAGFAILKCKDKK

FNGKGPCSNVSTVQCTHGIRPVVSTQLLLNGSLAEEEVVIRSEDFRNNAKIIIVQLNESVEI

NCTGAGHCNLSRAKWNDTLNKIVIKLREQFGNKTIVFSHSSGGDPEFVTHSFNCGGEFF

YCNSTQLFNSTWNVTEESNNTVENNTITLPCRIKQIINMWQEVGPIRGQIRCSSNITGLLLI

RDGGAEDNKTEIFRPGGGDMRDNWRSELYKYKVVKIE (jj) full_gp120_BaL_VH1-2_v1.0
MRVKEKYQHLWRWGWRWGTMLLGMLMICSATEKLWVTVYYGVPVWKEATTTLFCA

SDAKAYDTEVHNVWATHACVPTDPNPQEVELENVTENFNMWKNNMVEQMHEDIISL

WDQSLKPCVKLTPLCVTLNCTDLRNATNGNDTNTTSSSREMMGGGEMKNCSFKITTNI

RGKVQKEYALFYELDIVPIDNNSNNRYRLISCNTSVITQACPKISFEPIPIHYCAPAGFAIL

KCKDKKFNGKGPCSNVSTVQCTHGIRPVVSTQLLLNGSLAEEEVVIRSENFADNAKTIIV

QLNESVEINCTRPNNNTRKSIHIGPGRALYTTGEIIGDIRQAHCNLSRAKWNDTLNKIVIK

LREQFGNKTIVFKHSSGGDPEIVTHSFNCGGEFFYCNSTQLFNSTWNVTEESNNTVENNT

ITLPCRIKQIINMWQKVGRAMYAPPIRGQIRCSSNITGLLLTRDGGPEDNKTEVFRPGGG

DMRDNWRSELYKYKVVKIEPLGVAPTKAKRRVVQ (kk) eOD_VH1-2_VH1-8_v1.0
DTITLPCRPAPPPHCSSNITGLILTRLGGVSNDETEIFKPSGGDWRDIARCQIAGTVVSTQL

FLNGSLAEEEVVIRSVDFRDNAKSICVQLNTSVEINCTGAGHCNISRAKWNNTLKQIASK

LREQFGNRTIIFKQSTGGDPEFVTHSFNCGGEFFYCDSTQLFNSTWFNST
``` or any combination thereof.

In a fourth embodiment, the invention relates to a non-naturally occurring protein which may comprise an eOD variant engineered to improve binding to germline VRC01 to eOD which may comprise at least one mutation relative to eOD (=c1d1) in the eOD variants in this section listed below, in both eOD numbering (left column) and HxB2 numbering (right column), wherein the HxB2 numbering uniquely defines a position in any HIV Env sequence once it has been aligned to the HxB2 sequence, wherein the mutation is selected from the table consisting of:

| eOD_mut_id | eOD_numbering | HxB2_numbering |
| --- | --- | --- |
| 1 | A84S | A281S |
| 2 | D27A | D457A |
| 3 | D27G | D457G |
| 4 | E34D | E464D |
| 5 | E34K | E464K |
| 6 | E34N | E464N |
| 7 | G41S | G471S |
| 8 | L63F | L260F |
| 9 | N30A | N460A |
| 10 | N30I | N460I |
| 11 | N30T | N460T |
| 12 | N30V | N460V |
| 13 | N32D | N462D |
| 14 | N33D | N463D |
| 15 | N79D | N276D |
| 16 | N92D | N289D |
| 17 | N98D | N295D |
| 18 | R39F | R469F |
| 19 | R39Y | R469Y |
| 20 | S35T | S465T |
| 21 | T25G | T455G |
| 22 | T81R | T278R |
| 23 | V78E | V275E |
| 24 | I145F | I371F |
| 25 | K131R | K357R |
| 26 | K136S | K362S |
| 27 | N106D | N332D |
| 28 | N113D | N339D |
| 29 | N129D | N355D |
| 30 | N130# | N356# |
| 31 | N160D | N386D |
| 32 | N166D | N392D |
| 33 | N171D | N397D |
| 34 | S139L | S365L |
| 35 | S139T | S365T |
| 36 | S172# | S398# |
| 37 | S175# | S401# |
| 38 | T173# | T399# |
| 39 | W174# | W400# | or any combination thereof.

In a fifth embodiment, the invention relates to a non-naturally occurring protein which may comprise a mutation and/or modification in core_gp120_VH1-2_v2.0 and core_gp120_VH1-2_v2.1 relative to core_gp120_VH1-2_v1.0, wherein the mutation and/or modification improves binding of core gp120 to germline VH1-2 antibodies, wherein the mutation and/or modification is selected from the group consisting of:
(a) removing a glycosylation site at position 276 in any HIV Env construct from any strain
(b) E47D
(c) Y61H
(d) D62E
(e) E87K
(f) I208V
(g) N276D
(h) A278R or T278R
(i) D279N
(j) T283I
(k) Replacement of RPNNGGSGSGGDIRQA with GAG
(l) K362S
(m) I371F
(n) K429E
(o) Deletion of residues 432-437 (RAMYAP)
(p) T455I
(q) V467I
or any combination thereof.

The residue numbering is given in the HxB2 numbering convention commonly used in the field. Preferred embodiments of the invention relate to mutation of any naturally occurring HIV gp120 residue at the positions listed above to arrive at the specific resultant amino acids. Hence, more preferred embodiments of the invention relate to mutation and/or modification in core_gp120_VH1-2_v2.0 and core_gp120_VH1-2_v2.1 relative to core_gp120_VH1-2_v1.0, wherein the mutation and/or modification improves binding of core gp120 to germline VH1-2 antibodies wherein the mutation and/or modification is selected from the group consisting of:
a) removing a glycosylation site at position 276 in any HIV Env construct from any strain
b) mutation to D at position 47
c) mutation to H at position 61
d) mutation to E position 62
e) mutation to K at position 87
f) mutation to V at position 208
g) mutation to D at position 276
h) mutation to R at position 278
i) mutation to N at position 279
j) mutation to I at position 283
k) mutation to S at position 362
l) mutation to F at position 371
m) mutation to E at position 429
n) deletion of residues 432 to 437
o) mutation to I at position 455
p) mutation to I at position 467
or any combination thereof.

In a sixth embodiment, the invention relates to a non-naturally occurring protein which may comprise an eOD variant, wherein the eOD variant is involved in glycan masking, wherein the eOD variant is selected from the group consisting of:

```
(a) "VD(-)" mutations N276D and N463D
(b) eOD_g2
DTITLPCRPAPPPHCSSNITGLILTRDGGNSNNESEIFRPGGGDMRDIANCSIAGTVVSTQL

LLNGSLAEEEVVIRSVNFTDNAKSICVQLNTSVEINCTGAGHCNISRAKWNNTLKQIASK

LREQFGNNKTIIFKQSSGGDPEIVTHSFNCGGEFFYCNSTQLFNSTWFNSTWS (c) eOD_g3
DTITLPCRPAPPPHCSSNITGLILTRDGGNSNNESEIFRPGGGDMRDIARCQNASTVVSTQ

LLLNGSLAEEEVVIRSVNFTDNAKSICVQLNTSVEINCTGAGHCNISRAKWNNTLKQIAS

KLREQFGNNKTIIFKQSSGGDPEIVTHSFNCGGEFFYCNSTQLFNSTWFNSTWS (d) eOD_g4
DTITLPCRPAPPPHCSSNITGLILTRDGGNSNNESEIFRPGGGDMRDIARCQIAGNVTSTQL

LLNGSLAEEEVVIRSVNFTDNAKSICVQLNTSVEINCTGAGHCNISRAKWNNTLKQIASK

LREQFGNNKTIIFKQSSGGDPEIVTHSFNCGGEFFYCNSTQLFNSTWFNSTWS (e) eOD_g5
DTITLPCRPAPPPHCSSNITGLILTRDGGNSNNESEIFRPGGGDMRDIARCQIAGTVVSTQL

LLNGSLAEEEVVIRSVNFTDNAKSICVQLNTSVEINCTGAGHCNISRAKWNNTLKQIASK

LRENFSNNKTIIFKQSSGGDPEIVTHSFNCGGEFFYCNSTQLFNSTWFNSTWS (f) eOD_g6
DTITLPCNPSPPPHCSSNITGLILTRDGGNSNNESEIFRPGGGDMRDIARCQIAGTVVSTQL

LLNGSLAEEEVVIRSVNFTDNAKSICVQLNTSVEINCTGAGHCNISRAKWNNTLKQIASK

LREQFGNNKTIIFKQSSGGDPEIVTHSFNCGGEFFYCNSTQLFNSTWFNSTWS (g) eOD_g7
DTITLPCRNATPPHCSSNITGLILTRDGGNSNNESEIFRPGGGDMRDIARCQIAGTVVSTQ

LLLNGSLAEEEVVIRSVNFTDNAKSICVQLNTSVEINCTGAGHCNISRAKWNNTLKQIAS

KLREQFGNNKTIIFKQSSGGDPEIVTHSFNCGGEFFYCNSTQLFNSTWFNSTWS
```

(h) eOD_g8
DTITLPCRPAPPPHCSSNITGLILTRDGGNSNNESEIFRPGGGDMRDIARCQIAGTVVSTQL

LLNGSLAEEEVVIRSVNFTDNAKSICVQLNTSVEINCTGAGHCNISRAKWNNTLKQIASK

LREQFGNNKTIIFKQSSGGDPEIVTHSFNCGNETFYCNSTQLFNSTWFNSTWS (i) eOD_g3-6-8
DTITLPCNPSPPPHCSSNITGLILTRDGGNSNNESEIFRPGGGDMRDIARCQNASTVVSTQL

LLNGSLAEEEVVIRSVNFTDNAKSICVQLNTSVEINCTGAGHCNISRAKWNNTLKQIASK

LREQFGNNKTIIFKQSSGGDPEIVTHSFNCGNETFYCNSTQLFNSTWFNSTWS (j) eOD_g2-6-8
DTITLPCNPSPPPHCSSNITGLILTRDGGNSNNESEIFRPGGGDMRDIANCSIAGTVVSTQL

LLNGSLAEEEVVIRSVNFTDNAKSICVQLNTSVEINCTGAGHCNISRAKWNNTLKQIASK

LREQFGNNKTIIFKQSSGGDPEIVTHSFNCGNETFYCNSTQLFNSTWFNSTWS (k) eOD_g2-4-6-8
DTITLPCNPSPPPHCSSNITGLILTRDGGNSNNESEIFRPGGGDMRDIANCSIAGNVTSTQL

LLNGSLAEEEVVIRSVNFTDNAKSICVQLNTSVEINCTGAGHCNISRAKWNNTLKQIASK

LREQFGNNKTIIFKQSSGGDPEIVTHSFNCGNETFYCNSTQLFNSTWFNSTWS (l) eOD_g2-5-6-8
DTITLPCNPSPPPHCSSNITGLILTRDGGNSNNESEIFRPGGGDMRDIANCSIAGTVVSTQL

LLNGSLAEEEVVIRSVNFTDNAKSICVQLNTSVEINCTGAGHCNISRAKWNNTLKQIASK

LRENFSNNKTIIFKQSSGGDPEIVTHSFNCGNETFYCNSTQLFNSTWFNSTWS (m) eOD_g2-4-5-6-8
DTITLPCNPSPPPHCSSNITGLILTRDGGNSNNESEIFRPGGGDMRDIANCSIAGNVTSTQL

LLNGSLAEEEVVIRSVNFTDNAKSICVQLNTSVEINCTGAGHCNISRAKWNNTLKQIASK

LRENFSNNKTIIFKQSSGGDPEIVTHSFNCGNETFYCNSTQLFNSTWFNSTWS or any combination thereof.

In a seventh embodiment, the invention relates to a non-naturally occurring protein which may comprise an eOD variant fused with one or more multimerization domains, wherein the eOD variant is selected from the group consisting of:

(a) eOD_VD(-)_3mer_1gcm_1
RMKQIEDKIEEILSKIYHIENEIARIKKLIGERGGSGGSGGDTITLPCRP

APPPHCSSNITGLILTRDGGNSNDESEIFRPGGGDMRDIARCQIAGTVVS

TQLLLNGSLAEEEVVIRSVDFTDNAKSICVQLNTSVEINCTGAGHCNISR

AKWNNTLKQIASKLREQFGNNKTIIFKQSSGGDPEIVTHSFNCGGEFFYC

NSTQLFNSTWFNSTWS (b) eOD_VD(-)_3mer_1gcm_2
DTITILPCRPAPPPHCSSNITGLILTRDGGNSNDESEIFRPGGGDMRDIA

RCQIAGTVVSTQLLLNGSLAEEEVVIRSVDFTDNAKSICVQLNTSVEINC

TGAGHCNISRAKWNNTLKQIASKLREQFGNNKTIIFKQSSGGDPEIVTHS

FNCGGEFFYCNSTQLFNSTWFNSTWSGGSGGSGGRMKQIEDKIEEILSKI

YHTENEIARIKKLIGER (c) eOD_VD(-)_4mer_1gcl_1
RMKQIEDKLEEILSKLYHIENELARIKKLLGERGGSGGSGGDTITLPCRP

APPPHCSSNITGLILTRDGGNSNDESEIFRPGGGDMRDIARCQIAGTVVS

TQLLLNGSLAEEEVVIRSVDFTDNAKSICVQLNTSVEINCTGAGHCNISR

AKWNNTLKQIASKLREQFGNNKTIIFKQSSGGDPEIVTHSFNCGGEFFYC

NSTQLFNSTWFNSTWS (d) eOD_VD(-)_4mer_1gcl_2
DTITLPCRPAPPPHCSSNITGLILTRDGGNSNDESEIFRPGGGDMRDIAR

CQIAGTVVSTQLLLNGSLAEEEVVIRSVDFTDNAKSICVQLNTSVEINCT

GAGHCNISRAKWNNTLKQIASKLREQFGNNKTIIFKQSSGGDPEIVTHSF

NCGGEFFYCNSTQLFNSTWFNSTWSGGSGGSGGRMKQIEDKLEEILSKLY

HIENELARIKELLGER (e) eOD_VD(-)_4mer_2b22_1
MKVKQLEDVVEELLSVNYHLENVVARLKKLVGERSGGSGGSGGGDTITLP

CRPAPPPHCSSNITGLILTRDGGNSNDESEIFRPGGGDMRDIARCQIAGT

VVSTQLLLNGSLAEEEVVIRSVDFTDNAKSICVQLNTSVEINCTGAGHCN

ISRAKWNNTLKQIASKLREQFGNNKTIIFKQSSGGDPEIVTHSFNCGGEF

FYCNSTQLFNSTWFNSTWS (f) eOD_VD(-)_4mer_2b22_2
DTITLPCRPAPPPHCSSNITGLILTRDGGNSNDESEIFRPGGGDMRDIAR

CQIAGTVVSTQLLLNGSLAEEEVVIRSVDFTDNAKSICVQLNTSVEINCT

GAGHCNISRAKWNNTLKQIASKLREQFGNNKTIIFKQSSGGDPEIVTHSF

NCGGEFFYCNSTQLFNSTWFNSTWSGGSGGSGGSGGGMKVKQLEDVVEEL
LSVNYHLENVVARLKKLVGER (g) eOD_VD(-)_8mer_1gc1
DTITLPCRPAPPPHCSSNITGLILTRDGGNSNDESEIFRPGGGDMRDIAR
CQIAGTVVSTQLLLNGSLAEEEVVIRSVDFTDNAKSICVQLNTSVEINCT
GAGHCNISRAKWNNTLKQIASKLREQFGNNKTIIFKQSSGGDPEIVTHSF
NCGGEFFYCNSTQLFNSTWFNSTWSGGSGGSGGSGGGRMKQIEDKLEEIL
SKLYHIENELARIKKLLGERGGSGGSGGSGGGDTITLPCRPAPPPHCSSN
ITGLILTRDGGNSNDESEIFRPGGGDMRDIARCQIAGTVVSTQLLLNGSL
AEEEVVIRSVDFTDNAKSICVQLNTSVEINCTGAGHCNISRAKWNNTLKQ
IASKLREQFGNNKTIIFKQSSGGDPEIVTHSFNCGGEFFYCNSTQLFNST
WFNSTWS (h) eOD_VD(-)_8mer_2b22
DTITLPCRPAPPPHCSSNITGLILTRDGGNSNDESEIFRPGGGDMRDIAR
CQIAGTVVSTQLLLNGSLAEEEVVIRSVDFTDNAKSICVQLNTSVEINCT
GAGHCNISRAKWNNTLKQIASKLREQFGNNKTIIFKQSSGGDPEIVTHSF
NCGGEFFYCNSTQLFNSTWFNSTWSGGSGGSGGSGGGMKVKQLEDVVEEL
LSVNYHLENVVARLKKLVGERGGSGGSGGSGGGDTITLPCRPAPPPHCSS
NITGLILTRDGGNSNDESEIFRPGGGDMRDIARCQIAGTVVSTQLLLNGS
LAEEEVVIRSVDFTDNAKSICVQLNTSNVEINCTGAGHCNISRAKWNNTL
KQIASKLREQFGNNKTIIFKQSSGGDPEIVTHSFNCGGEFFYCNSTQLFN
STWFNSTWS (i) eOD_VD(-)_24mer_3vcd_1
DTITLPCRPAPPPHCSSNITGLILTRDGGNSNDESEIFRPGGGDMRDIAR
CQIAGTVVSTQLLLNGSLAEEEVVIRSVDFTDNAKSICVQLNTSVEINCT
GAGHCNISRAKWNNTLKQIASKLREQFGNNKTIIFKQSSGGDPEIVTHSF
NCGGEFFYCNSTQLFNSTWFNSTWSGGSGGSGGSGGSGGGMSQAIGILEL
TSIAAGMELGDAMLKSANVDLLVSKTISPGKFLLMLGGDIGAIQQAIETG
TSQAGELLVDSLVLANIHPSVLPAISGLNSVDKRQAVGIVETWSVAAAIS
AADRAVKGSDVTLVRVIIMAFGIGGKAYMVVAGDVSDVALAVTVASSSAG
AYGLLVYASLIPRPHEAMWRQMVEG (j) eOD_VD(-)_24mer_3vcd_2
MSQAIGILELTSIAAGMELGDAMLKSANVDLLVSKTISPGKFLLMLGGDI
GAIQQAIETGTSQAGELLVDSLVLANIHPSVLPAISGLNSVDKRQAVGIV
ETWSVAAAISAADRAVKGSDVTLVRVHMAFGIGGKAYMVVAGDVSDVALA
VTVASSSAGAYGLLVYASLIPRPHEAMWRQMVEGGGSGGSGGSGSGGGD
TITLPCRPAPPPHCSSNITGLILTRDGGNSNDESEIFRPGGGDMRDIARC
QIAGTVVSTQLLLNGSLAEEEVVIRSVDFTDNAKSICVQLNTSVEINCTG
AGHCNISRAKWNNTLKQIASKLREQFGNNKTIIFKQSSGGDPEIVTHSFN
CGGEFFYCNSTQLFNSTWFNSTWS (k) eOD_VD(-)_60mer_1hqk_1
MQIYEGKLTAEGLRFGIVASRFNHALVDRLVEGAIDAIVRHGGREEDITL
VRVPGSWEIPVAAGELARKEDIDAVIAIGVLIRGATPHFDYIASEVSKGL
ADLSLELRKPITFGVITADTLEQAIERAGTKHGNKGWEAALSAIEMANLF
KSLRGGSGGSGGSGGSGGGDTITLPCRPAPPPHCSSNITGLILTRDGGNS
NDESEIFRPGGGDMRDIARCQIAGTVVSTQLLLNGSLAEEEVVIRSVDFT
DNAKSICVQLNTSVEINCTGAGHCNISRAKWNNTLKQIASKLREQFGNNK
TIIFKQSSGGDPEIVTHSFNCGGEFFYCNSTQLFNSTWFNSTWS (l) eOD_VD(-)_60mer_1hqk_2
DTITLPCRPAPPPHCSSNITGLILTRDGGNSNDESEIFRPGGGDMRDIAR
CQIAGTVVSTQLLLNGSLAEEEVVIRSVDFTDNAKSICVQLNTSVEINCT
GAGHCNISRAKWNNTLKQIASKLREQFGNNKTIIFKQSSGGDPEIVTHSF
NCGGEFFYCNSTQLFNSTWFNSTWSGGSGGSGGSGGSGGGMQIYEGKLTA
EGLRFGIVASRFNHALVDRLVEGAIDAIVRHGGREEDITLVRVPGSWEIP
VAAGELARKEDIDAVIAIGVLIRGATPHFDYIASEVSKGLADLSLELRKP
ITFGVITADTLEQAIERAGTKHGNKGWEAALSAIEMANLFKSLR (m) eOD_VD(-)_60mer_1hqk_3
MQIYEGKLTAEGLRFGIVASRFNHALVDRLVEGAIDAIVRHGGREEDITL
VRVPGSWEIPVAAGELARKEDIDAVIAIGVLIRGATPHFDYIASEVSKGL
ADLSLELRKPITFGVITADTLEQAIERAGTKHGNKGWEAALSAIEMANLF
KSLRGSQYIKANSKFIGITELSGDTITLPCRPAPPPHCSSNITGLILTRD
GGNSNDESEIFRPGGGDMRDIARCQIAGTVVSTQLLLNGSLAEEEVVIRS
VDFTDNAKSICVQLNTSVEINCTGAGHCNISRAKWNNTLKQIASKLREQF
GNNKTIIFKQSSGGDPEIVTHSFNCGGEFFYCNSTQLFNSTWFNSTWS (n) eOD_VD(-)_60mer_1hqk_4
DTITLPCRPAPPPHCSSNITGLILTRDGGNSNDESEIFRPGGGDMRDIAR
CQIAGTVVSTQLLLNGSLAEEEVVIRSVDFTDNAKSICVQLNTSVEINCT
GAGHCNISRAKWNNTLKQIASKLREQFGNNKTIIFKQSSGGDPEIVTHSF
NCGGEFFYCNSTQLFNSTWFNSTWSGSQYIKANSKFIGITELSGMQIYEG
KLTAEGLRFGIVASRFNHALVDRLVEGAIDAIVRHGGREEDITLVRVPGS
WEIPVAAGELARKEDIDAVIAIGVLIRGATPHFDYIASEVSKGLADLSLE
LRKPITFGVITADTLEQAIERAGTKHGNKGWEAALSAIEMANLFKSLR (o) eOD_VD(-)_180mer_2e0z
VEYFEKLRSALLDGVNKGRSLLKHLPVTRIEGQSFRVDIIKFEDGVRVVK
QEYKPIPLLKKKFYVGIRELNDGTYDVSIATKAGELLVKDEESLVIREIL
STEGIKKMKLSSWDNPEEALNDLMNALQEASDASAGPFGLIINPKRYAKL
LKIYEKSGKMLVEVLKEIFRGGIIVTLNIDENKVIIFANTPAVLDVVVGQ
DVTLQELGPEGDDVAFLVSEAIGIRIKNPEAIVVLEGGSGGSGGSGGSGG
GDTITLPCRPAPPPHCSSNITGLILTRDGGNSNDESEIFRPGGGDMRDIA
RCQIAGTVVSTQLLLNGSLAEEEVVIRSVDFTDNAKSICVQLNTSVEINC
TGAGHCNISRAKWNNTLKQIASKLREQFGNNKTIIFKQSSGGDPEIVTHS
FNCGGEFFYCNSTQLFNSTWFNSTWS or any combination thereof.

The invention also encompasses any HIV Env-based construct or sequence that has been modified with one or more of the mutations described herein to improve binding to germline VH1-2 antibodies like VRC01. The mutations described in this application are in HxB2 numbering and may be made to any HIV Env-based construct or sequence. In a preferred embodiment the HIV Env-based construct or sequence may be derived from gp140 or gp120. In yet another preferred embodiment the germline VH1-2 antibodies may be VRC01.

In an embodiment of the invention, the invention comprises a non-naturally occurring protein comprising any HIV Env-based construct or sequence having improved binding to a germline VH1-2 antibody that has been modified with one or more of the mutations or modifications, wherein the mutation and/or modification is selected from the group consisting of:
- a) removing a glycosylation site at position 276 in any HIV Env construct from any strain
- b) mutation to D at position 47
- c) mutation to H at position 61
- d) mutation to E at position 62
- e) mutation to K at position 87
- f) mutation to V at position 208
- g) mutation to D at position 276
- h) mutation to R at position 278
- i) mutation to N at position 279
- j) mutation to I at position 283
- k) mutation to S at position 362
- l) mutation to F at position 371
- m) mutation to E at position 429
- n) deletion of residues 432 to 437
- o) mutation to I at position 455
- p) mutation to I at position 467 or any combination thereof.

In an embodiment of the invention, the invention comprises a non-naturally occurring protein comprising any HIV Env-based construct or sequence having improved binding to a germline VH1-2 antibody that has been modified with one or more of the mutations or modifications, wherein the mutation and/or modification is selected from the group consisting of:
- (a) removing a glycosylation site at position 276 in any HIV Env construct from any strain
- (b) E47D
- (c) Y61H
- (d) D62E
- (e) E87K
- (f) I208V
- (g) N276D
- (h) A278R or T278R
- (i) D279N
- (j) T283I
- (k) Replacement of RPNNGGSGSGGDIRQA with GAG
- (l) K362S
- (m) I371F
- (n) K429E
- (o) Deletion of residues 432-437 (RAMYAP)
- (p) T455I
- (q) V467I or any combination thereof.

In a still further embodiment of the invention, the invention comprises a non-naturally occurring protein comprising any HIV Env-based construct or sequence having improved binding to a germline VH1-2 antibody comprising a deletion of the glycosylation site at amino acid position 276 and/or deletion of glycosylation sites on the V5 loop at positions 460, 461, 462, or 463.

The invention also encompasses a protein having at least 90% homology or identity with the sequence of the protein of any one of the eOD mutants disclosed herein. The invention also encompasses a protein having at least 95% homology or identity with the sequence of the protein of any one of the eODs disclosed herein.

The invention also encompasses any nucleic acid encoding the protein of any one of the eODs disclosed herein. The invention also encompasses a nucleic acid having at least 90% or 95% homology or identity with the sequence of said nucleic acid.

The present invention also encompasses methods for eliciting an immune response which may comprise systemically administering to an animal in need thereof an effective amount of the protein of any one of the eODs disclosed herein. The animal may be a mammal, advantageously a human.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed. description, given by way of example, but not intended to limit the invention solely to the specific embodiments described, may best be understood in conjunction with the accompanying drawings.

DETAILED DESCRIPTION OF THE INVENTION

Figure 1A:
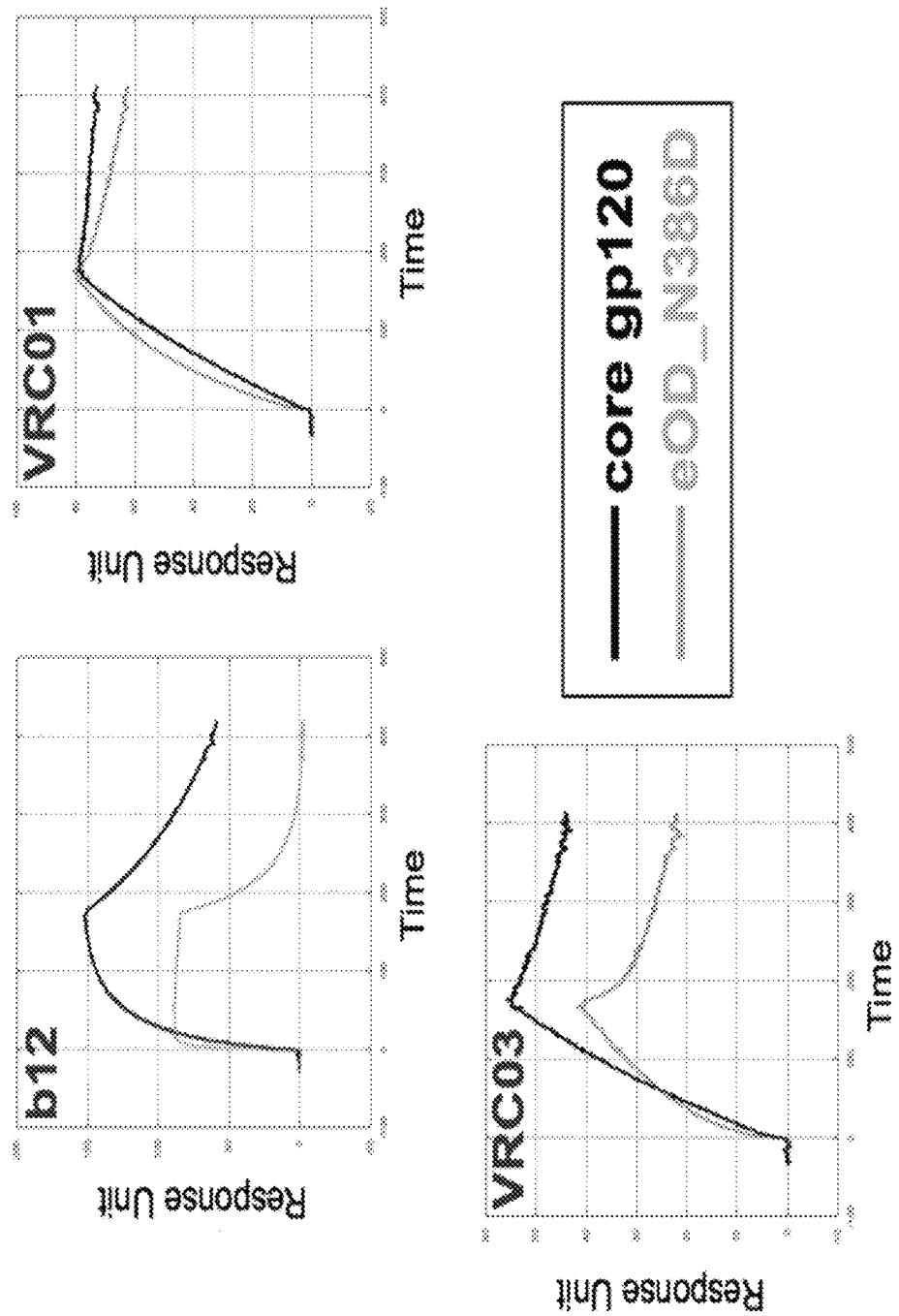
FIG. 1A depicts a binding specificity evaluation. The binding specificity of c1d1_N386D and core gp120 is compared against with a panel of CD4bs-directed antibodies and CD4-IgG2. The CD4bs-directed antibodies tested included the broadly neutralizing antibodies b12, VRC01 and VRC03, and the non-neutralizing antibodies b13, m14, m18, F105, and 15e. In this experiment, each antibody (and CD4-IgG2) was captured on the SPR sensor chip, and c1d1 and gp120 constructs were flowed as analytes. gp120 was used at a concentration of 100 nM, while the c1d1 was used at a concentration of 1 µM. The results show that c1d1 binds only to the neutralizing CD4bs antibodies, while gp120 binds to CD4 and all antibodies tested.
Figure 1B:
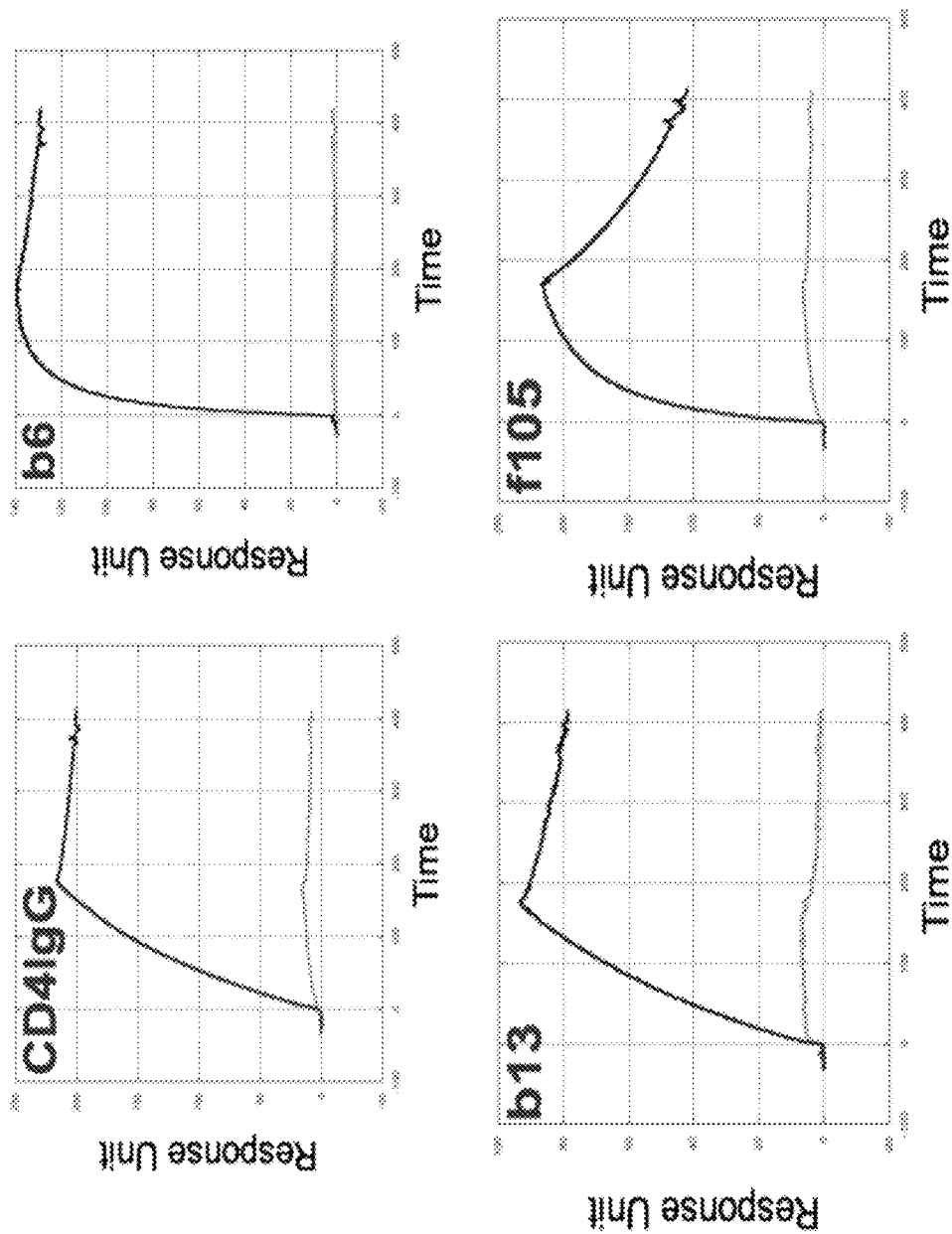
FIG. 1B depicts a binding specificity evaluation. The binding specificity of c1d1_N386D and core gp120 is compared against with a panel of CD4bs-directed antibodies and CD4-IgG2. The CD4bs-directed antibodies tested included the broadly neutralizing antibodies b12, VRC01 and VRC03, and the non-neutralizing antibodies b13, m14, m18, F105, and 15e. In this experiment, each antibody (and CD4-IgG2) was captured on the SPR sensor chip, and c1d1 and gp120 constructs were flowed as analytes. gp120 was used at a concentration of 100 nM, while the c1d1 was used at a concentration of 1 μM. The results show that c1d1 binds only to the neutralizing CD4bs antibodies, while gp120 binds to CD4 and all antibodies tested.
Figure 1C:
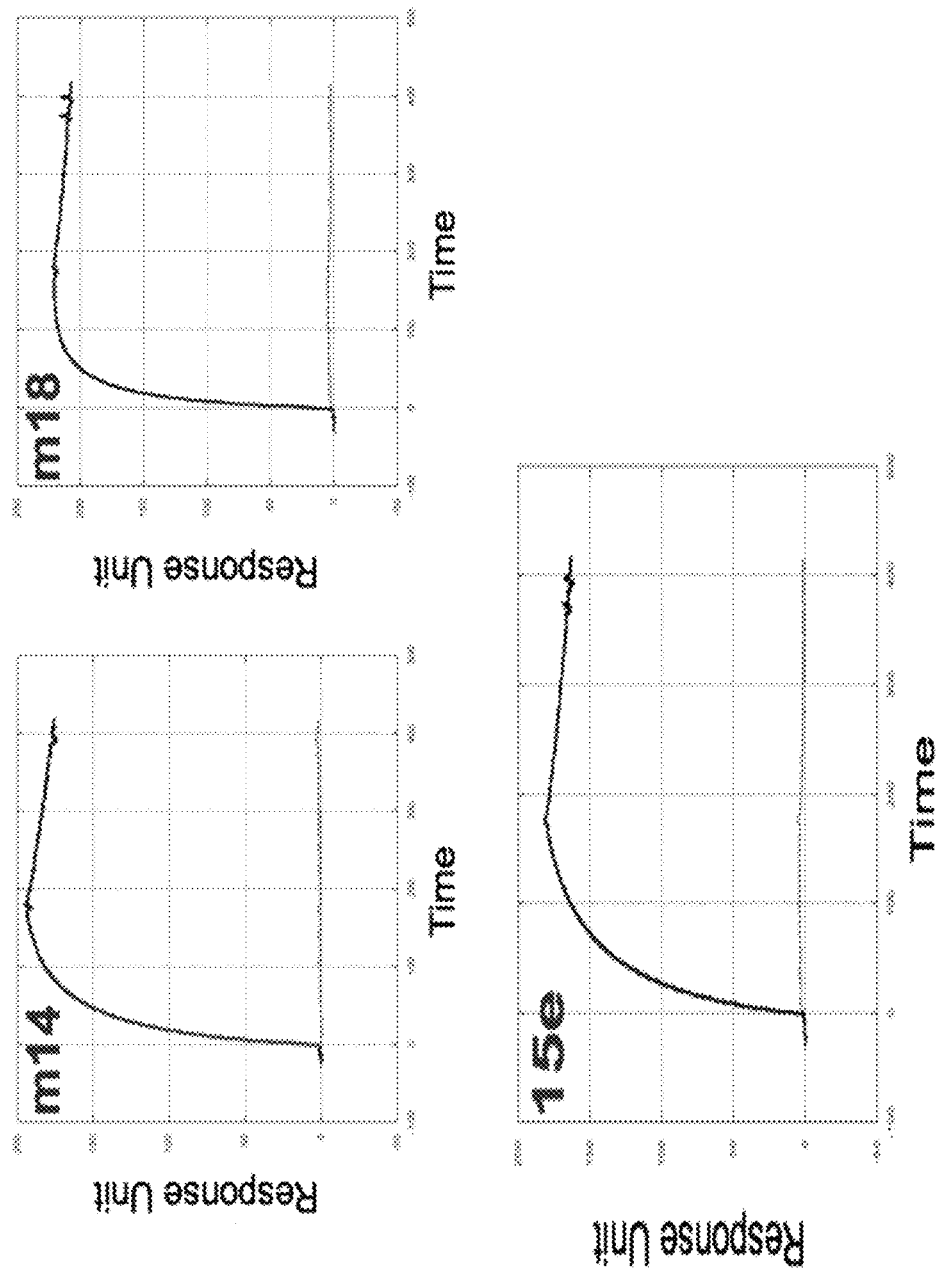
FIG. 1C depicts a binding specificity evaluation. The binding specificity of c1d1_N386D and core gp120 is compared against with a panel of CD4bs-directed antibodies and CD4-IgG2. The CD4bs-directed antibodies tested included the broadly neutralizing antibodies b12, VRC01 and VRC03, and the non-neutralizing antibodies b13, m14, m18, F105, and 15e. In this experiment, each antibody (and CD4-IgG2) was captured on the SPR sensor chip, and c1d1 and gp120 constructs were flowed as analytes. gp120 was used at a concentration of 100 nM, while the c1d1 was used at a concentration of 1 μM. The results show that c1d1 binds only to the neutralizing CD4bs antibodies, while gp120 binds to CD4 and all antibodies tested.

The invention pertains to the identification, design, synthesis and isolation of mutant eOD proteins disclosed herein as well as nucleic acids encoding the same. The present invention also relates to homologues, derivatives and variants of the sequences of the mutant eOD proteins and nucleic acids encoding the same, wherein it is preferred that the homologue, derivative or variant have at least 50%, at least 60%, at least 70%, at least 75%, at least 80%, at least 85%, at least 90%, at least 93%, at least 95%, at least 97%, at least 98% or at least 99% homology or identity with the sequence of the mutant eOD proteins and nucleic acids encoding the same. It is noted that within this specification, homology to sequences of the mutant proteins and nucleic acids encoding the same refers to the homology of the homologue, derivative or variant to the binding site of the mutant proteins and nucleic acids encoding the same.

The invention still further relates to nucleic acid sequences expressing the mutant eOD proteins disclosed herein, or homologues, variants or derivatives thereof. One of skill in the art will know, recognize and understand techniques used to create such. Additionally, one of skill in the art will be able to incorporate such a nucleic acid sequence into an appropriate vector, allowing for production of the amino acid sequence of mutant proteins and nucleic acids encoding the same or a homologue, variant or derivative thereof.

Where used herein and unless specifically indicated otherwise, the following terms are intended to have the following meanings in addition to any broader (or narrower) meanings the terms might enjoy in the art:

The term "isolated" or "non-naturally occurring" is used herein to indicate that the isolated moiety (e.g. peptide or compound) exists in a physical milieu distinct from that in which it occurs in nature. For example, the isolated peptide may be substantially isolated with respect to the complex cellular milieu in which it naturally occurs. The absolute level of purity is not critical, and those skilled in the art may readily determine appropriate levels of purity according to the use to which the peptide is to be put. The term "isolating" when used a step in a process is to be interpreted accordingly.

In many circumstances, the isolated moiety will form part of a composition (for example a more or less crude extract containing many other molecules and substances), buffer system, matrix or excipient, which may for example contain other components (including proteins, such as albumin).

In other circumstances, the isolated moiety may be purified to essential homogeneity, for example as determined by PAGE or column chromatography (for example HPLC or mass spectrometry). In preferred embodiments, the isolated peptide or nucleic acid of the invention is essentially the sole peptide or nucleic acid in a given composition.

The proteins and compounds of the invention need not be isolated in the sense defined above, however.

The term "pharmaceutical composition" is used herein to define a solid or liquid composition in a form, concentration and level of purity suitable for administration to a patient (e.g. a human patient) upon which administration it may elicit the desired physiological changes. The terms "immunogenic composition" and "immunological composition" and "immunogenic or immunological composition" cover any composition that elicits an immune response against the targeted pathogen, HIV. Terms such as "vaccinal composition" and "vaccine" and "vaccine composition" cover any composition that induces a protective immune response against the targeted pathogen or which efficaciously protects against the pathogen; for instance, after administration or injection, elicits a protective immune response against the targeted pathogen or provides efficacious protection against the pathogen. Accordingly, an immunogenic or immunological composition induces an immune response, which may, but need not, be a protective immune response. An immunogenic or immunological composition may be used in the treatment of individuals infected with the pathogen, e.g., to stimulate an immune response against the pathogen, such as by stimulating antibodies against the pathogen. Thus, an immunogenic or immunological composition may be a pharmaceutical composition. Furthermore, when the text speaks of "immunogen, antigen or epitope", an immunogen may be an antigen or an epitope of an antigen. A diagnostic composition is a composition containing a compound or antibody, e.g., a labeled compound or antibody, that is used for detecting the presence in a sample, such as a biological sample, e.g., blood, semen, vaginal fluid, etc, of an antibody that binds to the compound or an immunogen, antigen or epitope that binds to the antibody; for instance, an anti-HIV antibody or an HIV immunogen, antigen or epitope.

A "conservative amino acid change" is one in which the amino acid residue is replaced with an amino acid residue having a similar side chain. Families of amino acid residues having similar side chains have been defined in the art. These families include amino acids with basic side chains (e.g. lysine, arginine and histidine), acidic side chains (e.g. aspartic acid and glutamic acid), non-charged amino acids or polar side chains (e.g. glycine, asparagine, glutamine, serine, threonine, tyrosine and cysteine), non-polar side chains (e.g. alanine, valine, leucine, isoleucine, proline, phenylalanine, methionine and tryptophan), beta-branched side chains (e.g. threonine, value and isoleucine), and aromatic side chains (e.g. tyrosine, phenylalanine, tryptophan and histidine).

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, $F(ab')_2$, Fv and scFV which are capable of binding the epitope determinant. These antibody fragments retain some ability to selectively bind with its antigen or receptor and include, for example:

(a) Fab, the fragment which contains a monovalent antigen-binding fragment of an antibody molecule may be produced by digestion of whole antibody with the enzyme papain to yield an intact light chain and a portion of one heavy chain;

(b) Fab', the fragment of an antibody molecule may be obtained by treating whole antibody with pepsin, followed by reduction, to yield an intact light chain and a portion of the heavy chain; two Fab' fragments are obtained per antibody molecule;

(c) $F(ab')_2$, the fragment of the antibody that may be obtained by treating whole antibody with the enzyme pepsin without subsequent reduction; $F(ab')_2$ is a dimer of two Fab' fragments held together by two disulfide bonds;

(d) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference). Fabs, Fv and scFV may also be made recombinantly, i.e. expressed as Fab, Fv or scFV rather than cleaving an intact IgG.

A "neutralizing antibody" may inhibit the entry of HIV-1 virus for example SF162 and/or JR-CSF with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

An "isolated antibody" or "non-naturally occurring antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment not be present. Ordinarily, however, isolated antibody will be prepared by at least one purification step.

The term "monoclonal antibody" as used herein refers to an antibody obtained from a population of substantially homogeneous antibodies, i.e., the individual antibodies which may comprise the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

An "antibody fragment" may comprise a portion of an intact antibody, preferably the antigen binding or variable region of the intact antibody. Examples of antibody fragments include Fab, Fab', F(ab')$_2$, scFV and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

It should be understood that the proteins, including the antibodies of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine, (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated or non-naturally occurring replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double-stranded (duplex). Duplex nucleic acids may be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the sequences of the invention, such as the mutant eOD proteins, may be altered in these ways.

As regards codon optimization, the nucleic acid molecules of the invention have a nucleotide sequence that encodes the antigens of the invention and may be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens may be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention may readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990, 87:

2264-2268, modified as in Karlin & Altschul, Proc. Natl. Acad. Sci. USA 1993;90: 5873-5877.

Another example of a mathematical algorithm used for comparison of sequences is the algorithm of Myers & Miller, CABIOS 1988;4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 may he used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms may be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies of the present invention may be used in accordance with the present invention. In certain embodiments, the antibodies of the present invention may be used in vitro (such as using cell-free expression systems) and/or in cultured cells grown in vitro in order to produce the encoded HIV-antibodies, which may then be used for various applications such as in the production of proteinaceous vaccines. For such applications, any vector that allows expression of the antibodies in vitro and/or in cultured cells may be used.

For applications where it is desired that the antibodies be expressed in vivo, for example when the transgenes of the invention are used in DNA or DNA-containing vaccines, any vector that allows for the expression of the antibodies of the present invention and is safe for use in vivo may be used. In preferred embodiments the vectors used are safe for use in humans, mammals and/or laboratory animals.

For the antibodies of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" may be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention may be under the control of a constitutive promoter or of an inducible promoter, which initiates transcription only when exposed to some particular external stimulus, such as, without limitation, antibiotics such as tetracycline, hormones such as ecdysone, or heavy metals. The promoter may also be specific to a particular cell-type, tissue or organ. Many suitable promoters and enhancers are known in the art, and any such suitable promoter or enhancer may be used for expression of the transgenes of the invention. For example, suitable promoters and/or enhancers may be selected from the Eukaryotic Promoter Database (EPDB).

The vectors used in accordance with the present invention should typically be chosen such that they contain a suitable gene regulatory region, such as a promoter or enhancer, such that the antibodies of the invention may be expressed.

For example, when the aim is to express the antibodies of the invention in vitro, or in cultured cells, or in any prokaryotic or eukaryotic system for the purpose of producing the protein(s) encoded by that antibody, then any suitable vector may be used depending on the application. For example, plasmids, viral vectors, bacterial vectors, protozoal vectors, insect vectors, baculovirus expression vectors, yeast vectors, mammalian cell vectors, and the like, may be used. Suitable vectors may be selected by the skilled artisan taking into consideration the characteristics of the vector and the requirements for expressing the antibodies under the identified circumstances.

In an advantageous embodiment, IgG1 and Fab expression vectors may be utilized to reconstitute heavy and light chain constant regions if heavy and light chain genes of the antibodies of the present invention are cloned.

When the aim is to express the antibodies of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies of the invention in a laboratory animal, such as for pre-clinical testing of the HIV-1 immunogenic compositions and vaccines of the invention. In other embodiments, it will be desirable to express the antibodies of the invention in human subjects, such as in clinical trials and for actual clinical use of the immunogenic compositions and vaccine of the invention. Any vectors that are suitable for such uses may be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA: ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and may be used as gene delivery vectors.

The nucleotide sequences and vectors of the invention may be delivered to cells, for example if the aim is to express the HIV-1 antigens in cells in order to produce and isolate the expressed proteins, such as from cells grown in culture. For expressing the antibodies in cells any suitable transfection, transformation, or gene delivery methods may be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies may be carried out in any suitable type of host cells, such as bacterial cells, yeast, insect cells, and mammalian cells. The antibodies of the invention may also be expressed using including in vitro transcription/translation systems. All of such methods are well known by those skilled in the art, and one of skill in the art would readily be able to select a suitable method depending on the nature of the nucleotide sequences, vectors, and cell types used.

A synthetic mutant eOD may be chemically synthesized in whole or part using techniques that are well-known in the art (see, e.g., Kochendoerfer, G. G., 2001). Additionally, homologs and derivatives of the polypeptide may be also be synthesized.

Alternatively, methods which are well known to those skilled in the art may be used to construct expression vectors containing nucleic acid molecules that encode the polypeptide or homologs or derivatives thereof under appropriate trascriptional/translational control signals, for expression. These methods include in vitro recombinant DNA techniques, synthetic techniques and in vivo recombination/genetic recombination. See, for example, the techniques described in Maniatis et al., 1989.

The outer domain of HIV gp120 contains the CD4-binding site (CD4bs), one of the most important targets for broadly-neutralizing antibodies (bnAbs) and therefore one of the most important targets for HIV vaccine design. Hence the outer domain is an attractive antigen for elicitation of bnAbs. However, when expressed as a protein domain alone, the outer domain (typically HIV gp120 residues 252-482 in HxB2 numbering) has reduced affinity for CD4bs-directed bnAbs like b12 and VRC01, compared to full-length gp120 or core gp120. The outer domain also includes the V3 loop and the beta 20/21 hairpin, both of which could distract immune responses away from the CD4bs. Finally, the outer domain has a tendency to aggregate in solution.

Using a combination of computational design and yeast-display screening, Applicants have engineered variants of the outer domain by a variety of steps including: circular permutation, addition of novel disulfides, replacing loops with optimal shorter loops, removing glycans, improving core packing and altering the location of an internal helix.

By these modifications, Applicants have engineered variants of the outer domain that have several features likely to be advantageous for the elicitation of CD4bs-directed bnAbs. Variants of Applicants' engineered outer domain: (a) maintain high affinity for broadly neutralizing antibodies b12 and VRC01 (b) bind with little or no detectable affinity to CD4 or non-neutralizing CD4bs antibodies such as b6, b13, F105, 15e, m14 or m18 (c) lack the V3 loop and beta20/21 hairpin and are minimal in size (~175 residues compared to ~230 for wild-type outer domain) (d) display no evidence of aggregation (e) have N and C termini located distal from the CD4bs to allow coupling, by chemical or genetic means, to larger particles for the purpose of multimeric display (f) can be expressed with a minimum of only 2 glycans which could be useful for manipulating immune responses.

Yeast Display of HIV gp120 and Outer Domain Variants.

To establish a platform for optimizing the antibody-binding of designed outer domains, Applicants adapted yeast surface display methods for screening Applicants' constructs. Applicants are not aware of prior reports of successful yeast display experiments of gp120. Indeed, core gp120 (sequence from PDBcode 1RZJ) displayed on the yeast surface shows significantly reduced binding to b12 compared to mammalian-expressed soluble g120. *Saccharomyces cerevisiae* makes polymannose-type glycans that are approximately ten times longer than mammalian glycans, and Applicants hypothesized that the presence of these long glycans interfered with the binding of b12 to gp120 displayed on yeast. Three core gp120 sequences (all based on the HxB2 core gp120 in PDB ID: 1RZJ) Applicants rebuilt to examine the steric effect of the glycans present: wildtype core gp120, core gp120 with all the known N-linked glycosylation sites near the CD4bs mutated (called "gp120_partial_glycan_deletion", this construct was the 1RZJ gp120 sequence but with N->D mutations at all of the following positions in HxB2 numbering: 197, 276, 339, 392, 463), and core gp120 mutating only the asparagine residue at position 386 to aspartic acid [called "gp120 (N386D)"]. In yeast display experiments testing the binding to b12 IgG for these three constructs, Applicants found that the single N386D mutation sufficed to recover high affinity b12 binding to gp120. All subsequent outer domain constructs included the N386D mutation unless otherwise noted.

Initial Construct: OD(D386).

Figure 2:
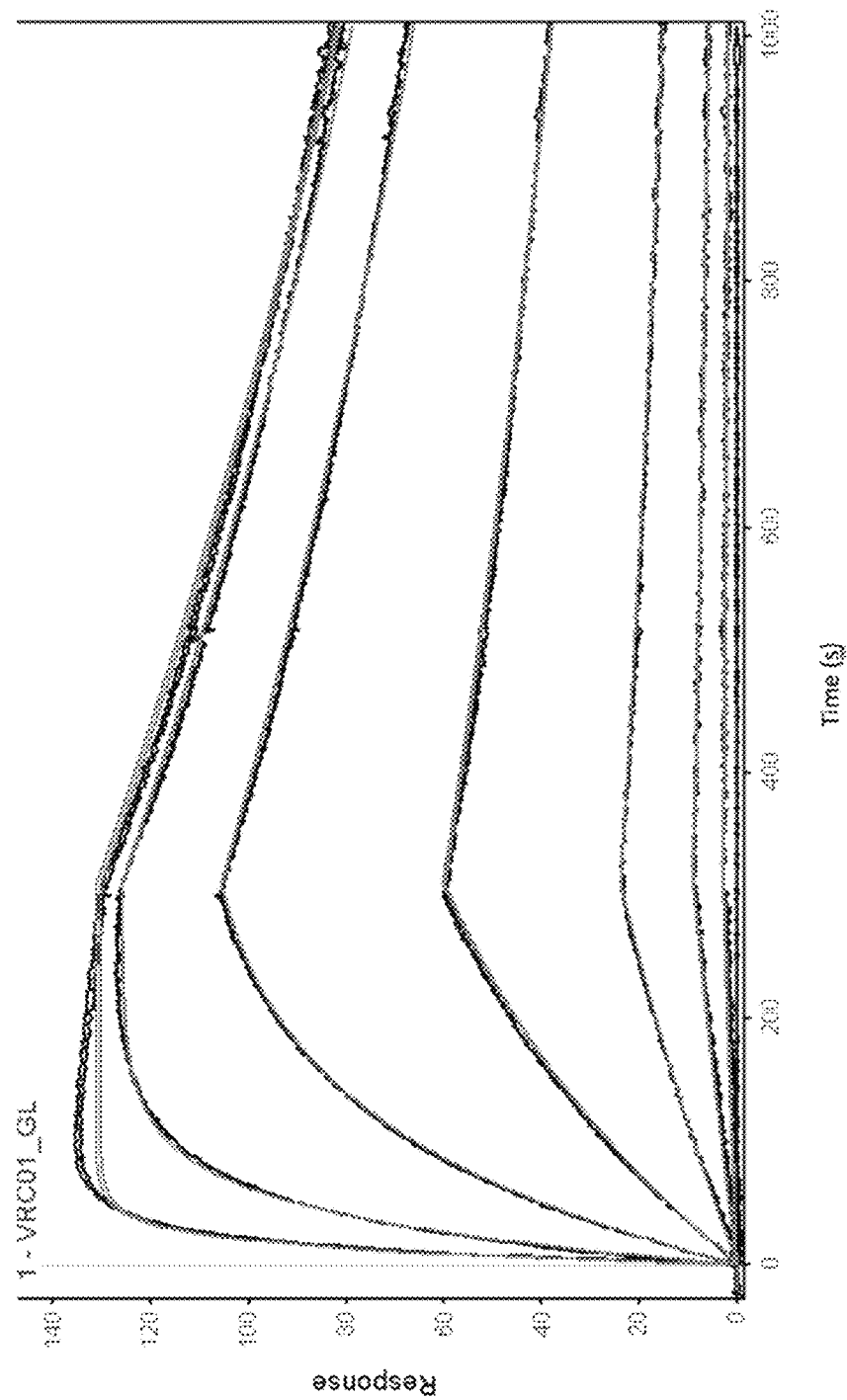
FIG. 2 depicts SPR data and fit for eOD_VH1-2_v6.0 binding to germline VRC01. VRC01_GL IgG was captured on the sensor surface by anti-human IgG; eOD_VH1-2_v6.0 was flowed as analyte at the following concentrations: 6.9 nM, 20.6 nM, 61.7 nM, 185.2 nM, 555.6 nM, 1.67 mcM, 5.0 mcM. The kinetic fit to the data using a 1:1 binding model gives kon=1.57×104 s−1M−1, koff=6.83×10−4 s−1, and KD=koff/kon=43.6 nM.
Figure 3:
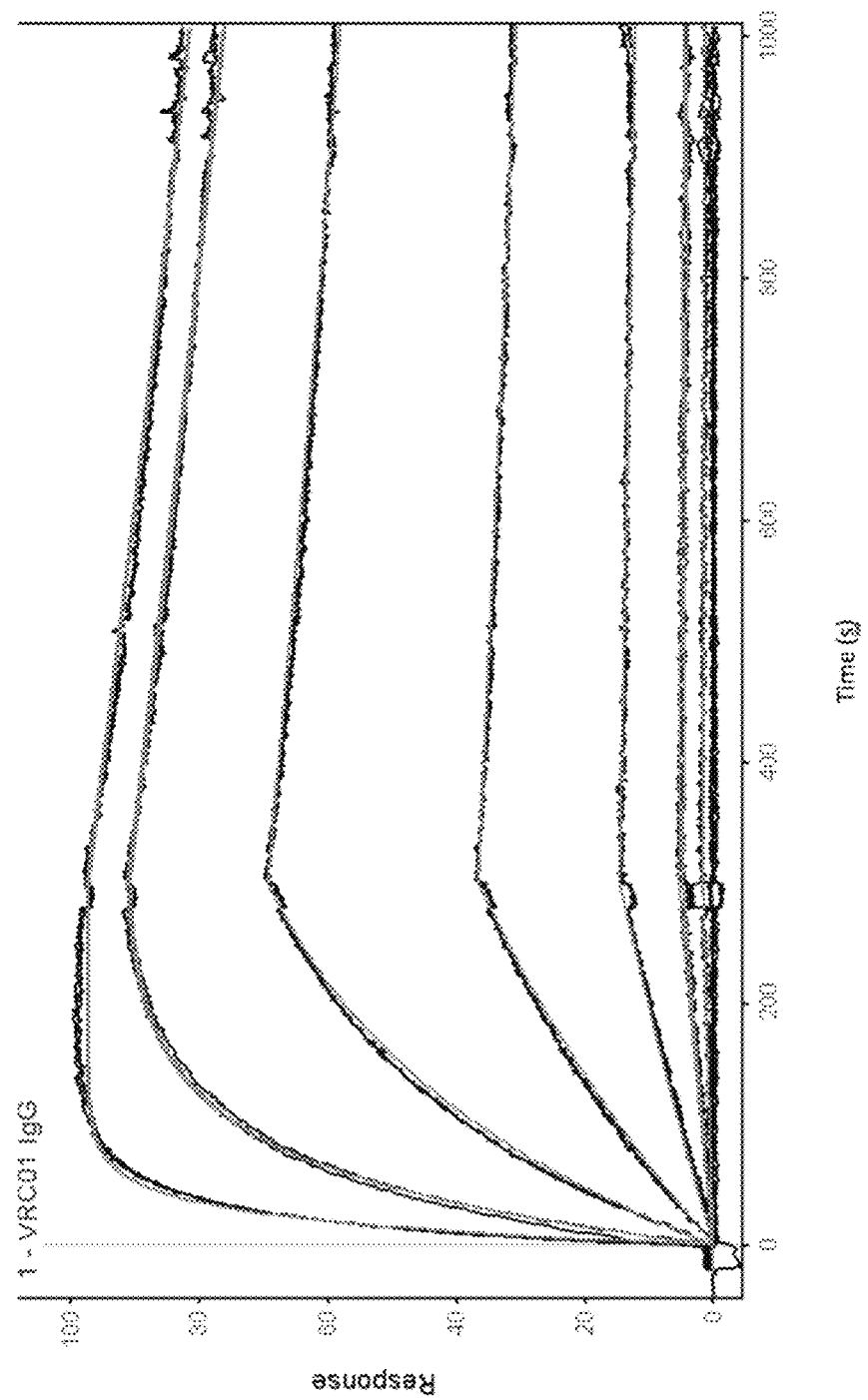
FIG. 3 depicts SPR data and fit for eOD_VH1-2_v6.0 binding to mature VRC01. VRC01 IgG was captured on the sensor surface by anti-human IgG; eOD_VH1-2_v6.0 was flowed as analyte at the following concentrations: 457 pM, 1.37 nM, 4.11 nM, 12.3 nM, 37.0 nM, 111 nM, 333 nM. The kinetic fit to the data using a 1:1 binding model with mass-transport gives $k_{on}=1.48 \times 10^5$ $s^{-1}M^{-1}$, $k_{off}=2.509 \times 10^{-4} s^{-1}$, and $K_D=k_{off}/k_{on}=1.7$ nM.

Applicants' starting point, "OD(D386)", for design of engineered outer domains was based on the outer domain construct "OD1" described by Yana et al. (Yang et al. J. Virol 78:12975-12986 (2004)), but contained a number of differences. Yang et al. stated that their OD1 sequence boundaries included residues "252RPVVS . . . " to ". . . DNWRS482", but Applicants used "252RPVVS . . . " to ". . . DNWRSE482" which included an additional glutamic acid at the C-terminus. In HxB2 numbering [FIG. 2d in Kwong et al. Nature 393:648-659 (1998)], the Yang OD1 construct included residues 252-481, while Applicants' sequence includes residues 252-482. The Yang et al. OD1 was based on the HIV YU2 strain, but Applicants utilized the HxB2 strain because a variant of that strain had been crystallized in complex with the broadly neutralizing antibody b12 (PDB ID:2ny7). The Yang et al. OD1 included the V3 loop, but Applicants used the V3 loop truncation included in the core gp120 construct crystallized with b12 ("CTGAGHC" was used in place of "CTRPNNNTRKRIRIQRGPGRAFVTIG-KIGNMRQAHC"). Finally, Applicants added the N386D mutation to eliminate a glycosylation site near the b12-epitope as noted above, and Applicants added a c-terminal his-tag for purification. A C-terminal his tag was included in all subsequent constructs unless otherwise noted. OD(D386) was expressed and purified from mammalian (293) cells and its binding affinity for b12 assessed by Surface Plasmon Resonance (SPR). The $K_D$ was 1600 nM with b12 IgG captured on the sensor surface and OD(D386) flowing as analyte. In comparison, the $K_D$ measured for core gp120 was 4.5 nM measured using the same format.

TABLE 1

Dissociation constants ($K_D$s) for b12 and VRC01 binding, measured by Surface plasmon resonance (SPR), Isothermal titration calorimetry (ITC), and titrations of Fab binding to proteins displayed on the yeast cell surface

| protein name | Alternate name | $K_D$ for b12 (nM) | KD for vrc01 (nM) |
|---|---|---|---|
| GP120core | | 4.5 | 3.9 |
| OD(D386) | | 1600 | — |
| ODml(N386) | | 1900 | 298 |
| ODml | | 530 | — |
| ODml(d1disulf) | | 175 | — |
| c1 | | 140 | — |
| c2 | | 127 | 90/156† |
| c1d1_N386D | eOD N386D | 59/65†/21* | 139/200†/>50* |
| c1d1_b10disulf | | 200 | 100†/>50* |
| c1d1_v2 | | 30/11* | 249/100†/>50* |
| c1d1_minglyc | eODminglyc | 31 | 7.5 |
| c1d1_b20/21 | | 120 | — |
| c2d1 | | 25 | — |
| c2d2 | | 68 | — |
| c2d1_b10disulf | | 148 | 289 |

SPR values have neither † nor *
†ITC
*yeast Fab titration

Optimization 1: Truncation of the Beta20/21 Loop Region to Produce "ODml".

Applicants' first optimization step focused on trimming the beta20/21 loop region (HxB2 residues 419-444), because this loop did not appear important for b12 binding in the b12-gp120 crystal structure (PDB ID:2ny7), because Applicants suspected that this loop may contain distracting epitopes, and because Applicants hypothesized that a shortened loop may improve the conformational rigidity of the outer domain. To maintain structural integrity, new loops of various lengths Applicants rebuilt computationally using RosettaRemodel (Huang et al. PlosOne 6(8): e24109 (2011)) to identify the minimum lengths that would fit between two disulfide bands (C418-C385 and C378-C445) that bound this region. The computational analysis predicted that loops of length 6, 7, or 8 would be optimal.

Libraries containing 6, 7 or 8 residues in the beta20/21 region of OD(D386) were constructed for screening via yeast display. The libraries were constructed by taking the best 50 computational designs ranked by score for each loop length, constructing a sequence profile of for each set of 50 designs, and employing degenerate codons to span the complexity at each variable position. The codons used for the three different libraries were: (DHK DST NNW NNT NNW NNW), (VNW NNT NVW NVT NNT NNW NVW), and (DDD NNT NNK NNK NNK NNK NNW NNT). The resultant libraries were assembled by overlapping oligos designed with PRIDE (software written by Po-Ssu Huang, http://thesis.library.caltech.edu/2354/ pages 154-172), with single oligos spanning the loop region carrying degenerate codons. Each of the libraries was synthesized separately by polymerase chain reaction, but transformed into yeast (yeast display strain EBY100) as a mixture. Integration of the library into pCTCON2 was carried out by yeast homologous recombination. The resulting final library had a theoretical complexity greater than 109 but was sorted on yeast initially with only ~$3.5\times10^7$ cells. The library was sorted for b12 IgG binding for 5 rounds, with the final b12 IgG concentration at 1 nM and converged on two unique clones with loop lengths of 6 and 7 with the sequences of KGGRPG and IPKRDFN, respectively between C418 and C445. The 6-residue loop showed better affinity for b12 IgG through titration.

Based on that result, a second library of length 6 was constructed; this library further required arginine at position 419, to ensure maintenance of a potentially important cation-π stacking interaction with W100 on the HCDR3 loop of b12; the five other positions in the library used the degenerate codon NNT which allowed the following amino acids: FSTNYVCLAPHDRIG. The theoretical library size was 759,375 and was sorted initially with ~$3\times10^7$ cells. After six rounds of yeast display selection for b12 binding at successive concentrations of 250 nM, 1 nM, 300 pM, 100 pM, 30 pM and 10 pM b12 IgG, Applicants enriched one clone from the arginine-restricted library that significantly improved binding to b12. The selected loop in this clone had the sequence "RPAPPPH" to replace the wild-type b20/21 loop region of "RIKQIINMWQKVGKAMYAPPISGQIR" between C418 and C445 (Note that the selected loop had a length of 7; this was likely due to an oligo synthesis error because the library was built with oligos specifying length 6 loops only.). The selected praline-rich loop sequence may lend rigidity to the structure. Comparisons of b12 IgG binding on the yeast surface between the clone with the RPAPPPH loop and the clone with the KGGRPG loop indicated that the RPAPPPH loop conferred higher binding avidity. The selected RPAPPPH loop was incorporated into subsequent engineered outer domain designs, and Applicants note that this loop might be useful for stabilization of other gp120-based constructs. The outer domain construct containing this loop (but otherwise based on OD(D386) above) was called "ODml".

By SPR, ODml expressed and purified from mammalian cells bound to b12 with $K_D$ of 530 nM, an improvement over OD(D386) by a factor of approximately three (Table 1). A variant "ODml(N386)" was produced containing asparagine at 386 thus restoring the glycosylation site at that position; ODml(N386) bound to b12 with a $K_D$ of approximately 1900 nM by SPR, indicating that the presence of a glycan at 386 significantly reduces b12 affinity for mammalian cell-produced ODml.

ODml and ODml(N386) were evaluated for VRC01 binding by SPR. The kinetics for ODml could not be fit with a simple binding model. The Kd for ODml(N386) was found to be 298 nM (Table 1). In comparison, the Kd for core gp120 binding to VRC01 was 3.9 nM.

Optimization 2: Addition of a Novel Disulfide Bond to Produce "ODml(d1 disulf)".

The structure of the outer domain in b12-bound gp120 was screened computationally for additional disulfide placements that might stabilize the structure. In particular, Applicants sought to stabilize the position of the alpha5 helix at the c-terminus of the ODml, because this helix leads from the "outer domain exit loop" (residues 472-475) that makes important contacts to b12. In full-length or core gp120, the position and conformation of the alpha5 helix is stabilized by extensive contacts to the inner domain, but those contacts are missing in outer domain constructs. Applicants hypothesized that a disulfide bond between the alpha5 helix and another position on the outer domain itself might anchor the helix position and hence stabilize the conformation of the outer domain exit loop.

Fixed backbone analysis of the 2ny7 structure analyzed candidate disulfides based on the following backbone geometry parameters: (a) Cbeta1-Cbeta2 distance (b) Calpha1-Cbeta1-Cbeta2 and Calpha2-Cbeta2-Cbeta1 "bond angles" (c) Calpha1-Cbeta1-Cbeta2-Calpha2 "bond dihedral", and also based on the fractional buried surface area of the native sidechains at the positions considered for mutation to cysteine. Of several candidate disulfides suggested by this analysis, two involved the alpha5 helix: 283-477 and 285-481. Independently, explicit flexible backbone disulfide design using RosettaRemodel (Huang et al. PlosOne 6(8): e24109 (2011)) was employed to search for candidate disulfides without pre-specifying the cysteine pairs; RosettaRemodel also identified the two disulfides above, and the designs suggested that no additional mutations were necessary to accommodate either disulfide, ODml with disulfides at either 283-477 or 285-481 were tested for b12 binding on the surface of yeast, and the 285-481 disulfide conferred tighter binding. Hence the 285-481 disulfide was selected for further analysis.

ODml(d1 disulf) was expressed and purified from mammalian cells, and binding to b12 was assessed by SPR. The $K_D$ for b12 was 175 nM, an improvement over OD(D386) by a factor of nine and an improvement over ODml by a factor of three (Table 1).

Optimization 3: Circular Permutation to Produce "c1" and "c2".

As for the outer domain C-terminus discussed above, the conformation of outer domain N-terminus (loopB and the beta9 strand in Kwong et al Nature 393:648-659 (1998)) appears to be substantially affected by the inner domain in core gp120 and hence the conformation of the N-terminus may be altered significantly when core gp120 is truncated to just the outer domain. The N-terminus of the outer domain may play an important structural role in supporting the epitopes for b12 and other CD4bs-directed antibodies, because it is spatially adjacent both to the beta16 strand that leads out of the "CD4-binding loop" (beta15 strand and alpha3 helix), and to the C-terminal alpha5 helix (which leads out of the outer domain exit loop).

To stabilize the positions and conformation of both the N-terminus (loopB and the beta9 strand) and the C-terminus (alpha5 helix) of the outer domain, Applicants sought to take advantage of their spatial adjacency and develop circularly permuted variants of ODml in which the initial N- and C-termini would be joined by a loop, with new termini created elsewhere in the structure. The basic idea is that the loop joining the initial N- and C-termini will serve as a proxy for the inner domain, and that optimization of the loop sequence and structure for b12-binding will stabilize the conformations of the initial N- and C-termini to favor those of the b12-bound conformation of core gp120.

Applicants focused initially on testing constructs with new termini at two different locations—the V4 loop (the "c1" circular permutant) and the beta16/17 hairpin (the "c2" circular permutant). The V4 loop had missing density in the b12-bound crystal structure and so its conformation was judged non-essential for b12-binding. Furthermore, the V4 is bounded in sequence by two cysteines that are paired in disulfide bonds. Both strands of the beta16/17 hairpin are also bounded by disulfides. Hence in both cases it was thought that native disulfide bonds would assist in fold stabilization for the new permutants. It was recognized that other constructs, such as placing new termini in the V3 loop, might also be promising.

Flexible backbone loop design was carried out with RosettaRemodel to determine candidate loop lengths and compositions for the loop to join the existing termini. In these simulations, the first and last residues of ODml and the residues of the loop insertion were allowed to move backbone conformations and to change to other amino acids. It was concluded that only two additional residues were required to join the existing termini while maintaining the alpha5 helix in the orientation of the b12-bound crystal structure. A linker from computational designs with a loop sequence of "GLSG" in which the two-residue insertion was "LS" (the first "G" replaced the original C-terminal "E" of ODml, and the second "G" replaced the original N-terminal "R" of ODml) was used to build circularly permuted outer domains c1 and c2. c1 and c2 were expressed and purified from mammalian cells, and their binding to b12 assessed by SPR. The $K_D$s for b12 binding for c1 and c2 were 140 nM and 127 nM, respectively, representing in both cases an improvement by a factor of approximately 11 over the OD(D386) and an improvement by a factor of approximately four over the ODml (Table 1).

Based on the computational designs, focused libraries for the N- and C-termini connecting loop were constructed to further optimize the sequence with yeast selection. The libraries were constructed separately for both c1 and c2, and in both cases used the following codons to cover the "GLSGP" residue positions from the computational design: GGC HTW KCY GGT VYY. The libraries were screened on the surface of yeast for b12 Fab binding, and it was found that the sequences for this region did not respond strongly to the selective pressure. After 4 rounds of enrichment, the linker region remained divergent in sequence. From the c1 library Applicants obtained "GLSGP", "GIAGI", "GIAGV", "GIAGA" and "GLSGP" for the region described above. Similarly from the c2 library, "GISGA", "GLSGA", "GLSGV", "GLSGI", "GLAGI" were found. The sequence "GIAGI" was chosen for subsequent constructs based on the consensus from the c1 library and structural analysis; the consensus from the c2 library was very similar to the original computational design. Applicants concluded that the circular permutation had far greater effects on binding than the sequences of the linker.

Optimization 4: Combine Disulf 1 with Circular Permutation and Additional Modifications, to Produce "c1d1", "c2d1" and "c2d2".

Flexible backbone design using RosettaRemodel was employed to place the engineered 285-481 disulfide from ODml(disulf 1) at structurally analogous positions within the circular permutants c1 and c2. This procedure indicated that additional mutations to accomodate the new disulfide were not necessary in the c1 or c2 context. Nonetheless, additional mutations (N478I and W479A in HxB2 numbering) were made to improve the interaction of the alpha5 helix with the core of the outer domain (N478I) and to eliminate a surface-exposed large hydrophobic and optimize helix propensity on alpha5 (W479A). The clones carrying the additional disulfide were called "c1d1" and "c2d1," with analogous mutations (including the new linker, the new disulfide and the N478I and W479A), differing only on circular permutation scheme described above. The 283-477 disulfide ("disulf 2") was also built in the c2 context, and this construct was named "c2d2".

c1d1, c2d1 and c2d2 were expressed and purified from mammalian cells, and binding to b12 was assessed by SPR.

The KDs for b12 were 59 nM for c1d1. and 25 nM for c2d1, and the $K_D$ for b12 binding to c2d2 was 68 nM (Table 1).

To corroborate the SPR data with a purely solution measurement, the binding of mammalian-expressed c1d1 to b12 IgG was assessed by isothermal titration calorimetry (ITC) (Table 1). By ITC, the $K_D$ for the b12-c1d1 interaction was 65 nM, in excellent agreement with the SPR value of 59 nM. Consistent with these findings, a $K_D$ for the c1d1-b12 interaction was measured on the surface of yeast using quantitative titrations of b12 Fab binding to yeast-displayed c1d1, and the $K_D$ in that case was 21 nM.

Thus the combination of either new disulfide (d1 or d2) and either circular permutation (c1 or c2) generated outer domain constructs with higher b12 affinity than either the d1 disulfide or the c1 or c2 circular permutations alone. Overall, according to the SPR data, c1d1_N386D showed a b12-binding improvement over OD(386) by a factor of 28 and an improvement over ODml by a factor of 9; c2d1 showed an improvement over OD(386) by a factor of 64 and an improvement over ODml by a factor of 21 (Table 1).

The $K_D$ for the c1d1-VRC01 interaction was measured by both SPR and ITC (Table 1). The $K_D$ from SPR was determined by kinetics fitting to be 139 nM. This was also in agreement with ITC measurements: the $K_D$ by ITC was 200 nM. These values indicate a modest improvement over ODml(N386) ($K_D$=530 nM) but still a factor of 35 to 50 worse than core gp120 ($K_D$=4 nM).

As a control to test whether the RPAPPPH loop selected in ODml to replace the beta20/21 sequence remained superior to the wild-type beta20/21 sequence in the c1d1 context, a variant of c1d1 with the wild-type beta20/21 was created and its binding to b12 assessed by SPR. This construct was called "c1d1_b2021". The $K_D$ for the b12 interaction with c1d1_b2021 was 148 nM, approximately 2.5 times weaker than c1d1_N386D (Table 1). Hence, the selected trim for the beta20/21 loop region remains superior to the wild-type beta20/21, though it is possible that other loops might perform even better in the c1d1 context. Note: Applicants have termed c1d1_N386D as "eOD N386D" (Table 1).

Optimization 5: Engineer a New Disulfide to Improve VRC01 Binding, Producing "c1d1_b10disulf" and "c2d1_b10disulf".

Applicants hypothesized that the VRC01 affinity could be improved by stabilizing the conformation of loop D which is an important part of the VRC01 epitope according to the crystal structure (PDB ID:3NGB). Applicants employed flexible backbone disulfide design in RosettaRemodel to evaluate potential candidates, and identified a candidate between positions 272 and 348 in H×B2 numbering. Applicants called this the "beta10 disulfide", or "b10disulf" for short, because position 272 is in the middle of the beta10 strand on gp120. This was thought a good candidate to restrict the conformational mobility of loop D because the beta10 strand leads into loop D; also the removal of inner domain exposed the beta10 region.

Variants of c1d1 and c2d1 were assembled with the beta 10 disulfide, and these proteins, "c1d1_b10disulf" and "c2d1_b10disulf", were expressed and purified from mammalian cells. VRC01 binding by c2d1_b10disulf was found to have a $K_D$ of 289 nM by SPR, but VRC01-binding affinity could not be measured by SPR for c1d1_b10disulf owing to un-fittable kinetics. Instead, binding of c1d1_b10disulf to VRC01 was assessed by ITC, and the $K_D$ was 100 nM. This was an improvement by a factor of two over c1d1_N386D ($K_d$ for VRC01-c1d1 measured by ITC was 200 nM), suggesting that the engineered disulfide was effective at stabilizing relevant conformations of loop D. The interactions of both c1d1_b10 disulf and c2d1_b10disulf with b12 were assessed by SPR and the $K_D$s were 200 nM (c1d1_b10disulf) and 148 nM (c2d1_b10disulf). For both molecules, the b12 affinity was reduced by adding the beta 10 disulfide.

The data indicate that the beta 10 disulfide improves VRC01 binding but worsens b12 binding. The c1d1_b10disulf and c2d1_b10disulf constructs might be useful as immunogens, with particular effectiveness to avoid a hypothetical situation in which b12-like antibodies are induced that impede the elicitation of VRC01-like antibodies. These constructs might also be useful as (more specific) probes for VRC01-like antibodies.

Optimization 6: Minimization of Glycosylation Sites to Produce c1d1 minglyc.

Applicants sought a construct with minimal glycans, both to improve the probability of crystallization and also to allow a test of the effect of full vs minimal glycosylation on immune responses to the CD4bs. To identify a minimally glycosylated construct, Applicants employed yeast display library testing and selection. First, Applicants tested gp120 and OD constructs with all glycosylation sites eliminated by mutating N->D at each site; these constructs, called "gp120_no_glycan" and "OD_no_glycan", displayed but did not bind b12 IgG. Applicants had already found that the "gp120_partial_glycan_deletion" construct would display on yeast and bind b12 with high affinity—in this construct, 6 of the 17 glycosylation sites have been eliminated by N->D mutations as noted earlier. Applicants next constructed an analogous "OD_partial_glycan_deletion" that was essentially residues 252-482 from the core gp120 in PDB ID:1RZJ, but with N glycosylation sites on the outer domain eliminated by N->D mutations at 5 positions (276, 339, 392, 463); this construct also displayed on yeast and bound b12 with high affinity. Applicants hypothesized that one or both glycans at positions 262 and 448 were essential for folding due to the unusual peptide topology near the glycans, so Applicants constructed the following c1d1 variants with glycosylation sites mutated by N->D (a) "c1d1_no_glycan", with all glycosylation sites mutated (b) "c1d1_448_262_glycan" with all glycosylation sites except 448 and 262 mutated (c) "c1d1_448_glycan" with all glycosylation sites except 448 mutated (d) "c1d1_262_glycan" with all glycosylation sites except 262 mutated. These four constructs were evaluated for display and b12 Fab binding on the yeast surface, and only "c1d1_448_262_glycan" bound b12 with high affinity. The mutants that carry only one of the two glycans displayed normally, but bound b12 Fab at a much reduced level.

Applicants now refer to the c1d1_448_262 construct simply as "c1d1_minglyc", or "eOD_minglyc". c1d1_minglyc was produced in mammalian cells and its binding to b12 and VRC01 was assessed by SPR Table 1). The $K_D$ for b12 was 31 nM, and the $K_D$ for VRC01 was 7.5 nM. These KDs are both in the range of $K_D$s reported for gp120 interacting with the respective antibodies. Eliminating most glycans improved the b12 affinity by a factor of approximately 2 compared to c1d1_N386D, possibly due to the removal of glycans at 276 and/or 339 which lie just outside the b12 epitope. Taking the c1d1-b12 $K_D$ from ITC (200 nM) as the standard for comparison, the VRC01 affinity of c1d1_minglyc improved by a factor of 27. The VRC01 binding improvement may be due at least in part to removal of the glycans at 276 and/or 463, by analogy to the effect of eliminating N386 on b12 binding.

Optimization 7: From c1d1_b10disulf, use zero-length circular permutation linker and redesign alpha5 helix, to produce "c1d1_v2". To test whether the sequence and design model for the alpha5 helix and loop linker in c1d1_N386D, Applicants used RosettaRemodel to predict the structure of this region, using the known sequence. These efforts failed to converge on a low energy structure, and the resulting models suggested that the two-residue loop linker in c1d1_N386D could be shortened. Indeed, RosettaRemodel designs allowing the alpha5 helix to move relative to the rest of the outer domain indicated that the two-residue linker could be eliminated and the termini joined, with the alpha5 helix positioned to make the d1 disulfide and to support the b12-bound conformation of the 472-475 loop.

To devise a variant of c1d1 with a zero-length linker, Applicants constructed a directed mutagenesis library based on the new designs, and screened it on the surface of yeast for b12 binding. The library (a) enforced a two-residue deletion from the linker (b) allowed variation at four positions linking the original termini—two residues each from the original N- and C-termini (degen codon VBT) and (c) allowed variation on the helix—this variation spanned the c1d1 sequence and newly designed sequences, with the helix (c1d1 sequence GDMRDIARC) represented by the amino acids GDM followed by degenerate codons [SST]-[SRT]-[RKR]-[SYT][SST]. The DNA oligo used to span this region and fully encode the library was: AgTCCgAAATTTTTA-gACCCggCggCggCgATATG—SSTSRTRKRSYTSST—TGC—VBTVBTVBTVBT—GTGTCTACACAGCTTCT-TCTTAATGGCTC. The library was based on c1d1_b10disulf rather than c1d1_N386D, so the library enforced the b10 disulfide.

This library was screened on yeast for b12 Fab binding, and after 5 rounds of sorting at b12 Fab concentrations of 50 nM, 5 nM, 1 nM, 2 nM (increased concentration for greater signal recovery to allow aggressive gating for tight binders), and 500 pM. The library converged to a single clone (called "c1d1_v2") with the new 15-residue sequence GDMAGM-PRCGGGAVS replacing the 17-residue c1d1 sequence GDMRDIARCQIAGTVVS in the linker region.

The $K_d$ for c1d1_v2-b12 binding as measured on yeast by b12 Fab titration was 11 nM, in comparison to 21 nM for the c1d1-b12 $K_D$ measured in the same manner on yeast. Attempts to measure the $K_D$ for c1d1_v2-VRC01 by VRC01 Fab titration on yeast could only establish that the $K_D$ was greater than 50 nM (Table 1).

c1d1_v2 was expressed and purified from mammalian cells and its binding to b12 evaluated by SPR. The $K_D$ for b12 was 30 nM, an improvement by a factor of eight compared to c1d1_b10disulf, and an improvement by a factor of two compared to c1d1_N386D. These results suggested that the zero-length linker and redesigned alpha5 helix in c1d1_v2 were highly effective at improving b12 binding affinity, enough to over compensate for the reduced b12 affinity caused by the b10 disulfide. Efforts are currently underway to construct and test a variant of c1d1 that has the modified linker and alpha5 helix but does not contain the b10 disulfide.

The binding of c1d1_v2 to VRC01 was assessed by both SPR and ITC (Table 1). The $K_D$ for VRC01 was 249 nM by SPR and 100 nM by ITC, indicating that the affinity for VRC01 was not strongly altered compared to c1d1_b10disulf ($K_D$ for VRC01 was 100 nM by ITC).

Binding Specificity Evaluation.

The binding specificity of c1d1_N386D, c1d1_minglyc, c1d1_v2, and core gp120 was assessed with a panel of CD4bs-directed antibodies, the glycan-directed antibody 2g12, and CD4-IgG2. The CD4bs-directed antibodies tested included the broadly neutralizing antibodies b12, VRC01 and VRC03, and the non-neutralizing antibodies b13, m14, m18, F105, and 15e. In this experiment, each antibody (and CD4-IgG2) was captured on the SPR sensor chip, and the various c1d1 and gp120 constructs were flowed as analytes. gp120 was used at a concentration of 100 nM, while the c1d1 constructs were used at a concentration of 1 μM. The results show that the c1d1 constructs bind only to the neutralizing CD4bs antibodies and do not bind to CD4-IgG2, while gp120 binds to CD4 and all antibodies tested.

Yeast Display.

Genes were assembled by overlapping oligos and cloned into the PCTCON2 vector by homologous recombination. Libraries as well as single genes were transformed and using a yeast surface display system previously described (G. Chao et al., Nat Protoc 1, 755 (2006).). Briefly, S. cerevisiae EBY100 competent cells were transformed with 1 μg of pCTCON2 triple-digested vector (BamHI/SalI/NheI, NEB) and a 10× molar excess of insert using electroporation. Typical transformation efficiency ranged from 106 to 107 for a 1× transformation and ≈80% of the recovered sequences from the naïve libraries contained full-length in-frame gene variants. The resulting yeast culture was grown at 30° C., with 250 rpm shaking in 2% glucose C-trp-ura media and passaged at least two times. Once the culture reached a density of $2 \times 10^7 - 3 \times 10^7$ cells/mL it was transferred to 2% galactose C-trpura media and grown for 12-16 hours to induce protein expression on the surface of yeast. 106 to 108 yeast cells were then pelleted and washed with PBSA buffer (0.01 M sodium phosphate, pH 7.4, 0.137 M sodium chloride, 1 g/L bovine serum albumin). Cells were then incubated with b12 IgG pr Fab on an orbital shaker for 1 hour at 4° C. Finally, cells were pelletied, washed two times and fluorescently labeled with phycoerythrin conjugated α-hIgG (Invotrogen) and fluorescein isothiocyanate labeled α-cMyc Ab (Immunology Consultants Laboratory) at 4° C. for 0.5-1 hour.

Cells were analyzed using fluorescence activated cell sorting (BD Influx, BD Biosciences) for selection and titration. For selection, double positive clones were collected, expanded, induced and labeled as before for additional rounds of selection. For titration, identical clones were labeled with serial dilutions of b12 Fab or VRC01 Fab, usually in 3 to 5 fold steps from 100-250 nM antibody-PBSA solutions.

Protein Expression.

Gp120 and outer domain variants were cloned into a pHLsec vector with AgeI and KpnI sites, expressed by secretion from 293F cells in suspension, and purified by Ni++ chromatography and size exclusion chromatography into HBS buffer.

SPR Experiments.

SPR experiments were carried out on a Biacore 2000. Unless otherwise noted, for affinity and kinetics assessments, b12 or VRC01 IgG was captured on the sensor surface by anti-human IgG, and gp120 or outer domain variants were flowed as analyte, using HBS-EP buffer (GE Biosciences).

Sequences.

Note: all protein sequences used for mammalian expression included a histag (GTKHHHHHH) at the C-terminus, but the tags are not listed below.

wild-type core GP120
GARSEVVLVNVTENFNMWKNDMVEQMHEDIISLWDQSLKPCKLTPLCVGA
GSCNTSVITQACPKVSFEPIPIHYCAPAGFAILKCNNKTFNGTGPCTNVS
TVQCTHGIRPVVSTQLLLNGSLAEEEVVIRSVNFTDNAKTIIVQLNTSVE
INCTGAGHCNISRAKWNNTLKQIASKLREQFGNNKTIIFKQSSGGDPEIV
THSFNCGGEFFYCNSTQLFNSTWFNSTWSTEGSNNTEGSDTITLPCRIKQ
IINMWQKVGKAMYAPPISGQIRCSSNITGLLLTRDGGNSNNESEIFRPGG
GDMRDNWRSELYKYKVVKIE GP120_no_glycan
GARSEVVLVDVTENFNMWKNDMVEQMHEDIISLWDQSLKPCVKLTPLCVG
AGSCDTSVITQACPKVSFEPIPIHYCAPAGFAILKCNDKTFDGTGPCTDV
STVQCTHGIRPVVSTQLLLDGSLAEEEVVIRSVDFTDNAKTIIVQLDTSV
EIDCTGAGHCNISRAKWDNTLKQIASKLREQFGNDKTIIFKQSSGGDPEI
VTHSFNCGGEFFYCDSTQLFDSTWFDSTWSTEGSDNTEGSDTITLPCRIK
QIINMWQKVGKAMYAPPISGQIRCSSDITGLLLTRDGGNSNDESEIFRPG
GGDMRDNWRSELYKYKVVKIE GP120_partial_glycan_deletion
GARSEVVLVNVTENFNMWKNDMVEQMHEDIISLWDQSLKPCVKLTPLCVG
AGSCDTSVITQACPKVSFEPIPIHYCAPAGFAILKCNNKTFNGTGPCTNV
STVQCTHGIRPVVSTQLLLNGSLAEEEVVIRSVDFTDNAKTIIVQLNTSV
EINCTGAGHCNISRAKWDNTLKQIASKLREQFGNNKTIIFKQSSGGDPEI
VTHSFNCGGEFFYCDSTQLFDSTWFDSTWSTEGSNNTEGSDTITLPCRIK
QIINMWQKVGKAMYAPPISGQIRCSSNITGLLLTRDGGNSNDESEIFRPG
GGDMRDNWRSELYKYKVVKIE GP120 (N386D)
GARSEVVLVNVTENFNMWKNDMVEQMHEDIISLWDQSLKPCVKLTPLCV
GAGSCNTSVITQACPKVSFEPIPIHYCAPAGFAILKCNNKTFNGTGPCTN
VSTVQCTHGIRPVVSTQLLLNGSLAEEEVVIRSVNFTDNAKTIIVQLNTS
VEINCTGAGHCNISRAKWNNTLKQIASKLREQFGNNKTIIFKQSSGGDPE
IVTHSFNCGGEFFYCDSTQLFNSTWFNSTWSTEGSNNTEGSDTITLPCRI
KQIINMWQKVGKAMYAPPISGQIRCSSNITGLLLTRDGGNSNNESEIFRP
GGGDMRDNWRSELYKYKVVKIE OD_no_glycan
RPVVSTQLLLDGSLAEEEVVIRSVDFTDNAKTIIVQLDTSVEIDCTGAGH
CNISRAKWDNTLKQIASKLREQFGNDKTIIFKQSSGGDPEIVTHSFNCGG
EFFYCDSTQLFDSTWFDSTWSTEGSDNTEGSDTITLPCRIKQIINMWQKV
GKAMYAPPISGQIRCSSDITGLLLTRDGGNSNDESEIFRPGGGDMRDNWR
SE OD_partial_glycan_deletion
RPVVSTQLLLNGSLAEEEVVIRSVDFTDNAKTIIVQLNTSVEINCTGAGH
CNISRAKWDNTLKQIASKLREQFGNNKTIIFKQSSGGDPEIVTHSFNCGG
EFFYCDSTQLFDSTWFDSTWSTEGSNNTEGSDTITLPCRIKQIINMWQKV
GKAMYAPPISGQIRCSSNITGLLLTRDGGNSNDESEIFRPGGGDMRDNWR
SE -continued OD(D386)
RPVVSTQLLLNGSLAEEEVVIRSVNFTDNAKTIIVQLNTSVEINCTGAG
HCNISRAKWNNTLKQIASKLREQFGNNKTIIFKQSSGGDPEIVTHSFNCG
GEFFYCDSTQLFNSTWFNSTWSTEGSNNTEGSDTITLPCRIKQIINMWQK
VGKAMYAPPISGQIRCSSNITGLLLTRDGGNSNNESEIFRPGGGDMRDNW
RSE c1d1_262_glycan
DTITLPCRPAPPPHCSSDITGLILTRDGGNSNDESEIFRPGGGDMRDIAR
CQIAGTVVSTQLLLNGSLAEEEVVIRSVDFTDNAKSICVQLDTSVEIDCT
GAGHCDISRAKWDNTLKQIASKLREQFGNDKTIIFKQSSGGDPEIVTHSF
NCGGEFFYCDSTQLFDSTWFDSTWS c1d1_448_glycan
DTITLPCRPAPPPHCSSNITGLILTRDGGNSNDESEIFRPGGGDMRDIAR
CQIAGTVVSTQLLLDGSLAEEEVVIRSVDFTDNAKSICVQLDTSVEIDCT
GAGHCDISRAKWDNTLKQIASKLREQFGNDKTIIFKQSSGGDPEIVTHSF
NCGGEFFYCDSTQLFDSTWFDSTWS c1d1_no_glycan
DTITLPCRPAPPPHCSSDITGLILTRDGGNSNDESEIFRPGGGDMRDIAR
CQIAGTVVSTQLLLDGSLAEEEVVIRSVDFTDNAKSICVQLDTSVEIDCT
GAGHCDISRAKWDNTLKQIASKLREQFGNDKTIIFKQSSGGDPEIVTHSF
NCGGEFFYCDSTQLFDSTWFDSTWS ODml(D386)
RPVVSTQLLLNGSLAEEEVVIRSVNFTDNAKTIIVQLNTSVEINCTGAGA
GHCNISRAKWNNTLKQIASKLREQFGNNKTIIFKQSSGGDPEIVTHSFNC
GGEFFYCDSTQLFNSTWFNSTWSTEGSNNTEGSDTITLPCRPAPPPHCSS
NITGLLLTRDGGNSNNESEIFRPGGGDMRDNWRSE ODml(N386)
RPVVSTQLLLNGSLAEEEVVIRSVNFTDNAKTIIVQLNTSVEINCTGAGH
CNISRAKWNNTLKQIASKLREQFGNNKTIIFKQSSGGDPEIVTHSFNCGG
EFFYCNSTQLFNSTWFNSTWSTEGSNNTEGSDTITLPCRPAPPPHCSSNI
TGLLLTRDGGNSNNESEIFRPGGGDMRDNWRSE c1
DTITLPCRPAPPPHCSSNITGLLLTRDGGNSNNESEIFRPGGGDMRDNWR
SGLSGPVVSTQLLLNGSLAEEEVVIRSVNFTDNAKTIIVQLNTSVEINCT
GAGHCNISRAKWNNTLKQIASKLREQFGNNKTIIFKQSSGGDPEIVTHSF
NCGGEFFYCDSTQLFNSTWFNSTWS c2
GEFFYCDSTQLFNSTWFNSTWSTEGSNNTEGSDTITLPCRPAPPPHCSSN
ITGLLLTRDGGNSNNESEIFRPGGGDMRDNWRSGLSGPVVSTQLLLNGSL
AEEEVVIRSVNFTDNAKTIIVQLNTSVEINCTGAGHCNISRAKWNNTLKQ
IASKLREQFGNNKTIIFKQSSGGDPEIVTHSFNCG c1d1_N386D (also called “eOD_N386D”)
DTITLPCRPAPPPHCSSNITGLILTRDGGNSNNESEIFRPGGGDMRDIAR
CQIAGTVVSTQLLLNGSLAEEEVVIRSVNFTDNAKSICVQLNTSVEINCT

```
GAGHCNISRAKWNNTLKQIASKLREQFGNNKTIIFKQSSGGDPEIVTHSF

NCGGEFFYCDSTQLFNSTWFNSTWS c1d1_b10disulf
DTITLPCRPAPPPHCSSNITGLILTRDGGNSNNESEIFRPGGGDMRDIAR

CQIAGTVVSTQLLLNGSLAEEEVVCRSVNFTDNAKSICVQLNTSVEINCT

GAGHCNISRAKWNNTLKQIASCLREQFGNNKTIIFKQSSGGDPEIVTHSF

NCGGEFFYCDSTQLFNSTWFNSTWS c1d1_v2
DTITLPCRPAPPPHCSSNITGLILTRDGGNSNNESEIFRPGGGDMAGMPR

CGGGAVSTQLLLNGSLAEEEVVCRSVNFTDNAKSICVQLNTSVEINCTGA

GHCNISRAKWNNTLKQIASCLREQFGNNKTIIFKQSSGGDPEIVTHSFNC

GGEFFYCDSTQLFNSTWF c1d1_minglyc (also called "eOD_minglyc" and
"c1d1_448_262_glycan")
DTITLPCRPAPPPHCSSNITGLILTRDGGNSNDESEIFRPGGGDMRDIAR

CQIAGTVVSTQLLLNGSLAEEEVVIRSVDFTDNAKSICVQLDTSVEIDCT

GAGHCDISRAKWDNTLKQIASKLREQFGNDKTIIFQSSGGDPEIVTHSFN

CGGEFFYCDSTQLFDSTWFDSTWS c1d1_b2021
DTITLPCRIKQIINMWQKVGKAMYAPPISGQIRCSSNITGLILTRDGGNS

NNESEIFRPGGGDMRDIARCQIAGTVVSTQLLLNGSLAEEEVVIRSVNFT

DNAKSICVQLNTSVEINCTGAGHCNISRAKWNNTLKQIASKLREQFGNNK

TIIFKQSSGGDPEIVTHSFNCGGEFFYCDSTQLFNSTWFNSTWS c2d1
GEFFYCDSTQLFNSTWFNSTWSTEGSNNTEGSDTITLPCRPAPPPHCSSN

ITGLILTRDGGNSNNESEIFRPGGGDMRDIARCQIAGTVVSTQLLLNGSL

AEEEVVIRSVNFTDNAKSICVQLNTSVEINCTGAGHCNISRAKWNNTLKQ

IASKLREQFGNNKTIIFKQSSGGDPEIVTHSFNCG c2d2
GEFFYCDSTQLFNSTWFNSTWSTEGSNNTEGSDTITLPCRPAPPPHCSSN

ITGLILTRDGGNSNNESEIFRPGGGDMRCGARSGIAGTVVSTQLLLNGSL

AEEEVVIRSVNFTDNAKCIIVQLNTSVEINCTGAGHCNISRAKWNNTLKQ

IASKLREQFGNNKTIIFKQSSGGDPEIVTHSFNCG c2d1_b10disulf
GEFFYCDSTQLFNSTWFNSTWSTEGSNNTEGSDTITLPCRPAPPPHCSSN

ITGLILTRDGGNSNNESEIFRPGGGDMRDIARCQIAGTVVSTQLLLNGSL

AEEEVVCRSVNFTDNAKSICVQLNTSVEINCTGAGHCNISRAKWNNTLKQ

IASCLREQFGNNKTIIFKQSSGGDPEIVTHSFNCG
```

In a first aspect, the present invention provides polypeptides comprising or consisting of an amino acid sequence according to the formula:

```
(Z1)(R/-)(P/T/G)(V/A)VSTQLLL(N/D)GSLAEEEVV(I/C)RS

V(N/D)FTDNAK(T/S/C)I(I/C)VQL(N/D)TSVEI(N/D)CTGAGH

C(N/D)ISRAKW(N/D)NTLKQIAS(K/C)LREQFG(N/D)(N/D)KTI

IFKQSSGGDPEIVTHSFNCG(Z3)
```

Wherein Z1 is absent, or is Z1a or Z1b, wherein

```
Z1a is GEFFYCDSTQLFNSTWFNSTWSTEGSNNTEGSDTITLPCR (X3)CSSNITGL(L/I)LTRDGGNSNNESEIFRPGGGDMR(D/C)(Z5)

(Z/10);
and

Z1b is DTITLPCR(X3)CSS(N/D)ITGL(L/I)LTRDGG(N/D)S (N/D)(N/D)ESEIFRPGGGDM(R/-)(D/-)(Z5)(Z10)
``` wherein Z5 is any four amino acids (including but not limited to NWRS, IARC, AGMP, and GARS)

wherein Z10 is any four amino acids (including but not limited to GLSG, QIAG, RCGG, and GIAG)

wherein Z3 is absent, is Z3a or Z3b, wherein

```
Z3a is GEFFYCDSTQLFNSTWFNSTW(X2)DTITLPCR(X3)CSSNI

TGLLLTRDGGNSNNESEIFRPGGGDM(R/-)(D/-)(Z5)(E/-);
and

Z3b is GEFFYCDSTQLF(N/D)STWF(N/D/-)(S/-)(T/-)(W/
-)(S/-)
``` wherein X2 is absent, or is STEGSNNTEGS wherein X3 is IKQIINMWQKVGKAMYAPPISGQIR, or any 6-8 amino acids (including but not limited to PAPPPH, KGGRPG, and IPKRDFN);

with the proviso that if Z1a is present, Z3 is absent, and if Z1b is present, Z3 is Z3b; and if Z1 is absent, Z3 is Z3a.

In one embodiment of the polypeptide genus disclosed above, the asparagine residues (N) may be modified to any other suitable amino acid residues to reduce the number of glycolyation sites on the polypeptide as desired. In one non-limiting embodiment, one or more asparagine residues are modified to aspartic acid (D) residues.

In the initial development of the eOD, the heavily glycosylated eOD_N386D, lacking only the glycan at 386, had only modest affinity for mature VRC01, with a Kd of 80 nM. This modest affinity was more than a factor of 10 weaker than the affinity of core gp120 for mature VRC01 (Kd=4 nM). This indicated a flaw in the structure of c1d1. However, the minimally glycosylated c1d1 ("c1d1_mingly", with only 2 N-linked glycosylation sites intact) had a considerably higher affinity of 7.5 nM. That indicated that one route to improving mature VRC01 affinity was to remove glycans. However, for immunization purposes it is generally preferable to retain as many native glycans as possible, to avoid exposing protein epitopes on the immunogen that are not exposed on the virus and to maintain steric constraints imposed by glycans on antibody angle of approach.

Here, Applicants report that Applicants' screen of a yeast display library to identify high affinity constructs with glycans removed converged on a variant with glycans removed at two positions (276 and 463 in HxB2 numbering). This construct, named "eOD_N276D_N463D" or "eOD_VD(−)" when produced from 293 cells has a Kd of 4 nM for mature VRC01. Further, Applicants produced a variant with only the glycan at 276 removed, called "eOD_N276D" or "eOD_D(−)" and that variant has a Kd of 27.8 nM for mature VRC01. These two constructs are highly valuable for vaccine applications because they rescue high affinity VRC01 binding while retaining as many glycans as possible. Applicants subsequently found that these two constructs also have measurable affinity for germline VRC01, further highlighting their utility as vaccine candidates. eOD_N276D_N463D binds to germline VRC01 with a Kd of 380 mcM and eOD_N276D binds to germline VRC01 with a Kd of 640 mcM.

The present invention also encompasses further screens of a yeast display library, or any other comparable library, to identify high affinity constructs with either glycan deletions and/or mutations. Preparation of eOD deletions and/or mutations as well as the screening of a library are exemplified herein. In particular, the present invention especially relates to eOD mutants with either a deletion and/or a mutation at any one of positions 276, 277 or 278 or a combination thereof. In an advantageous embodiment, the mutations include, but are not limited to, (a) N mutated to any amino acid except N at 276 or (b) any amino acid mutated to P at 277 or (c) mutation of S or T at 278 to any amino acid other than S or T or any combination thereof.

The fact that removal of the glycan at 276 allows measureable binding by germline VRC01 indicates that this mutation may be essential for germline-targeting immunogens. It also indicates that the HIV strains that infected the patients that subsequently produced VRC01-like antibodies may have contained a mutation that removes the glycan at 276. Indeed, Applicants suspect this to be the case. Applicants have analyzed 2867 different HIV Env sequences from the LANL database and found that 145 of those sequences lack a glycosylation site at position 276. Applicants also analyzed 190 HIV env sequences from the virus panel published in Wu et al Science 2010 and found that 11 of those sequences lack a glycosylation site at position 276. Thus, approximately 5% of HIV Env sequences lack a glycan at 276. To Applicants' knowledge this has never been presented or appreciated previously. From the 157 sequences Applicants found that lack a glycan at 276, there are 52 unique and fully defined sequons at 276 (combinations of amino acids at 276, 277, 278). Applicants claim all of those sequons at 276, and any other mutation that obeys: (a) N mutated to any amino acid except N at 276 or (b) any amino acid imitated to P at 277 or (c) mutation of S or T at 278 to any amino acid other than S or T.

Analysis of the crystal structure of PGV04 bound to c1d1_mingly revealed other mutations that could improve binding of mature VRC01-like antibodies, perhaps without the need to remove glycosylation sites. Here Applicants disclose eOD sequences with three such mutations: eOD_I478N, eOD_S387T, and eOD_V270I. The I478N mutation puts back an asparagine that is native to HIV at that position; this N participates in a buried hydrogen bond network and may be important for maintaining native structure. The S387T mutation is designed as a space-filling mutation that may stabilize the structure, and is promising because T is present in this position in 91% of 2868 HIV sequences, while S is present in only 8%. The V270I mutation is also a space-filling mutation that mutates to a more commonly-used residue in HIV Env sequences (V270 occurs in 36% of HIV sequences, while I270 occurs in 62%).

In particular, the present invention especially relates to eOD mutants with either a deletion and/or a mutation at any one of positions 270, 387 or 478 or a combination thereof. In an advantageous embodiment, the mutations include, but are not limited to, eOD_I478N, eOD_S387T, and eOD_V270I or any combination thereof.

In the development of germline-targeting eODs described below, two additional modifications were identified for improving the binding of mature VRC01. One is the mutation L260F, that Applicants have now confirmed to improve mature VRC01 binding. A fully glycosylated variant of eOD with the L260F mutation added "eOD_L260F" has a Kd of 14.3 nM for mature VRC01. This was a surprisingly large benefit to VRC01 binding, because this position is buried in the protein core and does not interact with VRC01 directly. Applicants conclude that this mutation L260F stabilizes an eOD conformation that is superior for VRC01 binding. This mutation may be useful not only in the context of eOD, it could be employed in the context of any HIV Env sequence for the purpose of stabilizing appropriate conformation. This is a novel mutation that does not occur in 2868 different HIV Env sequences from the LANL database. The second modification is a one residue deletion at position 356 in the HxB2 sequence. While the original eOD based on HxB2 had an asparagine at position 356, all of the germline-mature affinity gradient eODs described below contain this deletion and all bind with very high affinity to mature VRC01.Most (84%) of HIV sequences have a deletion at position 355 or 356 relative to the HxB2 strain. So the deletion at 356 may be important for mature VRC01 binding and structural stability of eOD.

In particular, the present invention especially relates to eOD mutants with either a deletion and/or a mutation at any one of positions 260 or 356 or a combination thereof. In an advantageous embodiment, the mutations include, but are not limited to, L260F or a deletion at position 356 or any combination thereof.

Given that either removal of the glycan at 276 or introduction of the mutation L260F caused improvements in VRC01 binding, Applicants tested the effect of combining these two mutations. The resulting construct (eOD_L260F_N276D) had only a slightly improved affinity for mature VRC01 (Kd=11.9 nM) compared to the single mutant eOD_L260F (Kd=14.3 nM), but did have significant higher affinity compared to the single mutant eOD_N276D (Kd=27.8 nM). Furthermore, the double mutant (eOD_L260F_N276D) had a substantially improved affinity for germline VRC01 (Kd(GLVRC01)=149 mcM) compared to eOD_L260F (Kd(GLVRC01)>500 mcM) or eOD_N276D (Kd(GLVRC01)=640 mcM). Hence this double mutant is an important discovery.

In particular, the present invention especially relates to eOD mutants with either a deletion and/or a mutation at any one of positions 260 or 276 or a combination thereof. In an advantageous embodiment, the mutations include, but are not limited to, eOD_L260F_N276D.

Space-filling mutations T257S+S375W were previously employed in the context of core gp120 to stabilize the cd4-bound conformation. Here, Applicants tested the effect of adding those two mutations to the eOD. Applicants found, however, that eOD_T257S_S375W had a Kd for VRC01 that was only 90 nM. Thus introduction of these two space-filling mutations alone into eOD caused no significant improvement in VRC01 binding compared to eOD_N386D (Kd=80 nM). However, surprisingly, when Applicants combined the L260F mutation with the T257S+S357W mutations, Applicants found a significant improvement in VRC01 binding. The triple mutant eOD_T257S_L260F_S375W has a Kd for mature VRC01 of 8.6 nM, a significant improvement over either eOD_T257S_S375W or eOD_L260F.

In particular, the present invention especially relates to eOD mutants with either a deletion and/or a mutation at any one of positions 257, 260 or 375 or a combination thereof. In an advantageous embodiment., the mutations include, but are not limited to, eOD_T257S_S375W and eOD_T257S_L260F_S375W.

Development of Germline-Mature Affinity Gradient Immunogens.

The emerging field of vaccine reverse engineering begins with neutralizing antibodies isolated from natural infection, and attempts to design vaccines that will "re-elicit" antibodies with similar specificities and protective functions. Structural vaccinology, another emerging field that partially overlaps with vaccine reverse engineering, attempts to create immunogens that are optimal faithful structural mimics of pathogen epitopes.

Here, Applicants have gone beyond the boundaries of those disciplines. Applicants have engineered novel vaccine antigens that directly target the germline precursors of known HIV broadly-neutralizing antibodies as well as targeting mature forms of the same antibodies. Using computational design and cell surface display in vitro screening, Applicants rationally engineered Applicants' immunogens to have modest affinity for the predicted germline precursors and to have higher affinity for the mature antibodies. Applicants hope that by engineering an "affinity gradient" between the germline and mature antibody into Applicants' immunogen, Applicants may help to direct the path of somatic mutation towards the desirable mature antibody. Applicants hope that these germline-mature gradient immunogens may be used to activate appropriate germline B cells and guide somatic mutation and clonal expansion toward the development of VRC01-like Abs.

The approach here is a novel extension of vaccine reverse engineering—while Applicants are still pursuing the goal of "re-elicitation" of antibodies isolated from natural infection, Applicants are taking this concept further than has been done before by targeting specific antibody germline genes, considering antibody repertoires and possible somatic hypermutation pathways, and considering the dynamics of SHM. The approach here also departs from traditional structural vaccinology, because Applicants are explicitly making mutations in the target epitope, hence Applicants are violating the usual goal of precise structural mimicry. Applicants' approach offers a unique solution to re-elicitation of Abs, is new type of engineered vaccine component, and has not previously been demonstrated in the literature.

Germline Prediction and Homology Modeling.

The naïve heavy and light chain precursors of VRC01 and PGV04 were calculated using JOINSOLVER® to select the closest variable, diversity and joining genes. Initially, the mature heavy and light CDR3 sequences were used in the junctional regions where it was not possible to track back the actual germline.

There were no available structures of the naïve antibodies, so homology modeling was used to generate starting structures for design. The coordinates of the mature VRC01 FV were extracted from the co-crystal structure bound to GP120 (PDBID:3NGB). The two amino acid deletion in the CDR-L1 was modeled transferring the CDR-L1 from a minimally mutated LC from the same VL gene [PDBID:1GC1 when making model for GP120, later PDBID:3F12 when modeling for the eOD] using RosettaRemodel. The constant region of the Fab was removed to reduce computational time. After correcting the length change, the germline sequence was threaded onto the coordinates using RosettaFixBB design and the resulting germline model was relaxed using RosettaRelax.

Predicted germline precursor antibodies were produced as scFV, Fab and IgG. Binding for VRC01 and PGV04 germline antibodies was measured for YU2, Bal [quasispecies unknown], JRFL, JRCSF and DU179 GP120. BaL was the only construct that showed detectable binding to the germline of VRC01, though it did not show binding to the germline of PGV04. Applicants displayed the BaL core GP120 [based on the sequence http://www.ncbi.nlm.nih.gov/protein/AFJ93245.1] and a D368R knockout variant on the surface of yeast to confirm specificity for the VRC01 germline antibody, but Applicants were unable to detect binding to either germline antibody on the surface of yeast. Applicants were unsure if the inconsistency was an initial false positive hit (possibly from an unfolded protein non-specifically sticking to the VRC01 germline) or if the GP120 behaved differently on the surface of yeast (possibly due to yeast glycans), but Applicants decided to use the BaL sequence as one of Applicants' starting structures nonetheless.

Computational Affinity Maturation.

The homology model of the VRC01 germline FV was aligned back onto the coordinates for the mature VRC01/GP120 complex (PDBID:3NGB) using a backbone alignment to the mature antibody. It was immediately apparent that there was a clash between the newly modeled CDRL1 insert and the glycan attached to N276, so the glycan was removed by N276D mutation. After removing the glycan clash, the redocked complex was minimized to help reduce any side chain clashes.

Computational affinity design was done using RosettaScripts to call sequential modeling tasks in the Rosetta software suite. Initially, small variations in the rigid-body orientation were generated using RosettaDock followed by RosettaBackrub to sample slight conformations in the protein backbone. The initial modeling was done centroid mode with the intention of creating diversity in the starting structure since the computational interface design was being done with a docked homology model rather than a high-resolution structure; therefore, Applicants' confidence was lower for Applicants' input structure.

Following the initial perturbation of the modeled complex, sequence design was performed using RosettaDesign with full atom representation. All sidechains within 8 Å of the interface on both partners were allowed to sample alternative rotameric conformations, and interface mutations were sampled on the side of GP120 to optimize free energy of the structure. To create a large amount of diversity in Applicants' models, five rounds interface optimization were carried out. Because small modifications in backbone position may cause significant bias in side-chain design, a backbone conformational variant was generated prior to each design step, by passing the pose through RosettaBackrub followed by RosettaDesign. After the pose was passed through 5 iterations of backrub followed by design, a final output structure was generated.

This entire procedure was repeated ~100,000 times with each run producing a unique model. Output decoys were filtered based on Rosetta calculated binding energy, then loosely filtered on total score, unsatisfied polar residues and RMSD from the starting structure. The top ~100 decoys were aligned and the predicted mutations were manually inspected. Applicants specifically selected mutations that made backbone contacts with the antibody or targeted sidechains that were identical between both the germline and the affinity-matured antibody. Mutations that passed a manual inspection were used to create directed libraries of GP120 mutants predicted to have increased affinity for the germline of VRC01.

Surface Display and Selection.

The positions on GP120 identified by Rosetta to improve germline antibody binding to GP120 were screened experimentally using yeast surface display and fluorescence-activated cell sorting (FACS). Directed libraries were constructed using PCR assembly with partially degenerate oligonucleotides encoding core Bal [based on http://www.ncbi.nlm.nih.gov/protein/AFJ93245.1] identified in Applicants' initial hit or core 93TH057 GP120 from the crystal structure (PDBID:3NGB). Mutations that were predicted to be beneficial for germline binding as well as the wild type amino acid were libraried using degenerate codons at that position such that all possible combinations of predicted amino acids would be sampled. The PCR assembly product was gel purified and cloned into pCTCON2 via homologous recombination in yeast. The GP120 variants were expressed on the surface of EBY100 as a fusion protein between Aga2p and a C-Myc tag. The germline VRC01 antibody was expressed recombinantly as molecular Fab in E. coli with a C-terminal avitag on the heavy chain. The avitag was enzymatically biotinylated and biotinylated germline VRC01 Fab was pre-incubated with phycoerythrin-conjugated streptavidin (SAPE) to create tetrameric complexes to maximize avidity, as the interaction was expected to be very low affinity. The yeast library was induced overnight and cells were duel-labeled with FITC conjugated anti-C-Myc antibody to measure display and the germline Fab-SAPE complex for binding. The library was sorted to enrich for clones that displayed binding to the germline antibody. Sequences from binding clones were recovered; the resulting GP120 [core_gp120_VH1-2_v2.0] was produced in 293F cells and bound germline VRC01 1.6 uM by SPR.

As Applicants learned more about the mutations that were necessary for germline binding, specifically the importance of removing the glycan at position 276, Applicants suspected that the BaL GP120 that produced the initial positive signal was lacking the N-linked glycan at position 276, either by deletion of the glycan site or from being produced in a cell line that underutilized that position. Applicants have subsequently identified a quasispecies of BaL [http://www.ncbi.nlm.nih.gov/protein/AAR05834.1] that lacks the glycan at position 276 due to a T278A mutation. That protein was produced in 293F cells as both full length and core GP120 and shows detectable binding to the germline of VRC01 and PGV19 IgG in SPR.

Affinity Maturation/eOD Development.

After developing germline binding on the surface of yeast to Bal GP120, Applicants observed that one of the mutations that enriched for B20/21 by 6 amino acids that occurred through an error during library assembly. Seeing that, Applicants sought to immediately transfer these germline binding properties onto Applicants' engineered outer domain (eOD) that was currently in development. The eOD platform offered many advantages over core GP120. While Applicants believe an immunogen with affinity for germline antibodies may be required to induce VRC01-like antibodies, Applicants believe there are other problems with immuno-focusing to the VRC01 epitope using gp120-based immunogens. The variable loops, the inner domain, and the bridging sheet all contain a large number of highly immunogenic and potentially distracting epitopes, and the CD4bs itself appears to be immunogenic for narrowly- or non-neutralizing CD4bs antibodies such as b6, b13, or F105. To combat all of these problems, Applicants have developed the engineered outer domain (eOD). The eOD is only 175 aa long, and lacks the inner domain, variable loops, and bridging sheet, so it cannot induce antibodies against those structures. By virtue of trimming and conformational stabilization, the eOD does not bind known narrowly-neutralizing CD4bs antibodies such as b6, b13, F105, m14, m18, 1.5E, so eOD should not be capable of inducing those well-known, undesired CD4bs antibodies while the final eOD bind to mature VRC01 with affinity comparable to WT GP120. Further, Applicants have a crystal structure of a minimally glycosylated eOD bound to PGV04 (solved by J P Julien and Ian Wilson); this structure superimposes well with the published crystal structure of core gp120 bound to PGV04 (PDB:3SE9), so in the process of trimming and remodeling, Applicants did maintain the appropriate structure. Finally, owing to the small size of the eOD and to the fact that Applicants have changed the location of the N and C termini, Applicants have been able to develop highly multimeric forms of eOD that present the VRC01 epitope facing outward and these should enhance immune responses to the VRC01 epitope. All of these properties make eOD a more desirable immunogen than core GP120.

Using eOD instead of core gp120, Rosetta-directed libraries were combined with interface mutations from core Bal and sorted as described above on the surface of yeast for germline VRC01 binding. Clones that showed binding were sequenced and the protein (eOD_VH1-2_v1.0) from several of the sequences that converged was produced in 293F cells and tested by SPR. The Kd for germline VRC01 binding to eOD_VH1-2_v1.0 was 40 uM. Mutations from that clone were modeled and computational affinity maturation was carried out a second time, with a starting structure containing the previously identified mutations. Four additional rounds of yeast display selection were done. The first two rounds used an expanded set of Rosetta predicted mutations to more aggressively focus on specific parts of the interface. The second two rounds were carried out on a library containing error prone PCR-generated random mutations on the DNA recovered from clones selected in the first two rounds. The resulting eOD (eOD_VH1-2_v4.0 had ~100 nM affinity for the germline of VRC01. However, during the course of development, other VH1-2 antibodies were isolated from HIV positive patients and reported in the literature. NIH45-46 was one such VH1-2 antibody. Applicants produced the germline of NIH45-46, a somatic variant of VRC01. While the paratope was virtually identical to that of VRC01, Applicants were surprised to find that v4.0 variants had no detectable affinity for germline NIH4546. To improve this, a library was generated where the original side chain as well as anything that had previously enriched in Applicants' sorts was sampled. The resulting library was divided in two and each was screened against GL VRC01 or GL NIH45-46. After two sorts, each library was split in half again, and one half was sorted against the opposite antibody while the other half was further sorted on the original antibody. 50 clones from each of the 4 libraries were sequenced. Applicants found that some of the mutations that enriched for one of the germline antibodies were not tolerated by the other antibody. From this data, only mutations that were found in all 4 libraries were selected and used to create eODs to bind to both antibodies. eOD_VH1-2_v5.0 was synthesized and produced in 293F cells. By SPR, eOD_VH1-2_v5.0 bound tightly to both VRC01 germline and NIH4546 germline antibodies.

The final variant of the germline eOD was generated by creating a larger library with all mutations that had previously been observed to enrich, and that library was divided into 7 libraries and sorted for binding to the germline antibodies of VRC01, NIH45-46, PGV19, CHA31, PGV04 as well as mature VRC01 and PGV04 antibodies to ensure tight binding to mature antibodies. 50 clones from the VRC01GL, NIH4546GL, PGV19GL, VRC01Mat and PGV04Mat libraries were sequenced. Common mutations that enriched in all libraries were selected and combined to create eOD_VH1-2_v6.0. This molecule, eOD_VH1-

2_v6.0, binds multiple VH1-2 antibodies, with the following dissociation constants: VRC01GL (44 nM), NIH4546GL (408 nM), PGV19GL (19 nM), VRC01Mat (1.7 nM), NIH4546Mat (3.8 nM) and PGV19Mat (88 nM). Applicants were unsuccessful at developing binders for PGV04GL or CHA31GL on yeast surface display, however they appear to bind weakly in SPR.

In addition to optimizing for germline antibodies, Applicants deliberately selected mutations that did not disrupt tight mature antibody binding. For example, mutations from eOD_VH1-2_v5.0 were reverted back in eOD_VH1-2_v6.0 because they were detrimental to mature binging. Applicants refer to this as Applicants' "affinity gradient", where Applicants deliberately maintain tight mature binding to help bias the direction of somatic hypermutation to select for mutations similar to the mature antibody.

It was recognized early in the development of Applicants' germline immunogen that Applicants would need to find a model organism to immunize in order to show proof of principle. After an extensive search through the genomes of commonly used model organisms for VH genes similar to VH1-2*02, Applicants concluded that rhesus macaque was one of the only available options. Several rhesus macaque VH genes similar to the human VH1-2*-2 were identified [GenBank AAO43416.1 (termed rhesus1, ABD98406.1 (rhesus2), AER46755.1 (rhesus3) and AER46679.1 (rhesus4)]. Rhesus-human chimeric VH1-2 germline antibodies were created from the human germline VRC01 antibody by replacing the human VH with one of the above rhesus VH genes but retaining the rest of the human germline heavy and light chains; Applicants note that Applicants' human germline VRC01 antibody uses the mature VRC01 HCDR3, so the Rhesus-human chimeras do too. The four rhesus-human antibodies are termed rhe-hu1, rhe-hu2, rhe-hu3, and rhe-hu4. Rhe-hu2 and rhe-hu3 differed by only one point mutation at a position considered irrelevant for binding, so they were treated as one antibody called rhe-hu2/3 Applicants found there was no detectable affinity between the rhe-hu antibodies and eOD_VH1-2_v5.0 by SPR.

To resolve the lack of binding to the rhe-hu antibodies, Applicants applied computational affinity maturation and yeast display screening as above. First, a model of the eOD_VH1-2_v5.0 in complex with the human VRC01 germline antibody (huGLVRC01) was created by threading the sequence of eOD_VH1-2_v5.0 onto the original starting structure. A docking protocol was used to "redock" the two partners together and the redocked structure was then relaxed. From this model of eOD_VH1-2_v5.0/huVRC01GL, models for eOD_VH1-2_v5.0 bound to each of the rhe-hu antibodies were created by threading the mutations for the rhesus VH genes onto the model. The computational affinity maturation protocol was run on each of those structures. Here there were a limited number of positions that were targeted for mutagenesis, so the computationally predicted mutations from all 3 modeling runs (rhe-hu1, rhe-hu2/3, and rhe-hu4) were combined into 1 large library. The library was transformed into yeast, split into three sub-libraries, and each sub-library was sorted against one of the three antibodies. Sorting recovered no binders to rhe-hu1. The libraries of rhe-hu2/3 and rhe-hu4 both showed binding on the surface of yeast. After several rounds of sorting, all clones in the libraries sorted against rhe-hu2/3 and rhe-hu4 showed positive binding signal. At that point, both sub-libraries were split into 3 sub-sub libraries. Each sub-sub library was sorted against rhe-hu2/3, rhe-hu4 and human VRC01GL antibodies. 50 colonies were sequenced from each of the 6 sub-sub libraries, and eOD_RheVH1-2_v1.0 and eOD_RheVH1-2_v2.0 were created based on mutations that enriched in all 6 sub-sub libraries, eOD_RheVH1-2_v2.1 was later created based on the eOD_VH1-2_v6.0 human binder. eOD_RheVH1-2_v2.1 is only optimized to bind to rhe-hu2/3 and the human VRC01GL, as analysis of deep sequencing data of VH genes from four naïve rhesus macaques indicated that the rhesus4 VH gene is produced at a lower frequency compared to rhesus2/3, and significantly more mutations were necessary to enable binding to rhe-hu4.

Applicants have further modified the eOD_VH1-2_v6.0 to bind to another class of antibodies derived from the VH1-8 germline gene. This was done using yeast display following the same methods are described herein. The modified sequence is eOD_VH1-2_VH1-8_v.1.0.

Glycan Masking of eOD.

To focus immune responses to the VRC01 epitope, Applicants sought to add glycosylation sites to exposed eOD surfaces outside the VRC01 epitope. The goal was to introduce glycosylation sites that would not only cover up undesired epitopes ("patch-focusing") but also restrict the angle of approach for antibodies targeting the VRC01 epitope ("angle focusing").

Structure-based rational design was employed to select 8 candidate sites, and mutations were designed to introduce N-linked glycosylation sites at these 8 positions. The glycan mutants were designed on the background of eOD_VD(-) and so are named eOD_VD(-)_g1, eOD_VD(-)_g2, eOD_VD(-)_g3, eOD_VD(-)_g4, eOD_VD(-)_g5, eOD_VD(-)_g6, eOD_VD(-)_g7, and eOD_VD(-)_g8. The mutations to introduce the glycans were as follows, given in eOD/HxB2 numbering: eOD_VD(-)_g1 (R76N+V78T/R273N+V275T), eOD_VD(-)_g2 (R50N+Q52S/R480N+E482S), eOD_VD(-)_g3 (I53N+G55S/positions not exist in wt gp120), eOD_VD(-)_g4 (T56N+V58T/positions not exist in wt gp120), eOD_VD(-)_g5 (Q126N+G128S/Q352N+G354S), eOD_VD(-)_g6 (R8N+A10S/R419N+other position not exist in wt gp120), eOD_VD(-)_g7 (P9N+P11T/positions not exist in wt gp120), eOD_VD(-)_g8 (G154N+F156T/G380N and F382T).

The present invention also encompasses introducing one or more additional N-linked glycosylation sites at other locations than those listed above. The mutations may be structure-based or random. Making and testing these mutations are within the purview of the skilled artisan based upon the teachings provided herein.

Applicants attempted to produce each of these mutants in 293S cells and evaluate mature b12 and mature VRC01 binding. The g1 variant did not express, but all the others could be purified from 293 cell supernatants. The Kd values for g2-g8 are given in Table 2.

TABLE 2

Kd values for g2-g8

| Glyc mut | Kd_mVRC01 (nM) | Kd_b12 (nM) |
|---|---|---|
| 2 g | 7.0 | 96 |
| 3 g | 4.7 | 21.6 |
| 4 g | 7.3 | 76 |
| 5 g | 15 | 132 |
| 6 g | 4.6 | 514 |
| 7 g | 109 | 421 |
| 8 g | 2.8 | 7 |

The Kd values illustrate that the glycan masking was successful in all cases except for g7, in that Applicants could add glycans to non-VRC01 epitope positions and retain high affinity binding by VRC01. Reduction of b12 affinity, which was achieved in most cases, is considered desirable because b12 will compete with VRC01 but Applicants do not want to induce b12-like antibodies in place of VRC01-like antibodies because b12 is less potent and less broadly-neutralizing. Applicants expect that combinations of the successful mutations will also be successful and will provide more complete glycan masking, so Applicants are testing those now. Applicants also expect that these mutations and their combinations may be transferred to any eOD variant and are not restricted to the VD(−) variant on which they were originally tested. Finally, Applicants note that these glycan masking mutations are highly novel and specific for the eOD because all but one (g6) are particular for eOD and are incompatible with the structure of gp120, gp140 or gp160.

The present invention also encompasses combinations of glycan masking. In one embodiment, the combination may be g3+g8 and/or g2+g8, although any combination of glycan mutants g2-g8 are envisioned for the present invention.

eOD Multimers.

To enhance immunogenicity of the VRC01 epitope, Applicants sought to devise multimeric forms of eOD. These should provide the ability to stimulate B cells using multivalent avidity, and in addition the larger particulate forms should mimic a virus-like symmetric presentation of epitopes, reduce immune responses to regions buried in the multimer, and enhance in vivo trafficking of eODs to lymph nodes. Applicants formed trimers, tetramers, and octamers of eOD by engineering genetic fusions of eOD to coiled-coil motifs that form trimers (PDBID:1GCN) and tetramers (PDBID:1GCL and PDBID:2B22). Applicants formed larger virus-like particles of eOD by engineering fusions to proteins that assemble into 24mers (protein name: O3-33, PDBID:3VCD), 60mers (protein name: Lumazine Synthase from Aquafex Aeolicus, PDBID:1HQK), and 180mers (protein name: PfV, PDBID:2E0Z). In all cases the fusions were expressed as secreted proteins from 293 cells.

The present invention also encompasses further multimeric forms of eOD. Applicants have successfully produced trimers, tetramers, octamers, 24mers, 60mers and 180mers of various eOD constructs. In several cases native N-linked glycosylations sites were removed from the multimeric protein to allow folding in the secretion pathway of mammalian cells. Multi-angle light scattering has been used to confirm the appropriate size of each multimer in solution. Several oligomers tested bound tightly to mature VRC01, confirming that the VRC01 epitope remains well-exposed. But VRC01 binding to eOD has a very slow off-rate, so binding to mature VRC01 does not provide a good test for avidity. Binding to the antibodies b12 and GLVRC01 was used to assess avidity, because binding of nearly all monomeric eOD variants to those antibodies normally has a rapid off-rate. Several oligomers tested provide significant avidity to binding interactions with b12, as judged by a slower off-rate compared to the b12interaction with monomeric eOD. Both 8mers and 60mers demonstrated significant avidity in interactions with GLVRC01.

The present invention encompasses multimers based on any other eOD described herein, such as, but not limited to, germline-targeting eODs, glycan-masked eODs, eODs with other stabilizing mutations and any and all such combinations. In an advantageous embodiment, the multimers may be based on eOD_VD(−).

In provisional patent application Ser. No. 61/546,465 (the '465 application), eOD_N386D below was referred to simply as "eOD" or "c1d1" but it should have been called "eOD_N386D" or "c1d1_N386D". See also, Science. 2011 Nov. 25;334(6059):1097-103. Epub 2011 Oct. 13.

eOD_N386D (originally disclosed in the '465 application as "eOD")
DTITLPCRPAPPPHCSSNITGLILTRDGGNSNNESEIFR-PGGGDMRDIARCQIAGTVVSTQLLLNGSLAE EEVVI-RSVNPTDNAKSICVQLNTSVEINCTGAGHCNISRAK-WNNTLKQIASKLREQFGNNKTIIFKQSSGGDPEIVT-HSFNCGGEFFYCDSTQLFNSTWFNSTWS eOD (not disclosed in the '465 application)
DTITLPCRPAPPPHCSSNITGLILTRDGGNSNNESEIFR-PGGGDMRDIARCOIAGTVVSTOLLLNGSLAEEEVVI-RSVNFTDNAKSICVQLNTSVEINCTGAGHCNISRAK-WNNTLKQIASKLREQFGNNKTIIFKQSSGGDPEIVT-HSFNCGGEFFYCNSTQLFNSTWFNSTWS Mutations to Improve Binding of Mature VRC01, in Some Cases with Benefits to Germline VRC01 Binding.

Applicants claim all possible combinations of the mutations in this section, on any eOD variant. "#" indicates a deletion relative to eOD_c1d1.

1. eOD_N276D (="eOD_D(-)")
DTITLPCRPAPPPHCSSNITGLILTRDGGNSNNESEIFRPGGG

DMRDIARCQIAGTVVSTQLLLNGSLAEEEVVIRSVDFTDNAKS

ICVQLNTSVEINCTGAGHCNISRAKWNNTLKQIASKLREQFGN

NKTIIFKQSSGGDPEIVTHSFNCGGEFFYCNSTQLFNSTWFNS

TWS 2. eOD_N276D (="EOD_VD(-)")
DTITLPCRPAPPPHCSSNITGLILTRDGGNSNNESEIFRPGGG

DMRDIARCQIAGTVVSTQLLLNGSLAEEEVVIRSVDFTDNAKS

ICVQLNTSVEINCTGAGHCNISRAKWNNTLKQIASKLREQFGN

NKTIIFKQSSGGDPEIVTHSFNCGGEFFYCNSTQLFNSTWFNS

TWS 3. eOD_L260F
DTITLPCRPAPPPHCSSNITGLILTRDGGNSNNESEIFRPGGG

DMRDIARCQIAGTVVSTQLFLNGSTLAEEEVVIRSVNFTDNAK

SICVQLNTSVEINCTGAGHCNISRAKWNNTLKQIASKLREQFG

NNKTIIFKQSSGGDPEIVTHSFNCGGEFFYCNSTQLFNSTWFN

STWS 4. eOD_L260F_N276D
DTITLPCRPAPPPHCSSNITGLILTRDGGNSNNESEIFRPGGG

DMRDIARCQIAGTVVSTQLFLNGSLAEEEVVIRSVDFTDNAKS

ICVQLNTSVEINCTGAGHCNISRAKWNNTLKQIASKLREQFGN

NKTIIFKQSSGGDPEIVTHSFNCGGEFFYCNSTQLFNSTWFNS

TWS 5. eOD_L260F_N276D_N463D
DTITLPCRPAPPPHCSSNITGLILTRDGGNSNDESEIFRPGGG

DMRDIARCQIAGTVVSTQLFLNGSLAEEEVVIRSVDFTDNAKS

ICVQLNTSVEINCTGAGHCNISRAKWNNTLKQIASKLREQFGN

NKTIIFKQSSGGDPEIVTHSFNCGGEFFYCNSTQLFNSTWFNS

TWS

-continued 6. eOD_I478N
DTITLPCRPAPPPHCSSNITGLILTRDGGNSNNESEIFRPGGG
DMRDNARCQIAGTVVSTQLLLNGSLAEEEVVIRSVNFTDNAKS
ICVQLNTSVEINCTGAGHCNISRAKWNNTLKQIASKLREQFGN
NKTIIFKQESGGDPEIVTHSFNCGGEFFYCNSTQLFNSTWFNS
TWS 7. eOD_Δ356
DTITLPCRPAPPPHCSSNITGLILTRDGGNSNNESEIFRPGGG
DMRDIARCQIAGTVVSTQLLLNGSLAEEEVVIRSVNFTDNAKS
ICVQLNTSVEINCTGAGHCNISRAKWNNTLKQIASKLREQFGN
KTIIFKQSSGGDPEIVTHSFNCGGEFFYCNSTQLFNSTWFNS
TWS 8. eOD_S387T
DTITLPCRPAPPPHCSSNITGLILTRDGGNSNNESEIFRPGGG
DMRDIARCQIAGTVVSTQLLLNGSLAEEEVVIRSVNFTDNAKS
ICVQLNTSVEINCTGAGHCNISRAKWNNTLKQIASKLREQFGN
NKTIIFKQSSGGDPEIVTHSFNCGGEFFYCNTTQLFNSTWFNS
TWS 9. eOD_V270I
DTITLPCRPAPPPHCSSNITGLILTRDGGNSNNESEIFRPGGG
DMRDIARCQIAGTVVSTQLLLLNGSLAEEEIVIRSVNFTDNAKS
ICVQLNTSVEINCTGAGHCNISRAKWNNTLKQIASKLREQFGN
NKTIIFKQSSGGDPEIVTHSFNCGGEFFYCNSTQLFNSTWFNS
TWS 10. eOD_T257S_L260F_S375W
DTITLPCRPAPPPHCSSNITGLILTRDGGNSNNESEIFRPGGG
DMRDIARCQIAGTVVSSQLFLNGSLAEEEVVIRSVNFTDNAKS
ICVQLNTSVEINCTGAGHCNISRAKWNNTLKQIASKLREQFGN
NKTIIFKQSSGGDPEIVTHWFNCGGEFFYCNSTQLFNSTWFNS
TWS 11. eOD_T257S_L260F_S375W_N276D
DTITLPCRPAPPPHCSSNITGLILTRDGGNSNNESEIFRPGGG
DMRDIARCQIAGTVVSSQLFLNGSLAEEEVVIRSVDFTDNAKS
ICVQLNTSVEINCTGAGHCNISRAKWNNTLKQIASKLREQFGN
NKTIIFKQSSGGDPEIVTHWFNCGGEFFYCNSTQLFNSTWFNS
TWS 12. eOD_T257S_L260F_S375W_N276D_N463D
DTITLPCRPAPPPHCSSNITGLILTRDGGNSNDESEIFRPGGG
DMRDIARCQIAGTVVSSQLFLNGSLAEEEVVIRSVDFTDNAKS
ICVQLNTSVEINCTGAGHCNISRAKWNNTLKQIASKLREQFGN
NKTIIFKQSSGGDPEIVTHWFNCGGEFFYCNSTQLFNSTWFNS
TWS eOD Variants Engineered to Improve Binding to Germline VRC01 and Other VH1-2 Antibodies Notes:
1. "#" indicates a deletion relative to eOD (also called cld1)
2. sequences may optionally have SASEGS appended to the N terminus
3. sequences may optionally have FD or G appended to the C terminus
4. sequences may optionally have an avitag appended to the C terminus, such as the following: GGSGGSGGLNDIFEAQKIEWHE
5. sequences may optionally have a histag appended to the C terminus, such as GTKHHHHHH Sequences:

1. eOD_VH1-2_v1.0
DTITLPCRPAPPRHCSSNITGLILTRDGGTSDDKTEIFRPGGG
DMRDIARCQIAGTVVSTQLLLNGSLAEEEVVIRSEDFRDNAKS
ICVQLNTSVEINCTGAGHCNISRAKWNNTLKQIASKLREQFGN
KTIIFKQSSGGDPEFVTHSFNCGGEFFYCDSTQLFDSTWFDS
TWS 2. eOD_VH1-2_v2.0
DTITLPCRPAPPPHCSSNITGLILTRGGGISDDKTEIFRPGGG
DMRDIARCQIAGTVVSTQLLLNGSLAEEEVVIRSEDFRDNSKS
ICVQLNTSVEINCTGAGHCNISRAKWNNTLKQIASKLREQFGN
KTIIFSQSLGGDPEFVTHSFNCGGEFFYCDSTQLFDSTWFDS
TWS 3. eOD_VH1-2_v2.1 (eOD_VH1-2_v2.0 + D.276N + R278T)
DTITLPCRPAPPPHCSSNITGLILTRGGGISDDKTEIFRPGGG
DMRDIARCQIAGTVVSTQLLLNGSLAEEEVVIRSENFTDNSKS
ICVQLNTSVEINCTGAGHCNISRAKWNNTLKQIASKLREQFGN
KTIIFSQSLGGDPEFVTHSFNCGGEFFYCDSTQLFDSTWFDS
TWS 4. eOD_VH1-2_v3.0 (eOD_VH1-2.0 + S471S + S401#)
DTITLPCRPAPPPHCSSNITGLILTRGGGISDDKTEIFRPSGG
DMRDIARCQIAGTVVSTQLLLNGSLAEEEVVIRSEDFRDNSKS
ICVQLNTSVEINCTGAGHCNISRAKWNNTLKQIASKLREQFGN
KTIIFSQSLGGDPEFVTHSFNCGGEFFYCDSTQLFDSTWFDS
TW#

5. eOD_VH1-2_v3.1 (eOD_VH1-2_v2.0 + K357R + S401#)
DTITLPCRPAPPRHCSSNITGLILTRGGGISDDKTEIFRPGGG
DMRDIARCQIAGTVVSTQLLLNGSLAEEEVVIRSEDFRDNSKS
ICVQLNTSVEINCTGAGHCNISRAKWNNTLKQIASKLREQFGN
RTIIFSQSLGGDPEFVTHSFNCGGEFFYCDSTQLFDSTWFDS
TW#

6. eOD_VH1-2_v4.0 (eOD_VH1-2_v3.0 + K464D + L260F + K357R)
DTITLPCRPAPPPHCSSNITGLILTRGGGISDDDTEIFRPSGG
DMRDIARCQIAGTVVSTQLFLNGSLAEEEVVIRSEDFRDNSKS 7. eOD_VH1-2_v4.1 (eOD_VH1-2_v3.0 + G457A + K464N + L260F + K357R)
DTITLPCRPAPPPHCSSNITGLILTRAGGISDDNTEIFRPSGG

DMRDIARCQIAGTVVSTQLFLNGSLAEEEVVIRSEDFRDNSKS

ICVQLNTSVEINCTGAGHCNISRAKWNNTLKQIASKLREQFGN

RTIIFSQSLGGDPEFVTHSFNCGGEFFYCDSTQLFDSTWFDSTW#

8. eOD_VH1-2_v4.2 (eOD_VH1-2_v3.0 + K464N + K357R)
DTITLPCRPAPPPHCSSNITGLILTRGGISDDNTEIFRPSGG

DMRDIARCQIAGTVVSTQLLLNGSLAEEEVVIRSEDFRDNSKS

ICVQLNTSVEINCTGAGHCNISRAKWNNTLKQIASKLREQFGN

RTIIFSQSLGGDPEFVTHSFNCGGEFFYCDSTQLFDSTWFDSTW#

9. eOD_VH1-2_v5.0 (eOD_VH1-2_v4.0 + I460V + E275V + S281A + L365S)
DTITLPCRPAPPPHCSSNITGLILTRGGGVSDDDTEIFRPSGG

DMRDIARCQIAGTVVSTQLFLNGSLAEEEVVIRSVDFRDNAKS

ICVQLNTSVEINCTGAGHCNISRAKWNNTLKQIASKLREQFGN

RTTIFSQSSGGDPEFVTHSFNCGGEFFYCDSTQLPDSTWFDSTW#

10. eOD_VH1-2_v5.1
DTITLPCRPAPPPHCSSNITGLILTRGGGVSDDDTEIFRPAGG

DMRDIARCQIAGTVVSTQLFLNGSLAEEEVVIRSVDFRDNAKS

ICVQLNTSVEINCTGAGHCNISRAKWNNTLKQIASKLREQFGN

RTIIFSQSSGGDREFVTHSFNCGGEFFYCDSTQLFDSTWFDSTW#

11. eOD_VH1-2_v5.2 (truncated form of v5.0)
DTITLPCRRAPPPHCSSNITGLILTRGGGVSDDDTEIFRPSGG

DMRDIARCQIAGTVVSTQLFLNGSLAEEEVVIRSVDFRDNAKS

ICVQLNTSVEINCTGAGHCNISRAKWNNTLKQIASKLREQFGN

RTIIFSQSSGGDPEFVTHSFNCGGEFFYCDSTQLFDSTWFD#

12. eOD_VH1-2_v6.0
DTITLPCRPAPPPHCSSNITGLILTRDGGVSNDETEIFRPSGG

DNRDIARCQIAGTVVSTQLFLNGSLAEEEVVIRSVDFRDNAKS

ICVQLNTSVEINCTGAGHCNISRAKWNNTLKQIASKLREQFGN

RTIIFKQSGGDPEFVTHSFNCGGEFFYCDSTQLFNSTWFNST##

13. eOD_VH1-2_v6.1 (v6.0 + V460N)
DTITLPCRPAPPPHCSSNITGLILTRDGGNSNDETEIFRPSGG

DMRDIARCQIAGTVVSTQLFLNGSLAEEEVVIRSVDFRDNAKS

ICVQLNTSVEINCTGAGHCNISRAKWNNTLKQIASKLREQFGN

RTIIFKQSSGGDPEFVTHSFNCGGEFFYCDSTQLFNSTWFNST##

14. eOD_VH1-2_v6.2 (v6.0 +T465S)
DTITLPCRPAPPPHCSSNITGLILTRDGGVSNDESEIFRPSGG

DMRDIARCQIAGTVVSTQLFLNGSLAEEEVVIRSVDFRDNAKS

ICVQLNTSVEINCTGAGHCNISRAKWNNTLKQIASKLREQFGN

RTIIFKQSSGGDPEFVTHSFNCGGEFFYCDSTQLFNSTWFNST##

15. eOD_VH1-2_v6.3 (v6.0 + S471G)
DTITLPCRPAPPPHCSSNITGLILTRDGGVSNDETEIFRPGGG

DMRDIARCQIAGTVVSTQLFLNGSLAEEEVVIRSVDFRDNAKS

ICVQLNTSVEINCTGAGHCNISRAKWNNTLKQIASKLREQFGN

RTIIFKQSSGGDPEFVTHSFNCGGEFFYCDSTQLFNSTWFNST##

16. eOD_VH1-2_v6.4 (v6.0 + F260L)
DTITLPCRPAPPPHCSSNITGLILTRDGGVSNDETEIFRRSGG

DMRDIARCQIAGTVVSTQLLLNGSLAEEEVVIRSVDFRDNAKS

ICVQLNTSVEINCTGAGHCNISRAKWNNTLKQIASKLREQFGN

RTIIFKQSSGGDPEFVTHSFNCGGEFFYCDSTQLFNSTWFNST##

17. eOD_VH1-2_v6.5 (v6.0 + R278T)
DTITLPCRPAPPPHCSSNITGLILTRDGGVSNDETEIFRPSGG

DMRDIARCQIAGTVVSTQLFLNGSLAEEEVVIRSVDFTDNAKS

ICVQLNTSVEINCTGAGHCNISRAKWNNTLKQIASKLREQFGN

RTIIFKQSSGGDPEFVTHSFNCGGEFFYCDSTQLFNSTWFNST##

18. eOD_VH1-2_v6.6 (v6.0 + R357K)
DTITLPCRPAPPPHCSSNITGLILTRDGGVSNDETEIFRPSGG

DMRDIARCQIAGTVVSTQLFLNGSLAEEEVVIRSVDFRDNAKS

ICVQLNTSVEINCTGAGHCNISRAKWNNTLKQIASKLREQFGN

KTIIFKQSSGGDPEFVTHSFNCGGEFFYCDSTQLFNSTWFNST##

19. eOD_VH1-2_v6.7 (v6.0 + F371I)
DTITLPCRPAPPPHCSSNITGLILTRDGGVSNDETEIFRPSGG

DMRDIARCQIAGTVVSTQLFLNGSLAEEEVVIRSVDFRDNAKS

ICVQLNTSVEINCTGAGHCNISRAKWNNTLKQIASKLREQFGN

RTIIFKQSSGGDPEIVTHSFNCGGEFFYCDSTQLFNSTWFNST##

20. eOD_VH1-2_v6.8 (v6.0 "minglyc")
DTITLPCRPAPPPHCSSNITGLILTRDGGVSNDETEIFRPSGG

DMRDIARCQIAGTVVSTQLFLNGSLAEEEVVIRSVDFRDNAKS

```
       TICVQLDTSVEIDCTGAGHCDISRAKWDNTLKQIASKLREQFGD
       #RTIIFKQSSGGDPEFVTHSFNCGGEFFYCDSTQLFDSTWFDST
       ##

21.    eOD_VH1-2_v7.0 (v6.0 + D463N + D386N)
       DTITLPCRPAPPPHCSSNITGLILTRDGGVSNNETEIFRPSGG
       DMRDIARCQIAGTVVSTQLFLNGSLAEEEVVIRSVDFRDNAKS
       TCVQLNTSVEINCTGAGHCNISRAKWNNTLKQIASKLREQFGN
       #RTIIFKQSSGGDPEFVTHSFNCGGEFFYCNSTQLFNSTWFNS
       T##

22.    eOD_VH1-2_v7.1 (v7.0 + V460N)
       DTITLPCRPAPPPHCSSNITGLILTRDGGNSNNETEIFRPSGG
       DMRDIARCQIAGTVVSTQLFLNGSLAEEEVVIRSVDFRDNAKS
       ICVQLNTSVEINCTGAGHCNISRAKWNNTLKQIASKLREQFGN
       #RTIIFKQSSGGDPEFVTHSFNCGGEFFYCNSTQLFNSTWFNS
       T##

23.    eOD_VH1-2_v7.2 (v7.0 + T465S)
       DTITLPCRPAPPPHCSSNITGLILTRDGGVSNNESEIFRPSGG
       DMRDIARCQIAGTVVSTQLFLNGSLAEEEVVIRSVDFRDNAKS
       ICVQLNTSVEINCTGAGHCNISRAKWNNTLKQIASKLREQFGN
       #RTIIFKQSSGGDPEFVTHSFNCGGEFFYCNSTQLFNSTWFNS
       T##

24.    eOD_VH1-2_v7.3 (v7.0 + S471G)
       DTITLPCRPAPPPHCSSNITGLILTRDGGVSNNETEIFRPGGG
       DMRDIARCQIAGTVVSTQLFLNGSLAEEEVVIRSVDFRDNAKS
       ICVQLNTSVEINCTGAGHCNISRAKWNNTLKQIASKLREQFGN
       #RTIIFKQSSGGDPEFVTHSFNCGGEFFYCNSTQLFNSTWFNS
       T##

25.    eOD_VH1-2_v7.4 (v7.0 + F260L)
       DTITLPCRPAPPPHCSSNITGLILTRDGGVSNNETEIFRPSGG
       DMRDIARCQIAGTVVSTQLLLNGSLAEEEVVIRSVDFRDNAKS
       ICVQLNTSVEINCTGAGHCNISRAKWNNTLKQIASKLREQFGN
       #RTIIFKQSSGGDPEFVTHSFNCGGEFFYCNSTQLFNSTWFNS
       T##

26.    eOD_VH1-2_v7.5 (v7.0 + R278T)
       DTITLPCRPAPPPHCSSNITGLILTRDGGVSNNETEIFRPSGG
       DMRDIARCQIAGTVVSTQLFLNGSLAEEEVVIRSVDFTDNAKS
       ICVQLNTSVEINCTGAGHCNISRAKWNNTLKQIASKLREQFGN
       #RTIIFKQSSGGDPEFVTHSFNCGGEFFYCNSTQLFNSTWFNS
       T##

27.    eOD_VH1-2_v7.6 (v7.0 + R357K)
       DTITLPCRPAPPPHCSSNITGLILTRDGGVSNNETEIFRPSGG
       DMRDIARCQIAGTVVSTQLFLNGSLAEEEVVIRSVDFRDNAKS
       ICVQLNTSVEINCTGAGHCNISRAKWNNTLKQIASKLREQFGN
       #KTIIFKQSSGGDPEFVTHSFNCGGEFFYCNSTQLFNSTWFNS
       T##

28.    eOD_VH1-2_v7.7 (v7.0 + F371I)
       DTITLPCRPAPPPHCSSNITGLILTRDGGVSNNETEIFRPSGG
       DMRDIARCQIAGTVVSTQLFLNGSLAEEEVVIRSVDFRDNAKS
       ICVQLNTSVEINCTGAGHCNISRAKWNNTLKQIASKLREQFGN
       #RTIIFKQSSGGDPEIVTHSFNCGGEFFYCNSTQLFNSTWFNS
       T##

29.    eOD_VH1-2_v7.8 (v7.0 + D276N + R278T)
       DTITLPCRPAPPPHCSSNITGLILTRDGGVSNNETEIFRPSGG
       DMRDIARCQIAGTVVSTQLFLNGSLAEEEVVIRSVNFTDNAKS
       ICVQLNTSVEINCTGAGHCNISRAKWNNTLKQIASKLREQFGN
       #RTIIFKQSSGGDPEFVTHSFNCGGEFFYCNSTQLFNSTWFMS
       T##

30.    eOD_RheVH1-2_v1.0
       DTITLPCRPAPPPHCSSNITGLILTRAGGVSDNNTEIFFPSGG
       DMRDIARCQIAGTVVSTQLFLNGSLAEEEVVIRSVDFRDNAKS
       ICVQLNTSVEINCTGAGHCNISRAKWNNTLKQIASKLREQFGN
       #RTIIFSQSTGGDPEFVTHSFNCGGEFFYCNSTQLFNSTWFNS
       T##

31.    eOD_RheVH1-2_v2.0
       DTITLPCRPAPPPHCSSNITGLILGRAGGASDDNTEIFYPSGG
       DMRDIARCQIAGTVVSTQLFLNGSLAEEEVVIRSVDFRDNAKS
       ICVQLNTSVEINCTGAGHCNISRAKWNNTLKQIASKLREQFGN
       #RTIIFSQSTGGDPEIVTHSFNCGGEFFYCNSTQLFNSTWFNS
       TW#

32.    eOD_RheVH1-2_v2.1
       DTITLPCRPAPPPHCSSNITGLILTRAGGVSNNETEIFFPSGG
       DMRDIARCQIAGTVVSTQLFLNGSLAEEEVVIRSVDFRDNAKS
       ICVQLNTSVEINCTGAGHCNTSRAFWNNTLKQIASKLREQFGN
       #RTIIFKQSSGGDPEFVTHSFNCGGEFFYCNSTQLFNSTWFNS
       T##

33.    core_gp120_VH1-2_v1.0
       VWKEATTTLFCASDAKAYDTEVHNVWATHACVPTDPNPQEVEL
       ENVTENFNMWKNNMVEQMHEDIISLWDQSLKPCVKLTGGSVIT
       QACPKISFEPIPIHYCAPAGFAILKCKDKKFNGKGPCSNVSTV
       QCTHGIRPVVSTQLLLNGSLAEEEVVIRSENFADNAKTIIVQL
       NESVEINCTRPNNGGSGSGGDIRQAHCNLSRAKWNDTLNKIVI
       KLREQFGNKTIVFKHSSGGDPEIVTHSFNCGGEFFYCNSTQLF
       NSTWNVTEESNNTVENNTITLPCRIKQIINMWQKVGRAMYAPP
       IRGQIRCSSNITGLLLTRDGGPEDNKTEVFRPGGGDMRDNWRS
       ELYKYKVVKIE
```

34. core_gp120_VH1-2_v2.0
VWKDATTTLFCASDAKAHETEVHNVWATHACVPTDPNPQRVEL
KNVTENFNMWKNNMVEQMHEDIISLWDQSLKPCVKLTGGSVIT
QACPKVSFEPIPIHYCAPAGFAILKCKDKKFNGKGPCSNVSTV
QCTHGIRPVVSTQLLLNGSLAEEEVVIRSEDFRNNAKIIIVQL
NESVEINCTGAGHCNLSRAKWNDTLNKIVIKLREQFGNKTIVF
KHSSGGDPEIVTHSFNCGGEFFYCNSTQLFNSTWNVTEESNNT
VENNTITLPCRIKQIINMWQEVGRAMYAPPIRGQIRCSESNIT
GLLLIRDGGPEDNKTEIFRPGGGDMRDNWRSELYKYKVVKIE 35. core_gp120_VH1-2_v2.1
VWKDATTTLFCASDAKAHETEVHNVWATHACVPTDPNPQEVEL
KNVTENFNMWKNNMVEQMHEDIISLWDQSLKPCVKLTGGSVIT
QACPKVSFEPIPIHYCAPAGFAILKCKDKKFNGKGPCSNVSTV
QCTHGIRPVVSTQLLLNGSLAEEEVVIRSEDFRNNAKIIIVQL
NESVEINCTGAGHCNLSRAKWNDTLNKIVIKLREQFGNKTIVF
SHSSGGDPEFVTHSFNCGGEFFYCNSTQLFNSTWNVTEESNNT
VENNTITLPCRIKQTINMWQEVGPIRGQIRCSSNITGLLLIRD
GGAEDNKTEIFRPGGGDMRDNWRSELYKYKVVKIE 36. full_gp120_BaL_VH1-2_v1.0
MRVKEKYQHLWRWGWRWGTMLLGMLMICSATEKLWVTVYYGVP
VWKEATTTLFCASDAKAYDTEVHNVWATHACVPTDPNPQEVEL
ENVTENFNMWKNNMVEQMHEDIISLWDQSLKPCVKLTPLCVTL
NCTDLRNATNGNDTNTTSSSREMMGGGEMKNCSFKITTNIRGK
VQKEYALFYELDIVPIDNNSNNRYRLISCNTSVITQACPKISF
EPIPIHYCAPAGFAILKCKDKKFNGKGPCSNVSTVQCTHGIRP
VVSTQLLLNGSLAEEEVVIRSENFADNAKTIIVQLNESVEINC
TRPNNNTRKSIHIGPGRALYTTGEIIGDIRQAHCNLSRAKWND
TLNKIVIKLREQFGNKTIVFKHSSGGDPEIVTHSFNCGGEFFY
CNSTQLFNSTWNVTEESNNTVENNTITLPCRIKQIINMWQKVG
RAMYAPPIRGQIRCSSNITGLLLTRDGGPEDNKTEVFRPGGGD
MRDNWRSELYKYKVVKIEPLGVAPTKAKRRVVQ 37. eOD_VH1-2_VH1-8_v1.0
DTITLPCRPAPPPHCSSNITGLILTRLGGVSNDETEIFKPSGG
DWRIDIARCQIAGTVVSTQLFLNGSLAEEEVVIRSVDFRDNAK
SICVQLNTSVEINCTGAGHCNISRAKWNNTLKQIASKLREQFG
NRTIIFKQSSGGDPEFVTHSFNCGGEFFYCDSTQLFNSTWFN
ST All of the mutations relative to eOD (=c1d1) in the eOD variants in this section are listed below, in both eOD numbering (left column) and HxB2 numbering (right column). Each of these mutations has been identified as helpful for improving germline VH1-2 binding to eOD. Applicants claim all variants of eOD that include any combination of these mutations. Based on the HxB2 numbering which uniquely defines a position in any HIV Env sequence once it has been aligned to the HxB2 sequence, Applicants also claim any combination of these mutations on any ENV construct from any HIV strain.

| eOD_mut_id | eOD_numbering | HxB2_numbering |
|---|---|---|
| 1 | A84S | A281S |
| 2 | D27A | D457A |
| 3 | D27G | D457G |
| 4 | E34D | E464D |
| 5 | E34K | E464K |
| 6 | E34N | E464N |
| 7 | G41S | G471S |
| 8 | L63F | L260F |
| 9 | N30A | N460A |
| 10 | N30I | N460I |
| 11 | N30T | N460T |
| 12 | N30V | N460V |
| 13 | N32D | N462D |
| 14 | N33D | N463D |
| 15 | N79D | N276D |
| 16 | N92D | N289D |
| 17 | N98D | N295D |
| 18 | R39F | R469F |
| 19 | R39Y | R469Y |
| 20 | S35T | S465T |
| 21 | T25G | T455G |
| 22 | T81R | T278R |
| 23 | V78E | V275E |
| 24 | I145F | I371F |
| 25 | K131R | K357R |
| 26 | K136S | K362S |
| 27 | N106D | N332D |
| 28 | N113D | N339D |
| 29 | N129D | N355D |
| 30 | N130# | N356# |
| 31 | N160D | N386D |
| 32 | N166D | N392D |
| 33 | N171D | N397D |
| 34 | S139L | S365L |
| 35 | S139T | S365T |
| 36 | S172# | S398# |
| 37 | S175# | S401# |
| 38 | T173# | T399# |
| 39 | W174# | W400# |

All of the mutations and modifications in core_gp120_VH1-2_v2.0 and core_gp120_VH1-2_v2.1 relative to core_gp120_VH1-2_v1.0 are shown below in two Blast alignments. These mutations and modifications were identified to improve binding of core gp120 to germline VH1-2 antibodies. As discussed above, removal of the glycosylation site at 276 also improves binding of germline VH1-2 antibodies and appears essential for the germline binding to core_gp120_VH1-2_v1.0. Applicants claim all combinations of the core_gp120_VH1-2_v2.0 and core_gp120_VH1-2_v2.1 mutations and modifications relative to core_gp120_VH1-2_v1.0, and all combinations of these mutations/modifications with any mutation or mutations that removes a glycosylation site at position 276, in any HIV Env construct from any strain.

```
Query = core_gp120_VH1-2_v2.0
Sbjct = core_gp120_VH1-2_v1.0
Query:  1 VWKDATTTLFCASDAKAHETEVHNVWATHACVPTDPNPQEVELKNVTENFNMWKNNMVEQ 60
          VWK+ATTTLFCASDAKA++TEVHNVWATHACVPTDPNPQEVEL+NVTENFNMWKNNMVEQ
Sbjct:  1 VWKEATTTLFCASDAKAYDTEVHNVWATHACVPTDPNPQEVELENVTENFNMWKNNMVEQ 60
```

```
Query:    61  MHEDIISLWDQSLKPCVKLTGGSVITQACPKVSFEPIPIHYCAPAGFAILKCKDKKFNGK  120
              MHEDIISLWDQSLKPCVKLTGGSVITQACPK+SFEPIPIHYCAPAGFAILKCKDKKFNGK
Sbjct:    61  MHEDIISLWDQSLKPCVKLTGGSVITQACPKISFEPIPIHYCAPAGFAILKCKDKKFNGK  120

Query:   121  GPCSNVSTVQCTHGIRPVVSTQLLLNGSLAEEEVVIRSEDFRNNAKIIIVQLNESVEINC  180
              GPCSNVSTVQCTHGIRPVVSTQLLLNGSLAEEEVVIRSE+F +NAK IIVQLNESVEINC
Sbjct:   121  GPCSNVSTVQCTHGIRPVVSTQLLLNGSLAEEEVVIRSENFADNAKTIIVQLNESVEINC  180

Query:   181  T-----GAG--------HCNLSRAKWNDTLNKIVIKLREQFGNKTIVFKHSSGGDPEIVT  227
              T     G+G        HCNLSRAKWNDTLNKIVIKLREQFGNKTIVFKHSSGGDPEIVT
Sbjct:   181  TRPNNGGSGSGGDIRQAHCNLSRAKWNDTLNKIVIKLREQFGNKTIVFKHSSGGDPEIVT  240

Query:   228  HSFNCGGEFFYCNSTQLFXXXXXXXXXXXXXXXXXXXXITLPCRIKQIINMWQEVGRAMYAP  287
              HSFNCGGEFFYCNSTQLF                    ITLPCRIKQIINMWQ+VGRAMYAP
Sbjct:   241  HSFNCGGEFFYCNSTQLFNSTWNVTEESNNTVENNTITLPCRIKQIINMWQKVGRAMYAP  300

Query:   288  PIRGQIRCSSNITGLLLIRDGGPEDNKTEIFRPGGGDMRDNWRSELYKYKVVKIE  342
              PIRGQIRCSSNITGLLL RDGGPEDNKTE+FRPGGGDMRDNWRSELYKYKVVKIE
Sbjct:   301  PIRGQIRCSSNITGLLLTRDGGPEDNKTEVFRPGGGDMRDNWRSELYKYKVVKIE  350

Query = core_gp120_VH1-2_v2.1
Sbjct = core_gp120_VH1-2_v1.0
Query:     1  VWKDATTTLFCASDAKAHETEVHNVWATHACVPTDPNPQEVELKNVTENFNMWKNNMVEQ   60
              VWK+ATTTLFCASDAKA++TEVHNVWATHACVPTDPNPQEVEL+NVTENFNMWKNNMVEQ
Sbjct:     1  VWKEATTTLFCASDAKAYDTEVHNVWATHACVPTDPNPQEVELENVTENFNMWKNNMVEQ   60

Query:    61  MHEDIISLWDQSLKPCVKLTGGSVITQACPKVSFEPIPIHYCAPAGFAILKCKDKKFNGK  120
              MHEDIISLWDQSLKPCVKLTGGSVITQACPK+SFEPIPIHYCAPAGFAILKCKDKKFNGK
Sbjct:    61  MHEDIISLWDQSLKPCVKLTGGSVITQACPKISFEPIPIHYCAPAGFAILKCKDKKFNGK  120

Query:   121  GPCSNVSTVQCTHGIRPVVSTQLLLNGSLAEEEVVIRSEDFRNNAKIIIVQLNESVEINC  180
              GPCSNVSTVQCTHGIRPVVSTQLLLNGSLAEEEVVIRSE+F +NAK IIVQLNESVEINC
Sbjct:   121  GPCSNVSTVQCTHGIRPVVSTQLLLNGSLAEEEVVIRSENFADNAKTIIVQLNESVEINC  180

Query:   181  T-----GAG--------HCNLSRAKWNDTLNKIVIKLREQFGNKTIVFSHSSGGDPEFVT  227
              T     G+G        HCNLSRAKWNDTLNKIVIKLREQFGNKTIVF HSSGGDPE VT
Sbjct:   181  TRPNNGGSGSGGDIRQAHCNLSRAKWNDTLNKIVIKLREQFGNKTIVFKHSSGGDPEFVT  240

Query:   228  HSFNCGGEFFYCNSTQLFXXXXXXXXXXXXXXXXXXXXITLPCRIKQIINMWQEVG------  281
              HSFNCGGEFFYCNSTQLF                    ITLPCRIKQIINMWQ+VG
Sbjct:   241  HSFNCGGEFFYCNSTQLFNSTWNVTEESNNTVENNTITLPCRIKQIINMWQKVGRAMYAP  300

Query:   282  PIRGQIRCSSNITGLLLIRDGGAEDNKTEIFRPGGGDMRDNWRSELYKYKVVKIE  336
              PIRGQIRCSSNITGLLL RDGG EDNKTE+FRPGGGDMRDNWRSELYKYKVVKIE
Sbjct:   301  PIRGQIRCSSNITGLLLTRDGGPEDNKTEVFRPGGGDMRDNWRSELYKYKVVKIE  355
``` eOD Glycan Masking.

In these sequences Applicants do not include the "VD(−)" mutations N276D and N463D, though the glycan mutants were originally tested on that background. As these glycosylation mutations are transferable to any eOD variant, Applicants claim all combinations of the following glycosylation mutations on any eOD variant.

1. eOD_g2
   DTITLPCRPAPPPHCSSNITGLILTRDGGNSNNESEIFRPGGG
   DMRDIANCSIAGTVVSTQLLLNGSLAEEEVVIRSVNFTDNAKS
   ICVQLNTSVEINCTGAGHCNISRAKWNNTLKQIASKLREQFGN
   NKTIIFKQSSGGDPEIVTHSFNCGGEFFYCNSTQLFNSTWFNS
   TWS 2. eOD_g3
   DTITLPCRPAPPPHCSSNITGLILTRDGGNSNNESEIFRPGGG
   DMRDIARCQNASVVSTQLLLNGSLAEEEVVIRSVNFTDNAKS
   ICVQLNTSVEINCTGAGHCNISRAKWNNTLKQIASKLREQFGN
   NKTIIFKQSSGGDPEIVTHSFNCGGEFFYCNSTQLFNSTWFNS
   TWS 3. eOD_g4
   DTITLPCRPAPPPHCSSNITGLILTRDGGNSNNESEIFRPGGG
   DMRDIARCQIAGNVTSTQLLLNGSLAEEEVVIRSVNFTDNAKS
   ICVQLNTSVEINCTGAGHCNISRAKWNNTLKQIASKLREQFGN
   NKTIIFKQSSGGDPEIVTHSFNCGGEFFYCNSTQLFNSTWFNS
   TWS 4. eOD_g5
   DTITLPCRPAPPPHCSSNITGLILTRDGGNSNNESEIFRPGGG
   DMRDIARCQIAGTVVSTQLLLNGSLAEEEVVIRSVNFTDNAKS
   ICVQLNTSVEINCTGAGHCNISRAKWNNTLKQIASKLRENFSN
   NKTIIFKQSSGGDPEIVTHSFNCGGEFFYCNSTQLFNSTWFNS
   TWS 5. eOD_g6
   DTITLPCNPSPPPHCSSNITGLILTRDGGNSNNESEIFRPGGG
   DMRDIARCQIAGTVVSTQLLLNGSLAEEEVVIRSVNFTDNAKS
   ICVQLNTSVEINCTGAGHCNISRAKWNNTLKQIASKLREQFGN

```
        NKTIIFKQSSGGDPEIVTHSFNCGGEFFYCNSTQLFNSTWFNS
        TWS
6.      eOD_g7
        DTITLPCRNATPPHCSSNITGLILTRDGGNSNNESEIFRPGGG
        DMRDIARCQIAGTVVSTQLLLNGSLAEEEVVIRSVNFTDNAKS
        ICVQLNTSVEINCTGAGHCNISRAKWNNTLKQIASKLREQFGN
        NKTIIFKQSSGGDPEIVTHSFNCGGEFFYCNSTQLFNSTWFNS
        TWS
7.      eOD_g8
        DTITLPCRPAPPPHCSSNITGLILTRDGGNSNNESEIFRPGGG
        DMRDIARCQIAGTVVSTQLLLNGSLAEEEVVIRSVNFTDNAKS
        ICVQLNTSVEINCTGAGHCNISRAKWNNTLKQIASKLREQFGN
        NKTIIFKQSSGGDPEIVTHSFNCGNETFYCNSTQLFNSTWFNS
        TWS
8.      eOD_g3-6-8
        DTITLPCNPSPPPHCSSNITGLILTRDGGNSNNESEIFRPGGG
        DMRDIARCQNASTVVSTQLLLNGSLAEEEVVIRSVNFTDNAKS
        ICVQLNTSVEINCTGAGHCNISRAKWNNTLKQIASKLREQFGN
        NKTIIFKQSSGGDPEIVTHSFNCGNETFYCNSTQLFNSTWFNS
        TWS
9.      eOD_g2-6-8
        DTITLPCNPSPPPHCSSNITGLILTRDGGNSNNESEIFRPGGG
        DMRDIANCSIAGTVVSTQLLLNGSLAEEEVVIRSVNFTDNAKS
        ICVQLNTSVEINCTGAGHCNISRAKWNNTLKQIASKLREQFGN
        NKTIIFKQSSGGDPEIVTHSFNCGNETFYCNSTQLFNSTWFNS
        TWS
10.     eOD_g2-4-6-8
        DTITLPCNPSPPPHCSSNITGLILTRDGGNSNNESEIFRPGGG
        DMRDIANCSIAGNVTSTQLLLNGSLAEEEVVIRSVNFTDNAKS
        ICVQLNTSVEINCTGAGHCNISRAKWNNTLKQIASKLREQFGN
        NKTIIFKQSSGGDPEIVTHSFNCGNETFYCNSTQLFNSTWFNS
        TWS
11.     eOD_g2-5-6-8
        DTITLPCNPSPPPHCSSNITGLILTRDGGNSNNESEIFRPGGG
        DMRDIANCSIAGTVVSTQLLLNGSLAEEEVVIRSVNFTDNAKS
        ICVQLNTSVEINCTGAGHCNISRAKWNNTLKQIASKLRENFSN
        NKTIIFKQSSGGDPEIVTHSFNCGNETFYCNSTQLFNSTWFNS
        TWS
12.     eOD_g2-4-5-6-8
        DTITLPCNPSPPPHCSSNITGLILTRDGGNSNNESEIFRPGGG
        DMRDIANCSIAGNVTSTQLLLNGSLAEEEVVIRSVNFTDNAKS
        ICVQLNTSVEINCTGAGHCNISRAKWNNTLKQIASKLRENFSN
        NKTIIFKQSSGGDPEIVTHSFNCGNETFYCNSTQLFNSTWFNS
        TWS
``` eOD Multimers

Notes:
1. The linkers (shown in bold) here are used as examples but a diverse arrays of linkers could be employed. In many examples below a flexible GlySer linker is used, such as (GGSGGSGG or GGSGGSGGSGGSGGG), but a wide variety of types of flexible linkers could be used instead. In some examples below a known T-helper epitope (Tetanus toxoid p2 peptide, QYIKANSKFIGITEL) is employed as a linker (with GS and SG flanking, GSQYIKANSKFIGITELSG). A variety of other T-helper epitopes could be used instead or in addition.
2. The sequences here show the eOD variant "eOD_VD(−)" fused with various multimerization domains, but any of the eOD sequences listed in this application may ne substituted for eOD_VD(−) to make other fusions.
3. A histag such as HHHHHH or HHHHHHGSG or GTKHHHHHH may be appended to the N-terminus or C-terminus of any of the 3mer, 4mer, or 8mer sequences.

Sequences:

```
1.  eOD_VD(-)_3mer_1gcm_1
    RMKQIEDKIEEILSKIYHIENEIARIKKLIGERGGSGGSGGDT
    ITLPCRPAPPPHCSSNITGLILTRDGGNSNDESEIFRPGGGDM
    RDIARCQIAGTVVSTQLLLNGSLAEEEVVIRSVDFTDNAKSIC
    VQLNTSVEINCTGAGHCNISRAKWNNTLKQIASKLREQFGNNK
    TIIFKQSSGGDPEIVTHSFNCGGEFFYCNSTQLFNSTWFNST
    WS
2.  eOD_VD(-)_3mer_1gcm_2
    DTITLPCRPAPPPHCSSNITGLILTRDGGNSNDESEIFRPGGG
    DMRDIARCQIAGTVVSTQLLLNGSLAEEEVVIRSVDFTDNAKS
    ICVQLNTSVEINCTGAGHCNISRAKWNNTLKQIASKLREQFGN
    NKTIIFKQSSGGDPEIVTHSFNCGGEFFYCNSTQLFNSTWFNS
    TWSGGSGGSGGRMKQIEDKIEEILSKIYHIENEIARIKKLIG
    ER
3.  eOD_VD(-)_4mer_1gcl_1
    RMKQIEDKLEEILSKLYHIENELARIKKLLGERGGSGGSGGDT
    ITLPCRPAPPPHCSSNITGLILTRDGGNSNDESEIFRPGGGDM
    RDIARCQIAGTVVSTQLLLNGSLAEEEVVIRSVDFTDNAKSIC
    VQLNTSVEINCTGAGHCNISRAKWNNTLKQIASKLREQFGNNK
    TIIFKQSSGGDPEIVTHSFNCGGEFFYCNSTQLFNSTWFNST
    WS
4.  eOD_VD(-)_4mer_1gcl_2
    DTITLPCRPAPPPHCSSNITGLILTRDGGNSNDESEIFRPGGG
    DMRDIARCQIAGTVVSTQLLLNGSLAEEEVVIRSVDFTDNAKS
    ICVQLNTSVEINCTGAGHCNISRAKWNNTLKQIASKLREQFGN
```

NKTIIFKQSSGGDPEIVTHSFNCGGEFFYCNSTQLFNSTWFNS
TWSGGSGGSGGRMKQIEDKLEEILSKLYHIENELARIKKLLG
ER 5. eOD_VD(-)_4mer_2b22_1
MKVKQLEDVVEELLSVNYHLENVVARLKKLVGER**SGGSGGSGG
G**DTITLPCRPAPPPHCSSNITGLILTRDGGNSNDESEIFRPGG
GDMRDIARCQIAGTVVSTQLLLNGSLAEEEVVIRSVDFTDNAK
SICVQLNTSVEINCTGAGHCNISRAKWNNTLKQIASKLREQFG
NNKTIIFKQSSGGDPEIVTHSFNCGGEFFYCNSTQLFNSTWFN
STWS 6. eOD_VD(-)_4mer_2b22_2
DTITLPCRPAPPPHCSSNITGLILTRDGGNSNDESEIFRPGGG
DMRDIARCQIAGTVVSTQLLLNGSLAEEEVVIRSVDFTDNAKS
ICVQLNTSVEINCTGAGHCNISRAKWNNTLKQIASKLREQFGN
NKTIIFKQSSCGDPEIVTHSFNCGGEFFYCNSTQLFNSTWFNS
TWSGGSGGSGGSGGGMKVKQLEDVVEELLSVNYHLENVVARLK
KLVGER 7. eOD_VD(-)_8mer_1gcl
DTITLPCRPAPPPHCSSNITGLILTRDGGNSNDESEIFRPGGG
DMRDIARCQIAGTVVSTQLLLNGSLAEEEVVIRSVDFTDNAKS
ICVQLNTSVEINCTGAGHCNISRAKWNNTLKQIASKLREQFGN
NKTIIFKQSSGGDPEIVTHSFNCGGEFFYCNSTQLFNSTWFNS
TWSGGSGGSGGSGGGRMKQTEDKLEEILSKLYHIENELARIKK
LLGERGGSGGSGGSGGGDTITLPCRPAPPPHCSSNITGLILTR
DGGNSNDESEIFRPGGGDMRDIARCQIAGTVVSTQLLLNGSLA
EEEVVIRSVDFTDNAKSICVQLNTSVEINCTGAGHCNISRAKW
NNTLKQIASKLREQFGNNKTIIFKQSSGGDPEIVTHSFNCGGEF
FYCNSTQLFNSTWFNSTWS 8. eOD_VD(-)_8mer_2b22
DTITLPCRPAPPPHCSSNITGLILTRDGGNSNDESEIFRPGGG
DMRDIARCQIAGTVVSTQLLLNGSLAEEEVVIRSVDFTDNAKS
ICVQLNTSVEINCTGAGHCNISRAKWNNTLKQIASKLREQFGN
NKTIIFKQSSGGDPEIVTHSFNCGGEFFYCNSTQLFNSTWFNS
TWSGGSGGSGGSGGGMKVKQLEDVVEELLSVNYHLENVVARLK
KLVGERGGSGGSGGSGGGDTITLPCRPAPPPHCSSNITGLILT
RDGGNSNDESEIFRPGGGDMRDIARCQIAGTVVSTQLLLNGSL
AEEEVVIRSVDFTDNAKSICVQLNTSVEINCTGAGHCNISRAK
WNNTLKQIASKLREQFGNNKTIIFKQSSGGDPEIVTHSFNCGG
EFFYCNSTQLFNSTWFNSTWS 9. eOD_VD(-)_24mer_3vcd_1
DTITLPCRPAPPPHCSSNITGLILTRDGGNSNDESEIFRPGGG
DMRDIARCQIAGTVVSTQLLLNGSLAEEEVVIRSVDFTDNAKS
ICVQLNTSVEINCTGAGHCNISRAKWNNTLKQIASKLREQFGN
NKTIIFKQSSGGDPEIVTHSFNCGGEFFYCNSTQLFNSTWFNS
TWSGGSGGSGGSGGSGGGMSQAIGILELTSIAAGMELGDAMLK
SANVDLLVSKTISPGKFLLMLGGDIGAIQQAIETGTSQAGELL
VDSLVLANIHPSVLPAISGLNSVDKRQAVGIVETWSVAAAISA
ADRAVKGSDVTLVRVHMAFGIGGKAYMVVAGDVSDVALAVTVA
SSSAGAYGLLVYASLIPRPHEAMWRQMVEG 10. eOD_VD(-)_24mer_3vcd_2
MSQAIGILELTSIAAGMELGDAMLKSANVDLLVSKTISPSKFL
LMLGGDIGAIQQAIETGTSQAGELLVDSLVLANIHPSVLPAIS
GLNSVDKRQAVGIVETWSVAAAISAADRAVKGSDVTLVRVHMA
FGIGGKAYMVVAGDVSDVALAVTVASSSAGAYGLLVYASLIPR
PHEAMWRQMVEGGGSGGSGGSGGSGGGDTITLPCRPAPPPHCS
SNITGLILTRDGGNSNDESEIFRPGGGDMRDIARCQIAGTVVS
TQLLLNGSLAEEEVVIRSVDFTDNAKSICVQLNTSVEINCTGA
GHCNISRAKWNNTLKQIASKLREQFGNNKTIIFKQSSGGDPEI
VTHSFNCGGEFFYCNSTQLFNSTWFNSTWS 11. eOD_VD(-)_60mer_1hqk_1
MQIYEGKLTAEGLRFGIVASRFNHALVDRLVEGAIDAIVRHGG
REEDITLVRVPGSWEIPVAAGELARKEDIDAVIAIGVLIRGAT
PHFDYIASEVSKGLADLSLELRKPITFGVITADTLEQAIERAG
TKHGNKGWEAALSAIEMANLFKSLRGGSGGSGGSGGSGGGDTI
TLPCRPAPPPHCSSNITGLILTRDGGNSNDESEIFRPGGGDMR
DTARCQIAGTVVSTQLLLNGSLAEEEVVIRSVDFTDNAKSICV
QLNTSVEINCTGAGHCNISRAKWNNTLKQIASKLREQFGNNKT
IIFKQSSGGDPEIVTHSFNCGGEFFYCNSTQLFNSTWFNSTWS 12. eOD_VD(-)_60mer_1hqk_2
DTITLPCRPAPPPHCSSNITGLILTRDGGNSNDESEIFRPGGG
DMRDIARCQIAGTVVSTQLLLNGSLAEEEVVIRSVDFTDNAKS
ICVQLNTSVEINCTGAGHCNISRAKWNNTLKQIASKLREQFGN
NKTIIFKQSSGGDPEIVTHSFNCGGEFFYCNSTQLFNSTWFNS
TWSGGSGGSGGSGGSGGGMQIYEGKLTAEGLRFGIVASRFNHA
LVDRLVEGAIDAIVHGGREEDITLVRVPGSWEIPVAAGELARK
EDIDAVIAIGVLIRGATPHFDYIASEVSKGLADLSLELRKPIT
FGVITADTLEQAIERAGTKHGNKGWEAALSAIEMANLFKSLR 13. eOD_VD(-)_60mer_1hqk_3
MQIYEGKLTAEGLRFGIVASRFNHALVDRLVEGAIDAIVRHGG
REEDITLVRVPGSWEIPVAAGELARKEDIDAVIAIGVLIRGAT
PHFDYIASEVSKGLADLSLELRKPITFGVITADTLEQAIERAG
TKHGNKGWEAALSAIEMANLFKSLRGSQYIKANSKFIGITELS
GDTITLPCRPAPPPHCSSNITGLILTRDGGNSNDESEIFRPGG -continued GDMRDIARCQIAGTVVSTQLLLNGSLAEEEVVIRSVDFTDNAK
SICVQLNTSVEINCTGAGHCNISRAKWNNTLKQIASKLREQFG

NNKTIIFKQSSGGDPEIVTHSFNCGGEFFYCNSTQLFNSTWFN

STWS 14. eOD_VD(-)_60mer_1hqk_4
DTITLPCRPAPPPHCSSNITGLILTRDGGNSNDESEIFRPGGG

DMRDIARCQIAGTVVSTQLLLNGSLAEEEVVIRSVDFTDNAKS

ICVQLNTSVEINCTGAGHCNISRAKWNNTLKQIASKLREQFGN

NKTIIFKQSSGGDPEIVTHSFNCGGEFFYCNSTQLFNSTWFNS

TWSGSQYIKANSKFIGITELSGMQIYEGKLTAEGLRFGIVASR

FNHALVDRLVEGAIDAIVRHGGREEDITLVRVPGSWEIPVAAG

ELARKEDIDAVIAIGVLIRGATPHFDYIASEVSKGLADLSLEL

RKPITFGVITADTLEQAIERAGTKHGNKGWEAALSAIEMANLF

KSLR 15. eOD_VD(-)_180mer_2e0z
VEYFEKLRSALLDGVNKGRSLLKHLPVTRIEGQSFRVDIIKFE

DGVRVVKQEYKPIPLLKKKFYVGIRELNDGTYDVSIATKAGEL

LVKDEESLVIREILSTEGIKKMKLSSWDNPEEALNDLMNALQE

ASDASAGPFGLITNPKRYAKLLKTYEKSGKMLVEVLKEIFRGG

ITVTLNIDENKVIIFANTPAVLDVVVGQDVTLQELGPEGDDVA

FLVSEAIGIRIKNPEAIVVLEGGSGGSGGSGGSGGGDTITLPC

RPAPPPHCSSNITGLILTRDGGNSNDESEIFRPGGGDMRDIAR

CQIAGTVVSTQLLLNGSLAEEEVVIRSVDFTDNAKSICVQLNT

SVEINCTGAGHCNISRAKWNNTLKQIASKLREQFGNNKTIIFK
QSSGGDPEIVTHSFNCGGEFFYCNSTQLFNSTWFNSTWS HIV Strains Lacking a Glycosylation Site at 276.

HIV strains lacking glycan at 276 out of 2867 different sequences from the LANL database:

| strain_name | 276 | 277 | 278 |
|---|---|---|---|
| A.CM.97.97CM_MP640.AM279366 | S | L | T |
| A.UG.07.191955_A11.HM215272 | N | I | N |
| A1.KE.00.KNH1211.AF457070 | N | I | A |
| A1.KE.04.QG984_21M_ENV_A3.FJ866117 | D | I | S |
| A1.TZ.01.A341.AY253314 | N | I | A |
| B.AU.96.MBCD36.AF042105 | N | F | M |
| B.CH.x.NAB8pre_cl_11.EU023927 | D | F | S |
| B.CN.06.CNHLJSM06048.EU131794 | N | F | M |
| B.CN.x.B05.EU363829 | N | F | M |
| B.CO.01.PCM039.AY561239 | N | F | A |
| B.GB.04.MM39d11p.HM586193 | N | F | M |
| B.GB.08.F455b_B4.HQ595778 | N | V | E |
| B.GB.x.MB314.Y13719 | N | F | M |
| B.JP.05.-426.AB428556 | N | F | X |
| B.US.01.108051_006.HM769944 | D | F | K |
| B.US.06.YOMI_A6.EU578667 | N | F | A |
| B.US.87.SFMHS5.AF025753 | D | F | T |
| B.US.97.1013_03.AY331287 | N | F | X |
| B.US.97.62357_14_D3_4589.EU289189 | K | F | A |
| B.US.97.M02_3_SW.U84854 | D | F | S |
| B.US.x.F1540TOB8U.GU728134 | S | F | T |
| B.US.x.H0002GH.DQ222211 | D | F | K |
| B.US.x.L3516TOB8U.GU728392 | D | F | M |

-continued

| strain_name | 276 | 277 | 278 |
|---|---|---|---|
| C.BW.00.00BW076820.AF443089 | A | L | T |
| C.BW.00.00BW087421.AF443090 | N | L | A |
| C.BW.00.00BW18595.AF443099 | N | I | E |
| C.BW.00.00BW20361.AF443102 | N | L | A |
| C.BW.96.96BW11B01.AF110971 | I | I | T |
| C.BW.99.99BW47547.AF443086 | S | L | T |
| C.GE.03.03GEMZ033.DQ207941 | D | I | N |
| C.IN.00.HIV_00836_2.EF117265 | K | L | D |
| C.IN.x.CALCMANDAL.AJ276221 | N | L | I |
| C.MW.03.CHV0011247_0478_H2.FJ444251 | E | L | G |
| C.MW.x.BF1266_431a.HM215360 | N | L | E |
| C.TZ.00.390_F1_B7.HQ697983 | N | L | K |
| C.TZ.03.6471_v1_c16.HM215328 | D | L | N |
| C.TZ.x.346_F4_D2_12.HM215302 | N | I | N |
| C.ZA.00.1184MB.AY838566 | N | L | A |
| C.ZA.00.1189MB.AY838565 | N | L | A |
| C.ZA.00.1225MB.AY463227 | N | L | I |
| C.ZA.00.J112MA.AY838568 | N | L | K |
| C.ZA.02.02ZAPS005MB1.DQ351235 | D | L | T |
| C.ZA.02.02ZAPS013MB1.DQ351222 | N | L | A |
| C.ZA.02.02ZAPS014MB1.DQ351218 | N | L | A |
| C.ZA.03.03ZAPS032MB1.DQ445633 | N | L | A |
| C.ZA.03.03ZAPS056MB1.DQ396374 | N | L | K |
| C.ZA.03.03ZAPS066MB2.DQ396375 | N | M | K |
| C.ZA.03.03ZAPS067MB2.DQ396389 | N | L | E |
| C.ZA.03.03ZAPS116MB1.DQ445635 | N | L | A |
| C.ZA.03.03ZAPS136MB1.DQ351231 | N | L | A |
| C.ZA.03.03ZAPS151MB1.DQ396392 | K | L | T |
| C.ZA.03.03ZASK034B1.AY878065 | N | P | T |
| C.ZA.03.03ZASK078B1.AY901971 | K | L | T |
| C.ZA.03.03ZASK098B1.AY878061 | N | L | A |
| C.ZA.03.03ZASK224MB1.DQ275664 | K | L | T |
| C.ZA.03.03ZASK232B1.DQ093589 | D | L | T |
| C.ZA.04.04ZAPS157MB1.DQ351232 | N | L | A |
| C.ZA.04.04ZASK139B1.AY878072 | D | L | T |
| C.ZA.04.04ZASK168B1.AY878058 | D | L | T |
| C.ZA.04.04ZASK181B1.AY878062 | S | L | T |
| C.ZA.04.04ZASK204B1.DQ056414 | N | L | A |
| C.ZA.04.SK144B1.AY703911 | N | L | A |
| C.ZA.05.05ZAFV5.DQ382363 | N | L | A |
| C.ZA.05.CAP174_4w.GQ999981 | N | L | A |
| C.ZA.05.CAP239_5w_F1.GQ999991 | N | I | L |
| C.ZA.06.2833264.HQ595757 | N | L | A |
| C.ZA.06.CHV0005989_CAP129.1.15B2.FJ443417 | K | L | E |
| C.ZA.06.CHV0006091_CAP222.1.11A6.FJ443515 | D | L | E |
| C.ZA.07.3514597.HQ595759 | N | M | A |
| C.ZA.07.CHV0008598_CAP40.2.01F2.FJ443865 | N | L | K |
| C.ZA.09.704MC004N.GU080162 | S | L | T |
| C.ZA.09.704MC016N.GU080173 | D | L | E |
| C.ZA.98.TV013B.AF391246 | S | L | E |
| C.ZA.99.COT9.DQ447272 | N | I | K |
| C.ZA.99.LT36.AY522729 | N | L | A |
| C.ZM.02.14M_BML_1012.HM036760 | N | L | A |
| C.ZM.02.21M_BML_1012.GU939143 | N | L | A |
| C.ZM.04.Z205FPB5NOV04ENV5.2.GQ485436 | N | L | A |
| D.TZ.87.87TZ4622.U65075 | S | L | T |
| D.UG.97.9FPC2.EU853126 | N | L | A |
| D.UG.97.pt632.EU281996 | S | L | T |
| D.UG.98.98UG57131.AF484505 | N | I | K |
| D.UG.99.99UGA07412.AF484477 | N | X | X |
| D.UG.99.99UGD23550.AF484485 | K | L | E |
| D.YE.01.01YE386.AY795903 | N | L | A |
| F1.RU.08.D88_845.GQ290462 | N | I | K |
| K.CD.97.97ZR_EQTB11.AJ249235 | D | I | T |
| U.NL.01.U_NL_01_H10986_C11.EF029069 | N | I | I |
| 01_AE.CF.90.90CF402.U51188 | D | L | T |
| 01_AE.CN.06.CNE3.HM215410 | D | L | T |
| 01_AE.CN.07.BJX4_6.GU475020 | N | L | A |
| 01_AE.TH.00.00TH_C3347.AY945721 | N | L | E |
| 01_AE.TH.01.OUR414I.AY358050 | N | L | A |
| 01_AE.TH.06.99PL2.EU743787 | N | I | K |
| 01_AE.TH.95.NI1144.AF070703 | N | L | A |
| 01_AE.TH.97.97TH6_107.AY125894 | N | P | T |
| 02_AG.CM.01.01CM_0119MA.GU201498 | D | I | T |
| 02_AG.CM.01.01CM_0186BA.GU201500 | D | I | T |
| 02_AG.CM.01.01CM_4410HAL.AY371142 | S | I | T |
| 02_AG.CM.02.02CM_4082STN.AY371141 | S | I | T |

-continued

| strain_name | 276 | 277 | 278 |
|---|---|---|---|
| 02_AG.CM.04.250.EU513189 | N | T | I |
| 02_AG.US.99.99US_MSC1134.AY444809 | S | L | T |
| 05_DF.BE.93.VI961.AF076998 | N | I | L |
| 07_BC.CN.x.CH110.EF117257 | K | L | T |
| 14_BG.ES.00.X477.AF423759 | N | F | X |
| 14_BG.ES.05.X772_8.FJ670528 | N | F | X |
| 17_BF.PE.02.PE02_PCR0155.EU581828 | N | I | F |
| 24_BG.ES.08.X2456_2.FJ670526 | N | F | A |
| 35_AD.AF.06.047H.GQ477443 | N | I | L |
| 01B.MY.04.04MYKL016_1.DQ366663 | X | L | T |
| 02A1.GH.97.AG2.AB052867 | N | L | A |
| 02A1U.CM.05.280.EU513183 | D | I | T |
| 02G.CM.02.02CM_3228MN.AY371147 | N | I | L |
| A1C.TZ.97.97TZ06.AF361876 | D | L | T |
| A1D.DK.96.FSA.DQ912822 | D | I | L |
| A1D.UG.98.98UG57129.AF484503 | N | I | I |
| AC.TZ.04.6540_v4_c1.HM215330 | H | I | G |
| AC.TZ.x.605_F4_12_5.HM215322 | D | L | E |
| BF1.BR.99.BREPM107.AY771588 | N | I | K |
| BF1.ES.02.X1241.AY536238 | N | I | A |
| BF1.IT.05.83166.GU595152 | N | I | X |
| CD.TZ.x.89_F1_2_25.HM215349 | E | I | T |
| CF1.MW.07.CH010180_w12_p1.HM204593 | N | L | K |
| DF.CM.93.CA4.AJ277819 | N | I | R |
| DU.CM.x.247.EU683891 | D | F | T |
| GKU.SE.95.SE9010.AY352655 | D | M | T |
| O.BE.87.ANT70.L20587 | D | I | L |
| O.CM.96.96ABB009.AF383231 | D | I | K |
| O.CM.98.98CMA124.AF383245 | N | I | M |
| O.CM.98.98CMA307.AF383246 | D | I | R |
| O.CM.98.98CMA323.AF383248 | S | I | T |
| O.CM.98.98CMA407.AF383250 | N | I | F |
| O.FR.92.VAU.AF407418 | D | I | S |
| N.CM.02.DJO0131.AY532635 | — | — | N |
| N.CM.02.SJGddd.GQ324959 | — | — | N |
| N.CM.04.04CM_1015_04.DQ017382 | — | — | X |
| N.CM.06.U14296.GQ324962 | — | — | — |
| N.CM.06.U14842.GQ324958 | S | D | S |
| N.CM.95.YBF30.AJ006022 | — | — | N |
| N.CM.97.YBF106.AJ271370 | — | — | — |
| CPZ.CD.90.ANT.U42720 | R | K | N |
| CPZ.CM.05.SIVcpzEK505.DQ373065 | — | — | N |
| CPZ.CM.05.SIVcpzLB7.DQ373064 | — | — | — |
| CPZ.CM.98.CAM3.AF115393 | — | — | — |
| CPZ.CM.98.CAM5.AJ271369 | D | L | R |

HIV strains lacking glycan at 276 in the Wu et al Science 2010 panel:

| strain_name | 276 | 277 | 278 |
|---|---|---|---|
| CRF07_BC.187.CH110.2 | K | L | T |
| B-trans.69.62357.14.D3 | K | F | A |
| D.120.247.23 | D | F | T |
| CRF01_AE.124.620345.c1 | D | I | T |
| CRF01_AE.131.C3347.c11 | N | L | E |
| CRF01_AE.133.CNE3 | D | L | T |
| AC.153.6545.v4.c1 | D | I | T |
| AC.155.6540.v4.c1 | H | I | G |
| A.3.DJ263.8 | D | I | T |
| CRF02_AG.170.250.4 | N | T | I |
| CRF02_AG.176.280.5 | D | I | T |

There are 52 unique and fully defined sequons at 276 (combinations of amino acids at 276, 277, 278) that lack the glycan at 276. These are listed below. Note: "-" indicates a deletion.

| | | | |
|---|---|---|---|
| 1 | — | — | — |
| 2 | — | — | N |
| 3 | A | L | T |
| 4 | D | F | K |
| 5 | D | F | M |
| 6 | D | F | S |
| 7 | D | F | T |
| 8 | D | I | K |
| 9 | D | I | L |
| 10 | D | I | N |
| 11 | D | I | R |
| 12 | D | I | S |
| 13 | D | I | T |
| 14 | D | L | E |
| 15 | D | L | N |
| 16 | D | L | R |
| 17 | D | L | T |
| 18 | D | M | T |
| 19 | E | I | T |
| 20 | E | L | G |
| 21 | H | I | G |
| 22 | I | I | T |
| 23 | K | F | A |
| 24 | K | L | D |
| 25 | K | L | E |
| 26 | K | L | T |
| 27 | N | F | A |
| 28 | N | F | M |
| 29 | N | I | A |
| 30 | N | I | E |
| 31 | N | I | F |
| 32 | N | I | I |
| 33 | N | I | K |
| 34 | N | I | L |
| 35 | N | I | M |
| 36 | N | I | N |
| 37 | N | I | R |
| 38 | N | L | A |
| 39 | N | L | E |
| 40 | N | L | I |
| 41 | N | L | K |
| 42 | N | M | A |
| 43 | N | M | K |
| 44 | N | P | T |
| 45 | N | T | I |
| 46 | N | V | E |
| 47 | R | K | N |
| 48 | S | D | S |
| 49 | S | F | T |
| 50 | S | I | T |
| 51 | S | L | E |
| 52 | S | L | T |

FIG. 1 depicts a binding specificity evaluation. The binding specificity of c1d1_N386D and core gp120 is compared against with a panel of CD4bs-directed antibodies and CD4-IgG2. The CD4bs-directed antibodies tested included the broadly neutralizing antibodies b12, VRC01 and VRC03, and the non-neutralizing antibodies b13, m14, m18, F105, and 15e. In this experiment, each antibody (and CD4-IgG2) was captured on the SPR sensor chip, and c1d1 and gp120 constructs were flowed as analytes. gp120 was used at a concentration of 100 nM, while the c1d1 was used at a concentration of 1 μM. The results show that c1d1 binds only to the neutralizing CD4bs antibodies, while gp120 binds to CD4 and all antibodies tested.

FIG. 2 depicts SPR data and fit for eOD_VH1-2_v6.0 binding to germline VRC01. VRC01_GL IgG was captured on the sensor surface by anti-human IgG; eOD_VH1-2_v6.0 was flowed as analyte at the following concentrations: 6.9 nM, 20.6 nM, 61.7 nM, 185.2 nM, 555.6 nM, 1.67 mcM, 5.0 mcM. The kinetic fit to the data using a 1:1 binding model gives $k_{on}=1.57\times10^4$ $s^{-1}M^{-1}$, $k_{off}=6.83\times10^{-4}$ $s^{-1}$, and $K_D=k_{off}/k_{on}=43.6$ nM.

FIG. 3 depicts SPR data and fit for eOD_VH1-2_v6.0 binding to mature VRC01. VRC01 IgG was captured on the sensor surface by anti-human IgG; eOD_VH1-2_v6.0 was flowed as analyte at the following concentrations: 457 pM, 1.37 nM, 4.11 nM, 12.3 nM, 37.0 nM, 11.1 nM, 333 nM. The kinetic fit to the data using a 1:1 binding model with mass-transport gives $k_{on}=1.48\times10^5$ s$^{-1}$M$^{-1}$, $k_{off}=2.509\times10^{-4}$ s$^{-1}$, and $K_D=k_{off}/k_{on}=1.7$ nM.

Figure 4A:
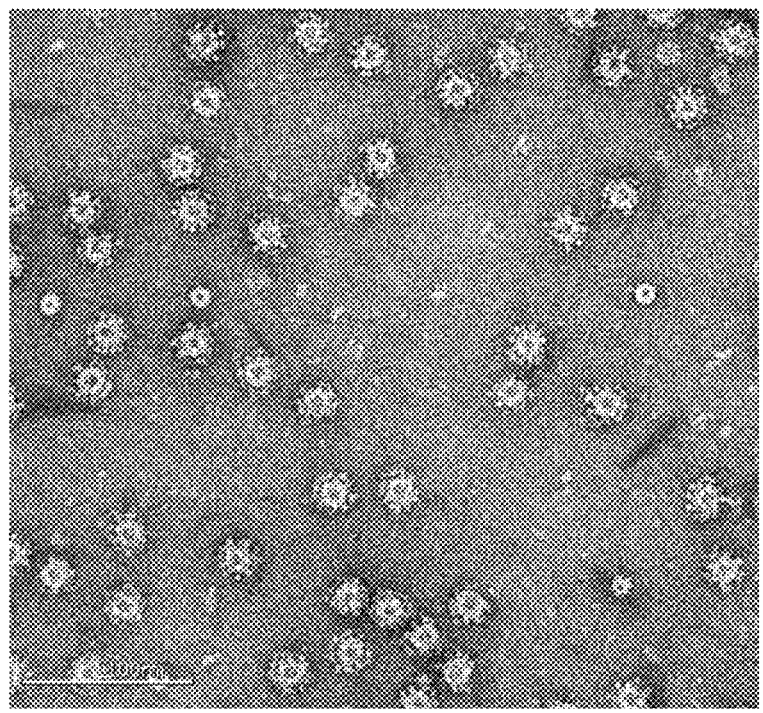
FIG. 4A depicts negative stain electron micrographs showing particles of eOD_VD(−)_60mer_1hqk_3 and eOD_VH1-2_v6.0_1hqk_1.
Figure 4B:
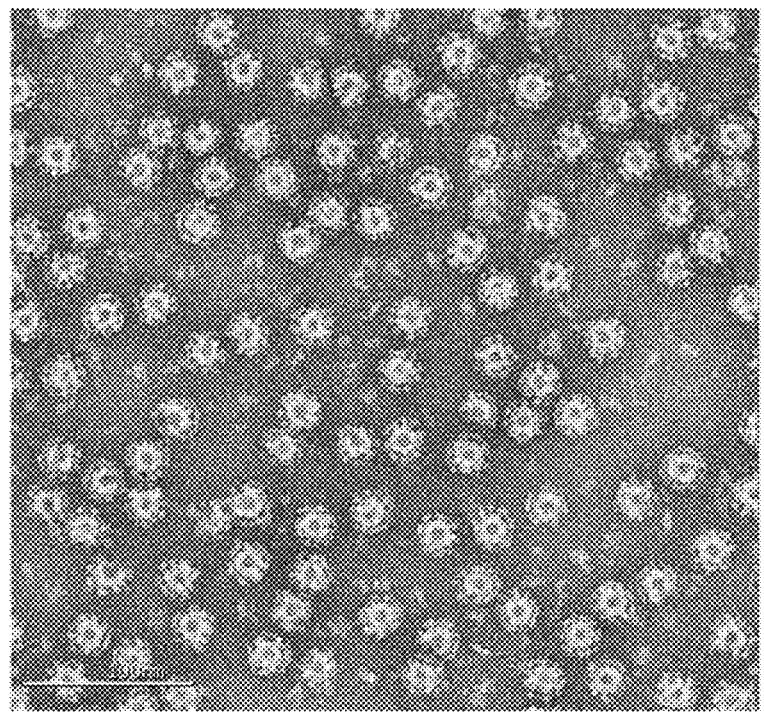
FIG. 4B depicts negative stain electron micrographs showing particles of eOD_VD(−)_60mer_1hqk_3 and and eOD_VH1-2_v6.0_1hqk_1.

FIGS. 4A-B depict negative stain electron micrographs showing particles of eOD_VD(-)_60mer_1hqk_1 and eOD) VH1-2_v6.0_1hqk_1.

Figure 5A:
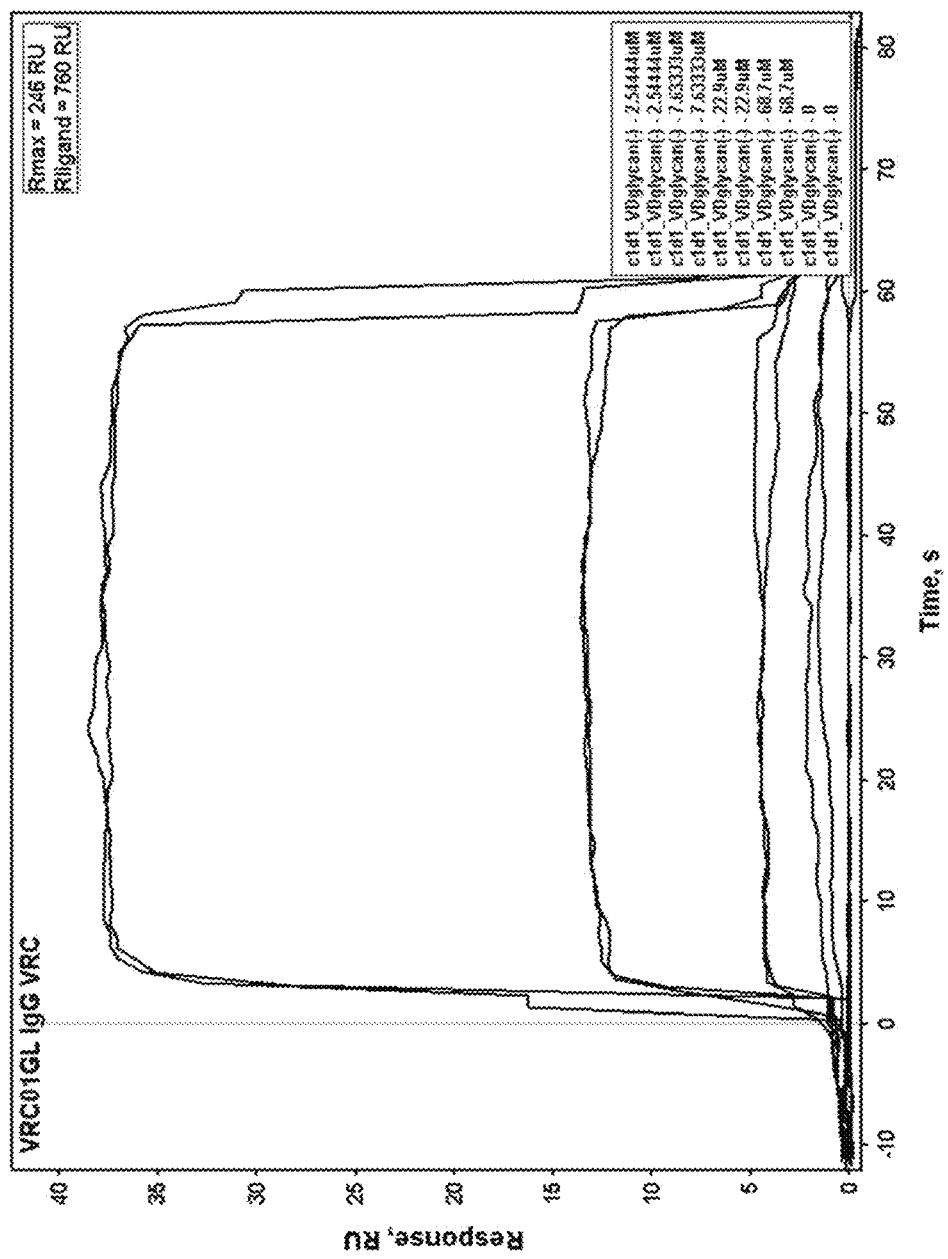
FIG. 5A depicts SPR data showing binding of germline VRC01 to eOD_VD(−) monomer and eOD_VD(−)_60mer_1hqk_3+/−D368R mutation. The control particle (eOD_VD(−)_60mer_1hqk_3+D368R) carries the D368R mutation that significantly reduces binding of mature VRC01 to eOD_VD(−) and completely eliminates detectable binding to germline VRC01. Germline VRC01 was captured on the sensor chip, and monomer and 60mers were flowed as analytes. Monomer was flowed at 2.5 mcM, 7.6 mcM, 22.9 mcM, 68.7 mcM. 60mers were flowed at 23.0 mcM (eOD_VD(−)_60mer_1hqk_3) and 27.0 mcM (eOD_VD(−)_60mer_1hqk_3+D368R) equivalent eOD monomer concentrations. The data show that avidity from the 60mer significantly reduces off-rate, hence significantly strengthens binding, of eOD_VD(−)_60mer_1hqk_3 for germline VRC01. The strengthened binding is specific because the D368R particle shows no detectable binding.
Figure 5B:
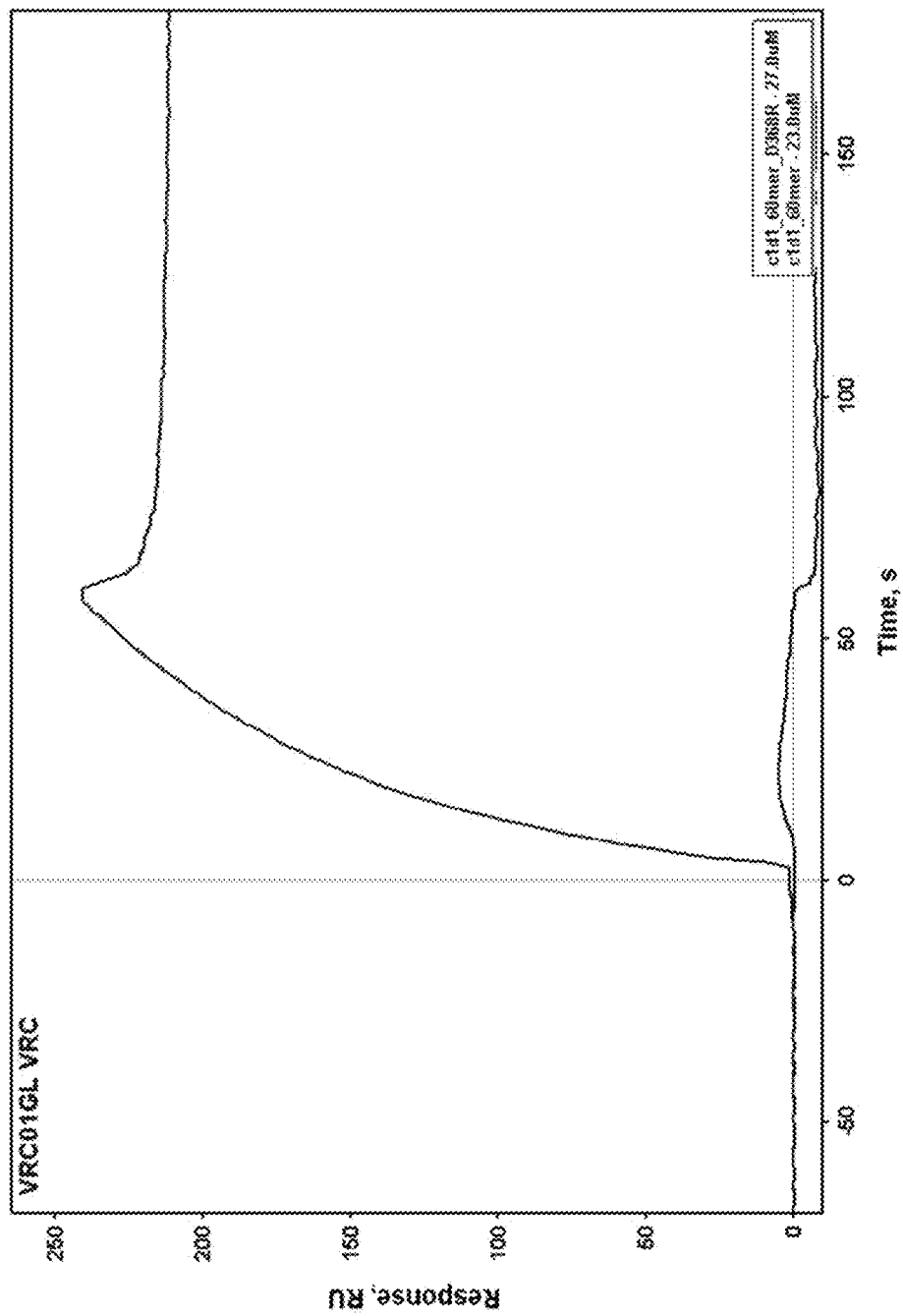
FIG. 5B depicts SPR data showing binding of germline VRC01 to eOD_VD(−) monomer and eOD_VD(−)_60mer_1hqk_3+/−D368R mutation. The control particle (eOD_VD(−)_60mer_1hqk_3+D368R) carries the D368R mutation that significantly reduces binding of mature VRC01 to eOD_VD(−) and completely eliminates detectable binding to germline VRC01. Germline VRC01 was captured on the sensor chip, and monomer and 60mers were flowed as analytes. Monomer was flowed at 2.5 mcM, 7.6 mcM, 22.9 mcM, 68.7 mcM. 60mers were flowed at 23.0 mcM (eOD_VD(−)_60mer_1hqk_3) and 27.0 mcM (eOD_VD(−)_60mer_1hqk_3+D368R) equivalent eOD monomer concentrations. The data show that avidity from the 60mer significantly reduces off-rate, hence significantly strengthens binding, of eOD_VD(−)_60mer_1hqk_3 for germline VRC01. The strengthened binding is specific because the D368R particle shows no detectable binding.

FIGS. 5A-B depict SPR data showing binding of germline VRC01 to eOD_VD(-) monomer and eOD_VD(-)_60mer_1hqk_1+/-D368R mutation. The control particle (eOD_VD(-)_60mer_1hqk_1+D368R) carries the D368R mutation that significantly reduces binding of mature VRC01 to eOD_VD(-) and completely eliminates detectable binding to germline VRC01. Germline VRC01 was captured on the sensor chip, and monomer and 60mers were flowed as analytes. Monomer was flowed at 2.5 mcM, 7.6 mcM, 22.9 mcM, 68.7 mcM. 60mers were flowed at 23.0 mcM (eOD_VD(-)_60mer_1hqk_1) and 27.0 mcM (eOD_VD(-)_60mer_1hqk_1+D368R) equivalent eOD monomer concentrations. The data show that avidity from the 60mer significantly reduces off-rate, hence significantly strengthens binding, of eOD_VD(-)_60mer_1hqk_1 for germline VRC01. The strengthened binding is specific because the D368R particle shows no detectable binding.

It is noted that these therapeutics may be a chemical compound, a composition which may comprise a polypeptide of the present invention and/or antibody elicited by such a chemical compound and/or portion thereof or a pharmaceutically acceptable salt or a composition which may comprise a polypeptide of the invention, and may be administered alone or as an active ingredient in combination with pharmaceutically acceptable carriers, diluents, and vehicles, as well as other active ingredients.

The compounds or compositions may be administered orally, subcutaneously or parenterally including intravenous, intraarterial, intramuscular, intraperitoneally, and intranasal administration as well as intrathecal and infusion techniques.

It is noted that humans are treated generally longer than the mice or other experimental animals which treatment has a length proportional to the length of the disease process and drug effectiveness. The doses may be single doses or multiple doses over a period of several days, but single doses are preferred. Thus, one may scale up from animal experiments, e.g., rats, mice, and the like, to humans, by techniques from this disclosure and documents cited herein and the knowledge in the art, without undue experimentation.

The treatment generally has a length proportional to the length of the disease process and drug effectiveness and the patient being treated.

When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier may be a solvent or dispersing medium containing, for example, water, ethanol, polyol (for example, glycerol, propylene glycol, liquid polyethylene glycol, and the like), suitable mixtures thereof, and vegetable oils.

Proper fluidity may be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions.

Additionally, various additives which enhance the stability, sterility, and isotonicity of the compositions, including antimicrobial preservatives, antioxidants, chelating agents, and buffers, may be added. Prevention of the action of microorganisms may be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form may be brought about by the use of agents delaying absorption, for example, aluminum monostearate and gelatin. According to the present invention, however, any vehicle, diluent, or additive used would have to be compatible with the compounds.

Sterile injectable solutions may be prepared by incorporating the compounds utilized in practicing the present invention in the required amount of the appropriate solvent with various amounts of the other ingredients, as desired.

A pharmacological formulation of the present invention, e.g., which may comprise a therapeutic compound or polypeptide of the present invention, may be administered to the patient in an injectable formulation containing any compatible carrier, such as various vehicles, adjuvants, additives, and diluents; or the compounds utilized in the present invention may be administered parenterally to the patient in the form of slow-release subcutaneous implants or targeted delivery systems such as monoclonal antibodies, iontophoretic, polymer matrices, liposomes, and microspheres.

A pharmacological formulation of the compound and composition which may comprise a polypeptide utilized in the present invention may be administered orally to the patient. Conventional methods such as administering the compounds in tablets, suspensions, solutions, emulsions, capsules, powders, syrups and the like are usable. Known techniques, which deliver the compound orally or intravenously and retain the biological activity, are preferred.

In one embodiment, a formulation of the present invention may be administered initially, and thereafter maintained by further administration. For instance, a formulation of the invention may be administered in one type of composition and thereafter further administered in a different or the same type of composition. For example, a formulation of the invention may be administered by intravenous injection to bring blood levels to a suitable level. The patient's levels are then maintained by an oral dosage form, although other farms of administration, dependent upon the patient's condition, may be used. In the instance of a vaccine composition, the vaccine may be administered as a single dose, or the vaccine may incorporate set booster doses. For example, booster doses may comprise variants in order to provide protection against multiple clades of HIV.

The quantity to be administered will vary for the patient being treated and whether the administration is for treatment or prevention and will vary from a few micrograms to a few milligrams for an average 70 kg patient, e.g., 5 micrograms to 5 milligrams such as 500 micrograms, or about 100 ng/kg of body weight to 100 mg/kg of body weight per administration and preferably will be from 10 pg/kg to 10 mg/kg per administration. Typically however, the antigen is present in an amount on, the order of micrograms to milligrams, or, about 0.001 to about 20 wt %, preferably about 0.01 to about 10 wt %, and most preferably about 0.05 to about 5 wt %.

Of course, for any composition to be administered to an animal or human, including the components thereof, and for any particular method of administration, it is preferred to determine therefor: toxicity, such as by determining the lethal dose (LD) and LD$_{50}$ in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations may be ascertained without undue experimentation. For instance, dosages may be readily ascertained by those skilled in the art from this disclosure and the knowledge in the art. Thus, the skilled artisan may readily determine the amount of compound and optional additives, vehicles, and/or carrier in compositions and to be administered in methods of the invention. Typically, an adjuvant or additive is commonly used as 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Such determinations do not require undue experimentation from the knowledge of the skilled artisan, this disclosure and the documents cited herein. And, the time for sequential administrations may be ascertained without undue experimentation.

Examples of compositions which may comprise a therapeutic of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions may also be lyophilized. The compositions may contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention may be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers may preferably dispense a metered dose or, a dose having a particular particle size.

Compositions of the invention may contain pharmaceutically acceptable flavors and/or colors for rendering them more appealing, especially if they are administered orally. The viscous compositions may be in the form of gels, lotions, ointments, creams and the like (e.g., for transdermal administration) and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions may approach solid or gelatin forms, which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally. Viscous compositions, on the other hand, may be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the active compound. Minor amounts of other ingredients such as pH adjusters (e.g., a base such as NaOH), emulsifiers or dispersing agents, buffering agents, preservations, wetting agents, jelling agents, (e.g., methylcellulose), colors and/or flavors may also be present. The compositions may be isotonic, i.e., it may have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Viscous compositions are normally prepared from solutions by the addition of such thickening agents.

A pharmaceutically acceptable preservative may be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions should be selected to be chemically inert with respect to the active compound. This will present no problem to those skilled in chemical and pharmaceutical principles, or problems may be readily avoided by reference to standard texts or by simple experiments (not involving undue experimentation), from this disclosure and the documents cited herein.

It is generally envisaged that compounds and compositions of the invention will be administered by injection, as such compounds are to elicit anti-HIV antibodies, and the skilled artisan may, from this disclosure and the knowledge in the art, formulate compounds and compositions identified by herein methods for administration by injection and administer such compounds and compositions by injection.

The inventive compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions may be administered in dosages and by techniques well known to those skilled in the medical arts taking into consideration such factors as the age, sex, weight, and condition of the particular patient, and the composition form used for administration (e.g., solid vs. liquid). Dosages for humans or other mammals may be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

Although the present invention and its advantages have been described in detail, it should be understood that various changes, substitutions and alterations can be made herein without departing from the spirit and scope of the invention as defined in the appended claims.

The invention claimed is:

1. A non-naturally occurring engineered outer domain (eOD) protein comprising one or more engineered modifications and/or mutations of SEQ ID NO: 12.

2. The protein of claim 1 wherein the protein
   (a) maintains high affinity for broadly neutralizing antibodies b12 and VRC01;
   (b) binds with little or no detectable affinity to CD4 or non-neutralizing CD4bs antibodies;
   (c) lacks the V3 loop and beta 20/21 hairpin and is about 175 residues;
   (d) displays no evidence of aggregation;
   (e) have N and C termini located distal from the CD4bs to allow coupling, by chemical or genetic means, to larger particles for the purpose of multimeric display; and/or
   (f) is expressed with a minimum of only two (2) glycans.

3. The protein of claim 1 wherein the modification and/or mutation is:
   (a) mutating D at position 47;
   (b) mutating H at position 61;
   (c) mutating E at position 62;
   (d) mutating K at position 87;
   (e) mutating V at position 208;
   (f) mutating D at position 276;
   (g) mutating R at position 278;
   (h) mutating N at position 279;
   (i) mutating I at position 283;
   (j) mutating S at position 362;
   (k) mutating F at position 371;
   (l) mutating E at position 429;
   (m) deleting residues 432 to 437;
   (n) mutating I at position 455; and/or
   (o) mutating I at position 467;
   wherein each mutation or modification is relative to the sequence of SEQ ID NO: 12.

4. The protein of claim 1 wherein the modification and/or mutation is:
   (a) removing a glycosylation site at position 276;
   (b) E47D;
   (c) Y61H;
   (d) D62E;
   (e) E87K;
   (f) I208V;
   (g) N276D;
   (h) A278R or T278R;
   (i) D279N;
   (j) T283I;
   (k) replacing RPNNGGSGSGGDIRQA with GAG;
   (l) K362S;
   (m) I371F;
   (n) K429E;
   (o) deleting residues 432-437 (RAIVIYAP);
   (p) T455I; and/or
   (q) V467I;
   wherein each mutation or modification is relative to the sequence of SEQ ID NO: 12.

5. The protein of claim 1 wherein modification and/or mutation is a deletion of the glycosylation site at amino acid position 276 and/or deletion of glycosylation sites on the V5 loop at positions 460, 461, 462, or 463, wherein each mutation or modification is relative to the sequence of SEQ ID NO: 12.

6. A nucleotide sequence having at least 90% homology or 95% sequence to the nucleotide sequence encoding the protein of claim 1.

7. A nucleotide sequence having at least 90% homology or 95% sequence to the nucleotide sequence encoding the protein of claim 2.

8. A nucleotide sequence having at least 90% homology or 95% sequence to the nucleotide sequence encoding the protein of claim 3.

9. A nucleotide sequence having at least 90% homology or 95% sequence to the nucleotide sequence encoding the protein of claim 4.

10. A nucleotide sequence having at least 90% homology or 95% sequence to the nucleotide sequence encoding the protein of claim 5.

11. A protein sequence having at least 90% or 95% sequence homology or identity with the protein of claim 1.

12. A protein sequence having at least 90% or 95% sequence homology or identity with the protein of claim 2.

13. A protein sequence having at least 90% or 95% sequence homology or identity with the protein of claim 3.

14. A protein sequence having at least 90% or 95% sequence homology or identity with the protein of claim 4.

15. A protein sequence having at least 90% or 95% sequence homology or identity with the protein of claim 5.

16. A method of eliciting an immune response which comprising systemically administering to an animal in need thereof an effective amount of the protein of claim 1.

17. A method of eliciting an immune response which comprising systemically administering to an animal in need thereof an effective amount of the protein of claim 2.

18. A method of eliciting an immune response which comprising systemically administering to an animal in need thereof an effective amount of the protein of claim 3.

19. A method of eliciting an immune response which comprising systemically administering to an animal in need thereof an effective amount of the protein of claim 4.

20. A method of eliciting an immune response which comprising systemically administering to an animal in need thereof an effective amount of the protein of claim 5.

* * * * *